(12) United States Patent
Chen

(10) Patent No.: US 6,833,378 B2
(45) Date of Patent: Dec. 21, 2004

(54) CORTICOTROPIN RELEASING FACTOR ANTAGONISTS

(75) Inventor: Yuhpyng L. Chen, Waterford, CT (US)

(73) Assignee: Pfizer Inc, New York, NY (US)

( * ) Notice: Subject to any disclaimer, the term of this patent is extended or adjusted under 35 U.S.C. 154(b) by 54 days.

(21) Appl. No.: 09/761,995

(22) Filed: Jan. 17, 2001

(65) Prior Publication Data

US 2002/0016328 A1 Feb. 7, 2002

Related U.S. Application Data

(60) Provisional application No. 60/176,611, filed on Jan. 18, 2000.

(51) Int. Cl.$^7$ .................. A61K 31/44; A61K 43/40; C07D 213/54; C07D 213/62; C07D 213/75

(52) U.S. Cl. .................. 514/335; 514/336; 514/337; 514/338; 514/339; 514/340; 514/341; 514/342; 514/343; 514/344; 514/345; 514/349; 514/350; 514/351; 514/352; 514/353; 514/354; 514/355; 514/356; 514/357; 546/153; 546/155; 546/156; 546/157; 546/158; 546/159; 546/167; 546/255; 546/256; 546/261; 546/262; 546/263; 546/264; 546/265; 546/266; 546/267; 546/278.4; 546/296; 546/297; 546/307; 544/295; 544/296; 544/300; 544/310; 544/316; 544/317; 544/319

(58) Field of Search .................. 514/335, 336, 514/337–345, 348, 255, 256, 269, 272, 274, 275, 312, 314, 332, 333, 349–357; 546/261–265, 266, 267, 278.4, 296, 297, 307, 153, 155, 156–159, 255, 256, 167; 544/295, 296, 300, 310, 316, 317, 319, 320, 326, 328, 329, 331, 333, 397, 405

(56) References Cited

U.S. PATENT DOCUMENTS

| 4,605,642 A | 8/1986 | Rivier et al. .................. 514/12 |
| 4,839,353 A | 6/1989 | Hosoi et al. .................. 514/212 |
| 5,063,245 A | 11/1991 | Abreu et al. .................. 514/404 |
| 5,691,364 A | 11/1997 | Buckman et al. ............ 514/341 |
| 5,962,479 A | * 10/1999 | Chen .......................... 514/348 |
| 6,130,188 A | * 10/2000 | Scheiblich et al. ......... 504/253 |

FOREIGN PATENT DOCUMENTS

| DE | 3145287 | 11/1981 |
| EP | 0475411 | 9/1991 |
| EP | 0582804 | 9/1996 |
| WO | 9413676 | 6/1994 |
| WO | 9510506 | 4/1995 |
| WO | 95/33750 | * 12/1995 |

OTHER PUBLICATIONS

Co-pending U.S. Patent Application Ser. No. 09/580,791.
Kamel et al., Pharmazie 1990, 45(2), 139–140.
Demina et al., Khim. Farm. Zh., 1993, 27(7), pp. 34–35 (with English summary).

Demina et al., Geterotsikl Soedin, 1992 (11), pp. 1506–1508 (with English summary).
Chhabria et al, *Heterocycles*, vol.51, No.11, 1999, 2723–2729.
Owens et al., Pharm. Rev. vol. 43 (1991) pp. 425–473.
Chem Abst. vol. 72 (1970), abstract No. 110080.
Robbins et al., Can. J. Chem. vol. 55 (1977) pp. 1251–1259.
Cossey etal., Australian Journal of Chemistry vol. 29, No. 5 (May 1976).
De Souza, Psychoneuroendocrinology, vol. 20, No. 8, pp. 789–819 (1995).
Fackelmann, K. A. and Raloff, J., Science News (Sep. 25, 1993), vol. 144, p. 196.
Lyons, M.K. et al., Brain Research, vol. 545, (1991) pp. 339–342.
Stratakis, C.A., and Chrousos, G.P. Endocrinology: Basic and Clinical Principles, pp. 185–209, 2002.
Strijbos, P.J.L.M. et al, Brain Res. 656, pp. 405–408 1994.
Chalmers, D.T. et al., Trends in Pharmacological Sciences, vol. 17, pp 166–172 (1996).

\* cited by examiner

*Primary Examiner*—Richard L. Raymond
*Assistant Examiner*—Tamthom N. Truong
(74) *Attorney, Agent, or Firm*—Peter C. Richardson; Paul H. Ginsburg; Andrea E. Dorigo

(57) ABSTRACT

Corticotropin-releasing factor (CRF) antagonists having the formulae

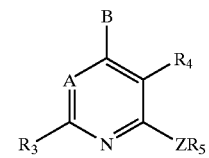

I

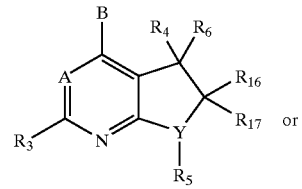

II

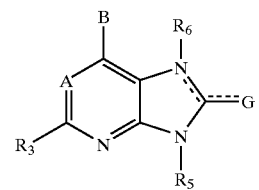

III wherein the dashed lines, A, B, Y, Z, G, $R_3$, $R_4$, $R_5$, $R_6$, $R_{16}$ and $R_{17}$ are as defined in the application, and processes for preparing them. These compounds and their pharmaceutically acceptable salts are useful in the treatment disorders including CNS and stress-related disorders.

34 Claims, No Drawings

CORTICOTROPIN RELEASING FACTOR ANTAGONISTS

This application claims priority under 35 U.S.C. 119 (e) of U.S. Provisional Patent Application 60/176,611, filed Jan. 18, 2000.

BACKGROUND OF THE INVENTION

This invention relates to pyridines, pyrimidines, purinones, pyrrolopyrimidinones and pyrrolopyridinones, processes for preparing them, pharmaceutical compositions containing them, and methods of using them to treat certain central nervous system (CNS) and other disorders.

CRF antagonists are mentioned in U.S. Pat. No. 4,605, 642, issued Aug. 12, 1986, and U.S. Pat. No. 5,063,245, issued Nov. 5, 1991, referring to peptides and pyrazolinones, respectively. CRF antagonists are also described in U.S. Pat. No. 5,962,479, issued Oct. 5, 1999. The importance of CRF antagonists is set out in the literature, e.g., as discussed in U.S. Pat. No. 5,063,245, which is incorporated herein by reference. A recent outline of the different activities possessed by CRF antagonists is found in M. J. Owens et al., Pharm. Rev., Vol. 43, pages 425 to 473 (1991), also incorporated herein by reference. Based on the research described in these two and other references, CRF antagonists are effective in the treatment of a wide range of stress-related illnesses, such as depression, anxiety, headache, irritable bowel syndrome, inflammatory diseases, immune suppression, Alzheimer's disease, gastrointestinal diseases, anorexia nervosa, hemorrhagic stress, drug and alcohol withdrawal symptoms, drug addiction, infertility, head trauma, stroke, and stress-induced infections in humans and animals. The use of CRF antagonists for treatment of Syndrome X has also been described in U.S. patent application Ser. No. 09/696,822, filed Oct. 26, 2000, and European Patent Application No. 00309441.4, filed Oct. 26, 2000, which are also incorporated in their entireties herein by reference. Methods for using CRF antagonists to treat congestive heart failure are described in U.S. Ser. No. 09/248,073, filed Feb. 10, 1999, now U.S. Pat. No. 6,043, 260 (issued Mar. 28, 2000) which is also incorporated herein in its entirety by reference.

SUMMARY OF THE INVENTION

The present invention provides compounds of the formula

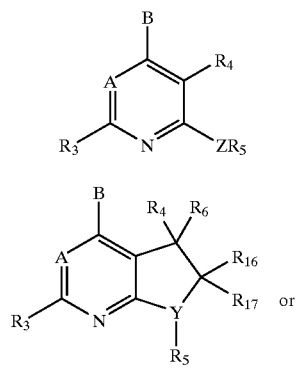

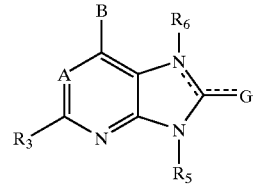

and pharmaceutically acceptable salts thereof, wherein the dashed lines represent optional double bonds, with the proviso that when the dashed line in C---G represent a double bond, then the dashed line in $N(R_6)$---C does not represent a double bond; and with the proviso that when the dashed line in $N(R_6)$---C represents a double bond, $R_6$ is absent in formula III and the dashed line in C---G does not represent a double bond;

A is —$CR_7$ or N;

B is —$NR_1R_2$, —$CR_1R_2R_{11}$, —$C(=CR_2R_{12})R_1$, —$NHCHR_1R_2$, —$OCHR_1R_2$, —$SCHR_1R_2$, —$CHR_2OR_1$, —$CHR_1OR_2$, —$CHR_2SR_1$, —$C(S)R_2$, —$C(O)R_2$, —$CHR_2NR_1R_2$, —$CHR_1NHR_2$, —$CHR_1N(CH_3)R_2$, or —$NR_{12}NR_1R_2$;

when the dashed line in C---G represents a double bond, then G is hydrogen, oxygen, sulfur, NH, or $N(C_1-C_4$ alkyl);

when the dashed line in C---G does not represent a double bond, then C---G is —$C(H)(NH_2)$, $CH_2$, —$C(H)(methoxy)$, —$C(H)(ethoxy)$, —$C(H)(O(C_3-C_4$ alkyl)), —$C(H)(halo)$, —$C(H)(trifluoromethoxy)$, —$C(H)(methyl)$, —$C(H)(ethyl)$, —$C(H)(C_3-C_4$ alkyl), —$C(H)(S(C_1-C_4$ alkyl)), —$C(C_1-C_4$ alkyl)($C_1-C_4$ alkyl), cyclopropyl, —$C(H)(cyclopropyl)$, thiomethoxy, —$C(H)(NH_2)$, —$C(H)(NHCH_3)$, —$C(H)(N(CH_3)_2)$, or —$C(H)(trifluoromethyl)$;

wherein said cyclopropyl, methoxy, ethoxy, $C_3-C_4$ alkyl, and $C_1-C_4$ alkyl groups of C---G may optionally be substituted by one OH, methoxy, or trifluoromethoxy, or may optionally be substituted by from one to six fluoro atoms;

Y is CH or N;

Z is NH, O, S, —$N(C_1-C_2$ alkyl), —$NC(O)CF_3$, or —$C(R_{13}R_{14})$, wherein $R_{13}$ and $R_{14}$ are each, independently, hydrogen, trifluoromethyl or methyl, or one of $R_{13}$ and $R_{14}$ is cyano and the other is hydrogen or methyl, or —$C(R_{13}R_{14})$ is a cyclopropyl group, or Z is nitrogen or CH and forms; a five or six membered heterocyclic ring fused with $R_5$, which ring optionally comprises two or three further hetero members selected independently from oxygen, nitrogen, $NR_{12}$, and $S(O)_m$, and optionally comprises from one to three double bonds, and is optionally substituted with halo, $C_1-C_4$ alkyl, —$O(C_1-C_4$ alkyl), $NH_2$, $NHCH_3$, $N(CH_3)_2$, $CF_3$, or $OCF_3$, with the proviso that said ring does not contain any —S—S—, —S—O—, —N—S—, or —O—O— bonds, and does not comprise more than two oxygen or $S(O)_m$ heterologous members;

$R_1$ is —$C(O)H$, —$C(O)(C_1-C_6$ alkyl), —$C(O)(C_1-C_6$ alkylene)($C_3-C_8$ cycloalkyl), —$C(O)(C_3-C_8$ cycloalkylene) ($C_3-C_8$ cycloalkyl), —$C(O)(C_1-C_6$ alkylene)($C_4-C_8$ heterocycloalkyl), —$C(O)(C_3-C_8$ cycloalkylene)($C_4-C_8$ heterocycloalkyl), —$C_1-C_6$ alkyl, —$C_3-C_8$ cycloalkyl, —$C_4-C_8$ heterocycloalkyl, —($C_1-C_6$ alkylene)($C_3-C_8$ cycloalkyl), —($C_3-C_8$ cycloalkylene)($C_3-C_8$ cycloalkyl), —($C_1-C_6$ alkylene)($C_4-C_8$ heterocycloalkyl), —($C_3-C_8$ cycloalkylene)($C_4-C_8$ heterocycloalkyl), or —O-aryl, or —O—($C_1-C_6$ alkylene)-aryl; wherein said aryl, $C_4-C_8$ heterocycloalkyl, $C_1-C_6$ alkyl, $C_3-C_8$ cycloalkyl, $C_3-C_8$ cycloalkylene, and $C_1-C_6$ alkylene groups may each independently be optionally substituted with from one to six fluoro and may each independently be optionally substituted with one or two substituents $R_8$ independently selected from the group consisting of $C_1-C_4$ alkyl, —$C_3-C_8$ cycloalkyl, hydroxy, fluoro, chloro, bromo, iodo, $CF_3$, —O—($C_1-C_6$ alkyl), —O—($C_3-C_5$ cycloalkyl), —O—CO—($C_1-C_4$ alkyl), —O—CO—NH($C_1-C_4$ alkyl), —O—CO—N($R_{24}$) ($R_{25}$), —N($R_{24}$)($R_{25}$), —S($C_1-C_4$ alkyl), —S($C_3-C_5$ cycloalkyl), —N($C_1-C_4$alkyl)CO($C_1-C_4$ alkyl), —NHCO ($C_1-C_4$ alkyl), —COO($C_1-C_4$ alkyl), —CONH($C_1-C_4$ alkyl), —CON($C_1-C_4$ alkyl)($C_1-C_2$ alkyl), CN, $NO_2$, —$OSO_2$($C_1-C_4$ alkyl), $S^+$($C_1-C_6$ alkyl)($C_1-C_2$ alkyl), —SO ($C_1-C_4$ alkyl) and —$SO_2$($C_1-C_4$ alkyl); and wherein the $C_1-C_6$ alkyl, $C_1-C_6$ alkylene, $C_5-C_8$ cycloalkyl, $C_5-C_8$ cycloalkylene, and $C_5-C_8$ heterocycloalkyl moieties of $R_1$ may optionally independently contain from one to three double or triple bonds; and wherein the $C_1-C_4$ alkyl moieties and the $C_1-C_6$ alkyl moieties of $R_8$ can optionally independently be substituted with hydroxy, $C_1-C_4$ alkyl, amino, aryl, —$CH_2$-aryl, —$C_3-C_5$ cycloalkyl, or —O— ($C_1-C_4$ alkyl), and can optionally independently be substituted with from one to five fluoro, and can optionally contain one or two double or triple bonds; and wherein each heterocycloalkyl group of R contains from one to three heteromoieties selected from oxygen, $S(O)_m$, nitrogen, and $NR_{12}$;

$R_2$ is hydrogen, $C_1-C_{12}$ alkyl, $C_3-C_8$ cycloalkyl, $C_4-C_8$ heterocycloalkyl, —($C_1-C_6$ alkylene)($C_3-C_8$ cycloalkyl), —($C_3-C_8$ cycloalkylene)($C_3-C_8$ cycloalkyl), —($C_1-C_6$ alkylene)($C_4-C_8$ heterocycloalkyl), —($C_3-C_8$ cycloalkylene)($C_4-C_8$ heterocycloalkyl), aryl, —($C_1-C_6$ alkylene)aryl, or —($C_3-C_8$ cycloalkylene)(aryl); wherein each of the foregoing $R_2$ groups may optionally be substituted with from one three substituents independently selected from chloro, fluoro, and $C_1-C_6$ alkyl, wherein one of said one to three substituents can further be selected from bromo, iodo, $C_1-C_6$ alkoxy, —OH, —O—CO—($C_1-C_6$ alkyl), —O—CO—N($C_1-C_4$ alkyl)($C_1-C_2$ alkyl), —S($C_1-C_6$ alkyl), —S(O)($C_1-C_6$ alkyl), —$S(O)_2$($C_1-C_6$ alkyl), $S^+$($C_1-C_6$ alkyl)($C_1-C_2$ alkyl), CN, and $NO_2$; and wherein the $C_1-C_{12}$ alkyl, —($C_1-C_6$ alkylene), —($C_5-C_8$ cycloalkyl), —($C_5-C_8$ cycloalkylene), and —($C_5-C_8$ heterocycloalkyl) moieties of $R_2$ may optionally independently contain from one to three double or triple bonds; and wherein each heterocycloalkyl group of $R_2$ contains from one to three heteromoieties selected from oxygen, $S(O)_m$, nitrogen, and $NR_{12}$;

or where $R_1$ and $R_2$ are as in —$NHCHR_1R_2$, —$OCHR_1R_2$, —$SCHR_1R_2$, —$CHR_1R_2$ or —$NR_1R_2$, $R_1$ and $R_2$ of B may form a saturated 5- to 8-membered ring which may optionally contain one or two double bonds and in which one or two of the ring carbons may optionally be replaced by an oxygen, $S(O)_m$, nitrogen or $NR_{12}$; and which carbocyclic ring can optionally be substituted with from 1 to 3 substituents selected from the group consisting of hydroxy, $C_1-C_4$ alkyl, fluoro, chloro, bromo, iodo, $CF_3$, —O— ($C_1-C_4$ alkyl), —O—CO—($C_1-C_4$ alkyl), —O—CO—NH ($C_1-C_4$ alkyl), —O—CO—N($C_1-C_4$ alkyl)($C_1-C_2$ alkyl), —NH($C_1-C_4$ alkyl), —N($C_1-C_2$ alkyl)($C_1-C_4$ alkyl), —S($C_1-C_4$ alkyl), —N($C_1-C_4$ alkyl)CO($C_1-C_4$ alkyl), —NHCO($C_1-C_4$ alkyl), —COO($C_1-C_4$ alkyl), —CONH ($C_1-C_4$ alkyl), —CON($C_1-C_4$ alkyl)($C_1-C_2$ alkyl), CN, $NO_2$, —$OSO_2$($C_1-C_4$ alkyl), —SO($C_1-C_4$ alkyl), and —$SO_2$($C_1-C_4$ alkyl), wherein one of said one to three substituents can further be selected from phenyl;

$R_3$ is methyl, ethyl, fluoro, chloro, bromo, iodo, cyano, methoxy, $OCF_3$, $NH_2$, $NH(C_1-C_2$ alkyl), $N(CH_3)_2$, —$NHCOCF_3$, —$NHCH_2CF_3$, $S(O)_m(C_1-C_4$ alkyl), $CONH_2$, —$CONHCH_3$, $CON(CH_3)_2$, —$CF_3$, or $CH_2OCH_3$;

$R_4$ is hydrogen, $C_1-C_4$ alkyl, $C_3-C_5$ cycloalkyl, —($C_1-C_4$ alkylene)($C_3-C_5$ cycloalkyl), —($C_3-C_5$ cycloalkylene) ($C_3-C_5$ cycloalkyl), cyano, fluoro, chloro, bromo, iodo, —$OR_{24}$, $C_1-C_6$ alkoxy, —O—($C_3-C_5$ cycloalkyl), —O— ($C_1-C_4$ alkylene)($C_3-C_5$ cycloalkyl), —O—($C_3-C_5$ cycloalkylene)($C_3-C_5$ cycloalkyl), —$CH_2SC(S)O(C_1-C_4$ alkyl), —$CH_2OCF_3$, —$CF_3$, amino, nitro, —$NR_{24}R_{25}$, —($C_1-C_4$ alkylene)—$OR_{24}$, —($C_1-C_4$ alkylene)Cl, —($C_1-C_4$ alkylene)$NR_{24}R_{25}$, —$NHCOR_{24}$, —$NHCONR_{24}R_{25}$, —C=$NOR_{24}$, —$NHNR_{24}R_{25}$, —$S(O)_m$ $R_{24}$, —$C(O)R_{24}$, —$OC(O)R_{24}$, —$C(O)CN$, —$C(O)NR_{24}R_{25}$, —$C(O)NHNR_{24}R_{25}$, and —$COOR_{24}$, wherein the alkyl and alkylene groups of $R_4$ may optionally independently contain one or two double or triple bonds and may optionally independently be substituted with one or two substituents $R_{10}$ independently selected from hydroxy, amino, —$NHCOCH_3$, —$NHCOCH_2C_1$, —$NH(C_1-C_2$ alkyl), —$N(C_1-C_2$ alkyl)($C_1-C_2$ alkyl), —$COO(C_1-C_4$ alkyl), —COOH, —CO($C_1-C_4$ alkyl), $C_1-C_6$ alkoxy, $C_1-C_3$ thioalkyl, cyano and nitro, and with one to four substituents independently selected from fluoro and chloro;

$R_5$ is aryl or heteroaryl and is substituted with from one to four substituents $R_{27}$ independently selected from halo, $C_1-C_{10}$ alkyl, —($C_1-C_4$ alkylene)($C_3-C_8$ cycloalkyl), —($C_1-C_4$ alkylene)($C_4-C_8$ heterocycloalkyl), —($C_3-C_8$ cycloalkyl), —($C_4-C_8$ heterocycloalkyl), —($C_3-C_8$ cycloalkylene)($C_3-C_8$ cycloalkyl), —($C_3-C_8$ cycloalkylene)($C_4-C_8$ heterocycloalkyl), $C_1-C_4$ haloalkyl, $C_1-C_4$ haloalkoxy, nitro, cyano, —$NR_{24}R_{25}$, —$NR_{24}COR_{25}$, —$NR_{24}CO_2R_{26}$, —$COR_{24}$, —$OR_{25}$, —$CONR_{24}R_{25}$, —$CO(NOR_{22})R_{23}$, —$CO_2R_{26}$, —C=N ($OR_{22})R_{23}$, and —$S(O)_mR_{23}$; wherein said $C_1-C_{10}$ alkyl, $C_3-C_8$ cycloalkyl, ($C_1-C_4$ alkylene), ($C_3-C_8$ cycloalkyl), ($C_3-C_8$ cycloalkylene), and ($C_4-C_8$ heterocycloalkyl) groups can be optionally substituted with from one to three substituents independently selected form $C_1-C_4$ alkyl, $C_3-C_8$ cycloalkyl, ($C_1-C_4$ alkylene)($C_3-C_8$ cycloalkyl), —($C_3-C_8$ cycloalkylene)($C_3-C_8$ cycloalkyl), $C_1-C_4$ haloalkyl, hydroxy, $C_1-C_6$ alkoxy, nitro halo, cyano, —$NR_{24}R_{25}$, —$NR_{24}COR_{25}$, $NR_{24}CO_2R_{26}$, —$COR_{24}$, —$OR_{25}$, —$CONR_{24}R_{25}$, $CO_2R_{26}$, —$CO(NOR_{22})R_{25}$, and —$S(O)_mR_{23}$; and wherein two adjacent substituents of the $R_5$ group can optionally form a 5–7 membered ring, saturated or unsaturated, fused to $R^5$, which ring optionally can contain one, two, or three heterologous members independently selected from O, $S(O)_m$, and N, but not any —S—S—, —O—O—, —S—O—, or —N—S— bonds, and which ring is optionally substituted with $C_1-C_4$ alkyl, $C_3-C_8$ cycloalkyl, —($C_1-C_4$ alkylene)($C_3-C_8$ cycloalkyl), —($C_3-C_8$ cyloalkylene)($C_3-C_8$ cycloalkyl), $C_1-C_4$ haloalkyl, nitro, halo, cyano —$NR_{24}R_{25}$, $NR_{24}COR_{25}$, $NR_{24}CO_2R_{26}$, —$COR_{24}$, —$OR_{25}$, —$CONR_{24}R_{25}$, $CO_2R_{26}$, —$CO(NOR_{26})R_{25}$, or —$S(O)_mR_{23}$; wherein one of said one to four optional substituents $R_{27}$ can further be selected from —$SO_2NH(C_1-C_4$ alkyl), —$SO_2NH(C_1-C_4$ alkylene)($C_3-C_8$ cycloalkyl), —$SO_2NH(C_3-C_8$ cycloalkyl), —$SO_2NH$ ($C_3-C_8$ cycloalkylene)($C_3-C_8$ cycloalkyl), —$SO_2N(C_1-C_4$ alkyl)($C_1-C_2$ alkyl), —$SO_2NH_2$, —$NHSO_2(C_1-C_4$ alkyl), —$NHSO_2(C_3-C_8$ cycloalkyl), —$NHSO_2(C_1-C_4$ alkylene) ($C_3-C_8$ cycloalkyl), and —$NHSO_2(C_3-C_8$ cycloalkylene) ($C_3-C_8$ cycloalkyl); and wherein the alkyl, and alkylene groups of $R_5$ may independently optionally contain one double or triple bond;

$R_6$ is hydrogen, $C_1-C_6$ alkyl, $C_3-C_8$ cycloalkyl, —($C_1-C_6$ alkylene)($C_3-C_8$ cycloalkyl), or —($C_3-C_8$ cycloalkylene)

($C_3$–$C_8$ cycloalkyl), wherein said alkyl and cycloalkyl may optionally be substituted with one hydroxy, methoxy, ethoxy or fluoro group;

or, wherein the compound is a compound of formula II, $R_6$ and $R_4$ can together form an oxo (=O) group or can be connected to form a 3–8 membered carbocyclic ring, optionally containing one to three double bonds, and optionally containing one, two, or three heterologous ring members selected from O, $SO_m$, N, and $NR_{12}$, but not containing any —O—O—, —S—O—, —S—S—, or —N—S— bonds, and further optionally substituted with $C_1$–$C_4$ alkyl or $C_3$–$C_6$ cycloalkyl, wherein said $C_1$–$C_4$ alkyl substituent may optionally contain one double or triple bond;

$R_7$ is hydrogen, methyl, fluoro, chloro, bromo, iodo, cyano, hydroxy, —O($C_1$–$C_2$ alkyl) —O (cyclopropyl), —COO($C_1$–$C_2$ alkyl), —COO($C_3$–$C_8$ cycloalkyl), —$OCF_3$, $CF_3$, —$CH_2OH$, or $CH_2OCH_3$;

$R_{11}$ is hydrogen, hydroxy, fluoro, ethoxy, or methoxy;

$R_{12}$ is hydrogen or $C_1$–$C_4$ alkyl;

$R_{16}$ and $R_{17}$ are each, independently, hydrogen, hydroxy, methyl, ethyl, methoxy, or ethoxy, except that $R_{16}$ and $R_{17}$ are not both methoxy or ethoxy;

or $R_{16}$ and $R_{17}$ together form an oxo (=O) group;

or $R_{16}$ and $R_{17}$ are connected to form a 3–8 membered carbocyclic ring, optionally containing one to three double bonds, and optionally containing from one to three heterologous ring members selected from O, $SO_m$, N, and $NR_{12}$, but not containing any —O—O—, —O—, —S—S—, or —N—S— bonds, and further optionally substituted with $C_1$–$C_4$ alkyl or $C_3$–$C_6$ cycloalkyl, wherein said $C_1$–$C_4$ alkyl substituent may optionally contain one double or triple bond;

$R_{22}$ is independently at each occurrence selected from hydrogen, $C_1$–$C_4$ alkyl, $C_1$–$C_4$ haloalkyl, $C_3$–$C_6$ alkenyl, $C_3$–$C_6$ alkynyl, $C_3$–$C_8$ cycloalkyl, ($C_3$–$C_8$ cycloalkylene)($C_3$–$C_8$ cycloalkyl), and ($C_1$–$C_4$ alkylene)($C_3$–$C_8$ cycloalkyl);

$R_{23}$ is independently at each occurrence selected from $C_1$–$C_4$ alkyl, $C_1$–$C_4$ haloalkyl, $C_2$–$C_8$ alkoxyalkyl, $C_3$–$C_8$ cycloalkyl, —($C_1$–$C_4$ alkylene)($C_3$–$C_8$ cycloalkyl), —($C_3$–$C_8$ cycloalkylene)(C3–$C_8$ cycloalkyl), aryl, —($C_1$–$C_4$ alkylene)aryl, piperidine, pyrrolidine, piperazine, N-methylpiperazine, morpholine, and thiomorpholine;

$R_{24}$ and $R_{25}$ are independently at each occurrence selected from hydrogen, —$C_1$–$C_4$ alkyl, $C_1$–$C_4$ haloalkyl, especially $CF_3$, —$CHF_2$, $CF_2CF_3$, or $CH_2CF_3$, —($C_1$–$C_4$ alkylene)OH, —($C_1$–$C_4$ alkylene)—O—($C_1$–$C_4$ alkyl), —($C_1$–$C_4$ alkylene)—O—($C_3$–$C_5$ cycloalkyl), $C_3$–$C_8$ cycloalkyl, —($C_1$–$C_4$ alkylene)($C_3$–$C_8$ cycloalkyl), —($C_3$–$C_8$ cycloalkylene)($C_3$–$C_8$ cycloalkyl), —($C_4$–$C_8$ heterocycloalkyl), —($C_1$–$C_4$ alkylene)($C_4$–$C_8$ heterocycloalkyl), —($C_3$–$C_8$ cycloalkylene)($C_4$–$C_8$ heterocycloalkyl), aryl, and —($C_1$–$C_4$ alkylene)(aryl), wherein the —$C_4$–$C_8$ heterocycloalkyl groups can each independently optionally be substituted with aryl, $CH_2$-aryl, or $C_1$–$C_4$ alkyl, and can optionally contain one or two double or triple bonds; or, when $R_{24}$ and $R_{25}$ are as $NR_{24}R_{25}$, —C(O)$NR_{24}R_{25}$, —($C_1$–$C_4$ alkylene)$NR_{24}R_{25}$, or —NHCON$R_{24}R_{25}$, then $NR_{24}R_{25}$ may further optionally form a 4 to 8 membered heterocyclic ring optionally containing one or two further hetero members independently selected from $S(O)_m$, oxygen, nitrogen, and $NR_{12}$, and optionally containing from one to three double bonds;

$R_{26}$ is independently at each occurrence selected from $C_1$–$C_4$ alkyl, $C_1$–$C_4$ haloalkyl, $C_3$–$C_8$ cycloalkyl, —($C_1$–$C_4$ alkylene)($C_3$–$C_8$ cycloalkyl), —($C_3$–$C_8$ cycloalkylene) ($C_3$–$C_8$ cycloalkyl), aryl, and —($C_1$–$C_4$ alkylene)(aryl); and wherein each m is independently zero, one, or two, with the proviso that heterocycloalkyl groups of the compound of formula I, II, or III do not comprise any —S—S—, —S—O—, —N—S—, or —O—O— bonds, and do not comprise more than two oxygen or $S(O)_m$ heterologous members.

In one embodiment, the invention provides compounds of formula I or II, wherein $R_4$ is —$NHCH_2CF_3$, —$CONHNH_2$, —$CONHNHCH_3$. In another embodiment $R_4$ is —$OCF_3$ or fluoro. In another embodiment $R_4$ is —$OCHF_2$.

In another embodiment, the invention provides compounds of formula I or II, preferably formula I, wherein $R_4$ is —C(O)$NR_{24}R_{25}$ or —C(O)NHN$R_{24}R_{25}$. In a preferred embodiment, $R_4$ is —C(O)$NR_{24}R_{25}$. If $R_4$ is —C(O)$NR_{24}R_{25}$ or —C(O)NHN$R_{24}R_{25}$, then $R_{24}$ and $R_{25}$ are in a more particular embodiment selected independently from hydrogen and —$C_1$–$C_4$ alkyl. In another embodiment, $R_4$ is —C(O)$NH_2$ or —C(O)$NHCH_3$. In another embodiment, $R_4$ is —C(O)N($CH_3$)$_2$.

In another more particular embodiment, the invention provides a compound of formula I, or II, preferably I, as defined above, wherein $R_4$ is —C(O)$NHCH_2$($C_3$–$C_5$ cycloalkyl), —C(O)NH($C_3$–$C_5$ cycloalkyl), —C(O)N ($C_3$–$C_5$ cycloalkyl)$_2$, —C(O)$NR_{24}R_{25}$ wherein $R_{24}$ and $R_{25}$ form a 4, 5, or 6 membered heterocyclic ring, —C(O)NH ($C_4$–$C_8$ heterocycloalkyl), or —C(O)NH($CH_2$($C_4$–$C_8$ heterocycloalkyl)).

In another embodiment, the invention provides a compound of formula I or II, preferably formula I, wherein $R_4$ is —($C_1$–$C_4$ alkylene)$NR_{24}R_{25}$. If $R_4$ is —($C_1$–$C_4$ alkylene) $NR_{24}R_{25}$, then $R_{24}$ and $R_{25}$ are in a more particular embodiment selected independently from hydrogen, —$C_1$–$C_4$ alkyl, —($C_1$–$C_4$ alkylene)($C_3$–$C_8$ cycloalkyl), and $C_3$–$C_8$ cycloalkyl.

In another embodiment, the invention provides a compound of formula I or II as defined above, wherein $R_4$ is —$OCH_2$($C_3$–$C_5$ cycloalkyl), —O—($C_3$–$C_5$ cycloalkyl), —$SCH_2$($C_3$–$C_5$ cycloalkyl), or —S($C_3$–$C_5$ cycloalkyl).

In another embodiments of the invention, a compound of formula I or II, preferably I, as defined above, is provided, wherein $R_4$ is —$COOCH_3$. In another embodiment of the invention, a compound of formula I or II, preferably I, is provided wherein $R_4$ is —$COOCH_2CH_3$.

Another embodiment of the invention provides compounds of formula I or II, preferably I, as defined above, wherein $R_4$ is —$OCH_3$. In another embodiment of the invention, compounds of formula I or II are provided, wherein $R_4$ is —$CH_3$. In another embodiment, $R_4$ is —$CH_2CH_3$. In another embodiment $R_4$ is chloro. In another embodiment, $R_4$ is bromo.

In another embodiment, a compound of formula I or II, preferably I, is provided, wherein $R_4$ is —$CF_3$.

In another embodiment, a compound of formula I or II, preferably I, is provided, wherein $R_4$ is —$CH_2OH$.

In another embodiment, a compound of formula I or II, preferably I, is provided, wherein $R_4$ is —$CH_2OCH_3$.

In another embodiment, a compound of formula I or II, preferably I, is provided, wherein $R_4$ is —$CH_2OCF_3$.

In another embodiment of the invention, the compound of formula I or II, preferably I, is as defined above, and $R_4$ is —$SCH_3$.

In another embodiment, a compound of formula I or II, preferably I, is provided, wherein $R_4$ is —S(O)$CH_3$.

In another embodiment, a compound of formula I or II, preferably I, is provided, wherein $R_4$ is —S(O)$_2$CH$_3$.

In another embodiment, a compound of formula I or II, preferably I, is provided, wherein $R_4$ is —C(O)CH$_3$.

In another embodiment, a compound of formula I or II, preferably I, is provided, wherein $R_4$ is —NR$_{24}$R$_{25}$. Preferably, $R_{24}$ and $R_{25}$ are —C$_1$–C$_4$ alkyl or hydrogen. In a more particular embodiment, $R_4$ is —NH$_2$, —NHCH$_3$, or —N(CH$_3$)$_2$.

In another embodiment, a compound of formula I or II, preferably I, is provided, wherein $R_4$ is —NO$_2$.

In another embodiment, a compound of formula I or II, preferably I, is provided, wherein $R_4$ is —CH(OH)CH$_3$.

In another embodiment, a compound of formula I or II, preferably I, is provided, wherein $R_4$ is —CN.

In another embodiment, the invention provides compounds of formula I, II, or III as defined above, wherein B is —NR$_1$R$_2$, or —NHCHR$_1$R$_2$. If B is —NR$_1$R$_2$, R$_1$ is preferably C$_1$–C$_6$ alkyl, C$_3$–C$_8$ cycloalkyl, or —(C$_1$–C$_6$ alkylene)(C$_3$–C$_8$ cycloalkyl), more preferably —(C$_1$–C$_6$ alkylene)(C$_3$–C$_8$ cycloalkyl), and R$_2$ is preferably C$_1$–C$_{12}$ alkyl optionally containing from one to three double or triple bonds and optionally substituted with from one three fluoro atoms. Preferably, B is —N(CH$_2$-cyclopropyl)(CH$_2$CH$_3$) or —N(CH$_2$-cyclopropyl)(CH$_2$CF$_3$).

If B is —NHCHR$_1$R$_2$, then R$_1$ is preferably —C(O)H, —C(O)(C$_1$–C$_6$ alkyl), or —C$_1$–C$_6$ alkyl, wherein said C$_1$–C$_6$ alkyl is optionally substituted with from one to six fluoro atoms or one or two R$_8$ independently selected from —C$_1$–C$_4$ alkyl, hydroxy and —O—(C$_1$–C$_6$ alkyl), and R$_2$ is preferably —C$_1$–C$_{12}$ alkyl optionally containing from one to three double or triple bonds and optionally substituted with from one three substituents selected from fluoro and C$_1$–C$_6$ alkyl. Preferably, if B is —NHCHR$_1$R$_2$, then R$_1$ is independently selected from —CH$_2$CH$_3$ and —CF$_2$CH$_3$, and R$_2$ is independently selected from —CH$_2$CH$_3$, —CF$_2$CH$_3$, —CH(OH)CH$_3$, —CH(OCH$_3$)CH$_3$, —C(OH)(CH$_3$)$_2$, and —C(O)CH$_3$. Preferably B is —NHCH(CH$_2$CH$_3$)$_2$, —NHCH(CH$_2$CH$_3$)(CF$_2$CH$_3$), —NHCH(CF$_2$CH$_3$)$_2$, —NHCH(CH(OH)CH$_3$)(CF$_2$CH$_3$), —NHCH(CH(OH)CH$_3$)(CH$_2$CH$_3$), —NHCH(CH(OCH$_3$)CH$_3$)(CH$_2$CH$_3$), —NHCH(C(O)CH$_3$)(CH$_2$CH$_3$), —NHCH(C(O)CH$_3$)(CF$_2$CH$_3$), —NHCH(C(OH)(CH$_3$)$_2$)(CH$_2$CH$_3$), or —NHCH(C(OH)(CH$_3$)$_2$)(CF$_2$CH$_3$).

are preferably, B is —N(CH$_2$-cyclopropyl)(CH$_2$CH$_3$), —NHCH(CH$_2$CH$_3$)$_2$, —NHCH(CH(OH)CH$_3$)(CF$_2$CH$_3$), —NHCH(CH(OH)CH$_3$)(CH$_2$CH$_3$), —NHCH(CH(OCH$_3$)CH$_3$)(CH$_2$CH$_3$), —NHCH(C(O)CH$_3$)(CH$_2$CH$_3$), or —NHCH(C(OH)(CH$_3$)$_2$)(CH$_2$CH$_3$).

In another embodiment of the invention, B is selected from —OCHR$_1$R$_2$, SCHR$_1$R$_2$, —CHR$_1$NHR$_2$, —CHR$_1$N(CH$_3$)R$_2$, —CHR$_2$OR$_1$, and —CHR$_1$OR$_2$.

In another embodiment of the invention, a compound of formula I, II, or III as defined above is provided, wherein $R_3$ is methyl, ethyl, O—CH$_3$, —OCF$_3$, Cl, S—CH$_3$, or CF$_3$. Preferably $R_3$ is methyl.

In another embodiment of the invention, a compound of formula III as defined above is provided wherein the dashed line in C$_{---}$N(R$_6$) represents a double bond, and the dashed line in C$_{---}$G does not represent a double bond, and C$_{---}$G is CH$_2$, C(H)(CH$_3$), or C(H)(CH$_2$CH$_3$).

In another embodiment of the invention, a compound of formula III is provided, wherein the dashed line in C$_{---}$G represents a double bond, and C$_{---}$G is C=O, C=S, or C=NH, and C$_{---}$N(R$_6$) is C—NH or C—N(C$_1$–C$_4$ alkyl).

In another embodiment of the invention, a compound of formula II as defined above is provided, wherein CR$_{16}$R$_{17}$ and CR$_4$R$_6$ are each independently selected from —C=O, —CH$_2$, —CH(C$_1$–C$_4$ alkyl), —C(C$_1$–C$_2$ alkyl)$_2$, cyclopropyl, —CHOH, —CHOCH$_3$, —C(OCH$_2$CH$_2$), and —C(CH$_2$OCH$_2$).

In another embodiment, a compound of formula II is provided, wherein CR$_{16}$R$_{17}$ is selected from —CH$_2$, —CH(C$_1$–C$_4$ alkyl), —C(C$_1$–C$_2$ alkyl)$_2$, cyclopropyl, —CHOH, and —CHOCH$_3$, and CR$_4$R$_6$ is C=O, CH$_2$, CH(C$_1$–C$_2$ alkyl), or —CHOCH$_3$.

In another embodiment of the invention, a compound of formula I, II, or III as defined above is provided, wherein $R_5$ is optionally substituted aryl or heteroaryl selected from optionally substituted phenyl, thiazolyl, naphthyl, thienyl, benzothienyl, pyridyl, quinolyl, quinazolinyl, quinoxalinyl, pyrazinyl, pyrimidinyl, indazolyl, imidazolyl, furanyl, benzimidazolyl, benzofuranyl, benzothiazolyl, benzisoxazolyl, isothiazolyl, pyrazolyl, pyrrolyl, indolyl, pyrrolopyridyl, oxazolyl, benzoxazolyl, benzothiadiazolyl, pyridyl, benzo[1,3]dioxolyl, and 2,3-dihydro-benzo[1,4]dioxinyl.

In another embodiment, $R_5$ is substituted with from one to four $R_{27}$ selected independently from C$_1$–C$_4$ alkyl, —O—(C$_1$–C$_4$ alkyl), chloro, bromo, —CH(CH$_3$)(OH), —C(CH$_3$)$_2$(OH), —CH(CH$_3$)(OCH$_3$), —C(CH$_3$)$_2$(OCH$_3$), OCF$_3$, OCHF$_2$, —O-cyclopropyl, —(—CH$_2$-cyclopropyl, —CH(CF$_3$)(OH), —CH(CF$_3$)(OCH$_3$), —C(=O)(CF$_3$), -2-cyclopropyl-1-OH, 1-cyclopropyl-2-OH, 1-cyclopropyl-1-NH$_2$, —O-oxetanyl, —O-tetrahydrofuranyl, cyclopropyl, and —SCH$_3$.

In another embodiment of the invention, a compound of formula I, II, or III as defined above is provided, wherein $R_5$ is phenyl, pyridyl or pyrimidyl, substituted with two or three $R_{27}$ groups. In a more particular embodiment, $R_5$ is phenyl, substituted with two or three $R_{27}$ groups.

In another embodiment, a compound of formula I, II or III, preferably I, as defined above is provided, wherein $R_5$ is phenyl, pyridyl or pyrimidyl, substituted with two or three $R_{27}$ groups selected from halo, —(C$_1$–C$_4$ haloalkyl), —C(O)R$_{24}$, —OR$_{25}$, —C(O)NR$_{24}$R$_{25}$, and C$_1$–C$_{10}$ alkyl which is optionally substituted with one to three substituents, preferably one substituent, selected from hydroxy, C$_1$–C$_6$ alkoxy, and —NR$_{24}$R$_{25}$. Preferably, each $R_{27}$ is independently selected from methyl, ethyl, —CF$_3$, —OCH$_3$, —OCF$_3$, —C(O)NH$_2$, —C(O)NHCH$_3$, —C(O)CF$_3$, —C(O)CH$_3$, —CH(OH)CH$_3$, chloro, bromo, fluoro, —OCH$_2$CH$_3$, —O-cyclopropyl, —CH$_2$NH$_2$, —CH$_2$NHCH$_3$, —CH$_2$N(CH$_3$)$_2$, —CH$_2$OCH$_3$, and —CH(OCH$_3$)CH$_3$. More preferably, each $R_{27}$ is independently selected from methyl, ethyl, —CF$_3$, —OCH$_3$, —OCF$_3$, —C(O)NH$_2$, —C(O)NHCH$_3$, chloro, bromo, and fluoro.

In another embodiment, a compound of formula I, II or III, preferably I, is provided, wherein — is phenyl and is substituted with two or three substituents $R_{27}$ independently selected from methyl, chloro, —OCH$_3$, —OCF$_3$, bromo, and —C(O)NH$_2$.

In another embodiment of the invention, a compound of formula I as defined above is provided, wherein Z is O, NH, or NC(=O)CF$_3$. Preferably Z is O.

In a preferred embodiment of the invention, a compound of formula I is provided, wherein Z is O; B is —NHCHR$_1$R$_2$, wherein R$_1$ is preferably —C(O)H, —C(O)(C$_1$–C$_6$ alkyl), or —C$_1$–C$_6$ alkyl, wherein said C$_1$–C$_6$ alkyl is optionally substituted with from one to six fluoro atoms or one or two R$_8$ independently selected from —C$_1$–C$_4$ alkyl, hydroxy and ——($C_1$–$C_6$ alkyl), and wherein $R_2$ is preferably —$C_1$–$C_{12}$ alkyl optionally containing from one to three double or triple bonds and optionally substituted with from one three substituents selected from fluoro and $C_1$–$C_8$ alkyl; $R_5$ is $R_5$ is phenyl, pyridyl or pyrimidyl, substituted with two or three $R_{27}$ groups selected from halo, —($C_1$–$C_4$ haloalkyl), —C(O)$R_{24}$, —O$R_{25}$, —C(O)N$R_{24}R_{25}$, and $C_1$–$C_{10}$ alkyl which is optionally substituted with one to three substituents, preferably one substituent, selected from hydroxy, $C_1$–$C_6$ alkoxy, and —N$R_{24}R_{25}$; and $R_4$ is —C(O) N$R_{24}R_{25}$. $R_{24}$ and $R_{25}$ of —C(O)N$R_{24}R_{25}$ are in a more particular embodiment selected independently from hydrogen and —$C_1$–$C_4$ alkyl.

In another preferred embodiment of the invention, a compound of formula I is provided, wherein Z is O; B is —NHCH$R_1R_2$, wherein $R_1$ of —NHCH$R_1R_2$ is preferably —C(O)H, —C(O)($C_1$–$C_6$ alkyl), or —$C_1$–$C_6$ alkyl, wherein said $C_1$–$C_6$ alkyl is optionally substituted with from one to six fluoro atoms or one or two $R_8$ independently selected from —$C_1$–$C_4$ alkyl, hydroxy and —O—($C_1$–$C_6$ alkyl), and wherein $R_2$ of —NHCH$R_1R_2$ is preferably —$C_1$–$C_{12}$ alkyl optionally containing from one to three double or triple bonds and optionally substituted with from one three substituents selected from fluoro and $C_1$–$C_6$ alkyl; $R_5$ is $R_5$ is phenyl, pyridyl or pyrimidyl, substituted with two or three $R_{27}$ groups selected from halo, —($C_1$–$C_4$ haloalkyl), —C(O) $R_{24}$, —O$R_{25}$, —C(O)N$R_{24}R_{25}$, and $C_1$–$C_{10}$ alkyl which is optionally substituted with one to three substituents, preferably one substituent, selected from hydroxy, $C_1$–$C_6$ alkoxy, and —N$R_{24}R_{25}$; and $R_4$ is —N$R_1R_2$, wherein $R_1$ of —N$R_1R_2$ is preferably $C_1$–$C_6$ alkyl, $C_3$–$C_8$ cycloalkyl, or —($C_1$–$C_6$ alkylene)($C_3$–$C_8$ cycloalkyl), more preferably —($C_1$–$C_6$ alkylene)($C_3$–$C_8$ cycloalkyl), and $R_2$ of —N$R_1R_2$ is preferably $C_1$–$C_{12}$ alkyl optionally containing from one to three double or triple bonds and optionally substituted with from one three fluoro atoms. Preferably, B is —N(CH$_2$-cyclopropyl)(CH$_2$CH$_3$) or —N(CH$_2$-cyclopropyl)(CH$_2$CF$_3$).

Examples of preferred compounds of this invention are:

2-(4-Chloro-2,6-dimethyl-phenoxy)-4-(1-hydroxymethyl-propylamino)-6,N-dimethyl-nicotinamide;

2-(4-Chloro-2,6-dimethyl-phenoxy)-4-(1-methoxymethyl-propylamino)-6,N-dimethyl-nicotinamide;

2-(4-Chloro-2,6-dimethyl-phenoxy)-4-(1-methoxymethyl-propylamino)-6-methyl-nicotinamide;

2-(4-Bromo-2-methoxy-phenoxy)-4-(1-ethyl-propylamino)-6-methyl-nicotinamide;

2-(4-Chloro-2,6-dimethyl-phenoxy)-4-(1-ethyl-2-methoxy-propylamino)-6-methyl-nicotinamide;

2-(4-Chloro-2,6-dimethyl-phenoxy)-4-(1-ethyl-2-methoxy-propylamino)-6,N-dimethyl-nicotinamide;

2-(4-Chloro-2-trifluoromethoxy-phenoxy)-4-(1-ethyl-propylamino)-6-methyl-nicotinamide;

2-(4-Chloro-2-trifluoromethoxy-phenoxy)-4-(1-ethyl-propylamino)-6-N-dimethyl-nicotinamide;

2-(4-Chloro-2,6-dimethyl-phenoxy)-4-(1S,2R-1-ethyl-2-methoxy-propylamino)-6,N-dimethyl-nicotinamide; and 2-(4-Chloro-2,6-dimethyl-phenoxy)-4-(1S,2S-1-ethyl-2-methoxy-propylamino)-6,N-dimethyl-nicotinamide;

and pharmaceutically acceptable salts thereof.

Other examples of preferred compounds of the invention are:

2-(4-Bromo-2-methoxy-phenoxy)-4-(1-ethyl-propylamino)-6-methyl-nicotinonitrile;

4-[4-(1-Ethyl-propoxy)-3,6-dimethyl-pyridin-2-yloxy]-3,5-dimethyl-benzamide;

2-(4-Chloro-2,6-dimethyl-phenoxy)-6-methyl-4-(1-methylsulfanylmethyl-propylamino)-nicotinic acid methyl ester;

2-(4-Chloro-2,6-dimethyl-phenoxy)-4-(1-hydroxymethyl-propylamino)-6-methyl-nicotinic acid methyl ester;

2-(4-Bromo-2,6-dimethyl-phenoxy)-4-(1-ethyl-propylamino)-6-methyl-nicotinonitrile;

2-(4-Chloro-2-trifluoromethoxy-phenoxy)-4-(1-ethyl-propylamino)-6-methyl-nicotinic acid methyl ester; and 2-(4-Chloro-2,6-dimethyl-phenoxy)-6-methyl-4-(tetrahydro-furan-3-ylamino)-nicotinic acid methyl ester;

and pharmaceutically acceptable salts thereof.

Other examples of compounds of the invention are:

2-(4-bromo-2-methyl-phenylamino)-4-(1-ethyl-propoxy)-6-methyl-nicotinic acid;

[2-(4-bromo-2-methyl-phenylamino)4-(1-ethyl-propoxy)-6-methyl-pyridin-3-yl]-methanol;

2-(4-chloro-2,6-dimethyl-phenoxy)-4-(1-hydroxymethyl-propylamino)-6-methyl-nicotinic acid;

2-(4-chloro-2,6-dimethyl-phenoxy)-4-(1-hydroxymethyl-propylamino)-6-methyl-nicotinamide;

2-(4-chloro-2,6-dimethyl-phenoxy)-N-ethyl-4-(1-hydroxymethyl-propylamino)-6-methyl-nicotinamide;

2-(4-chloro-2,6-dimethyl-phenoxy)-4-(1-hydroxymethyl-propylamino)-6, N-dimethyl-nicotinamide;

cyclopropylmethyl-[2,5,6-trimethyl-7-(2,4,6-trimethyl-phenyl)-7H-pyrrolo[2,3-d]pyrimidin-4-yl]-amine;

cyclopropylmethyl-[3,6-dimethyl-2-(2,4,6-trimethyl-phenoxy)-pyridin-4-yl]-ethyl-amine;

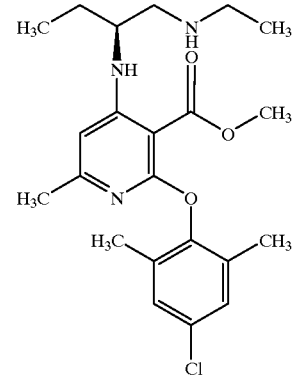

2-(4-chloro-2,6-dimethyl-phenoxy)-4-(1-methoxycarbonyl-propylamino)-6-methyl-nicotinic acid methyl ester;

2-(4-chloro-2,6-dimethyl-phenoxy)-4-(1-methoxycarbonyl-propylamino)-6-methyl-nicotinic acid methyl ester;

3,3',6'-trimethyl-2'-(2,4,6-trimethyl-phenoxy)-3,4,5,6-tetrahydro-2H-[1,4']bipyridinyl;

2-(4-chloro-2,6-dimethyl-phenoxy)-6,N-dimethyl-4-(S)-(tetrahydro-furan-3-ylamino)-nicotinamide;

[7-(4-bromo-2,6-dimethyl-phenyl)-2,5-dimethyl-7H-pyrrolo[2,3-d]pyrimidin-4-yl]-(tetrahydro-furan-3-yl)-amine;

2,5,6-trimethyl-4-pyrrolidin-1-yl-7-(2,4,6-trimethyl-phenyl)-7H-pyrrolo[2,3-d]pyrimidine;

(2-pyrrolidin-1-yl-ethyl)-[2,5,6-trimethyl-7-(2,4,6-trimethyl-phenyl)-7H-pyrrolo[2,3-d]pyrimidin-4-yl]-amine;

(tetrahydro-furan-3-yl)-[2,5,6-trimethyl-7-(2,4,6-trimethyl-phenyl)-7H-pyrrolo[2,3-d]pyrimidin-4-yl]-amine;

2-(4-chloro-2,6-dimethyl-phenoxy)-6-methyl-4-(tetrahydro-furan-3-ylamino)-pyridine -3-carbaldehyde oxime;

[3,6-dimethyl-2-(2,4,6-trimethyl-phenoxy)-pyridin-4-yl]-(2-pyrrolidin-1-yl-ethyl)-amine;

N-[3,6-dimethyl-2-(2,4,6-trimethyl-phenoxy)-pyridin-4-yl]-2,2,2-trifluoro-N-(2-pyrrolidin-1-yl-ethyl)-acetamide;

N2-[3,6-dimethyl-2-(2,4,6-trimethyl-phenoxy)-pyridin-4-yl]-N1,N1-dimethyl-butane-1,2-diamine;

2-(4-chloro-2,6-dimethyl-phenoxy)-4-(1-ethyl-2-methylamino-propylamino)-6-methyl-nicotinic acid methyl ester;

[3,6-dimethyl-2-(2,4,6-trimethyl-phenoxy)-pyridin-4-yl]-(3-methyl-butyl)-(2-pyrrolidin-1-yl-ethyl)-amine;

(3,3-dimethyl-butyl)-[3,6-dimethyl-2-(2,4,6-trimethyl-phenoxy)-pyridin-4-yl]-(2-pyrrolidin-1-yl-ethyl)-amine;

[3,6-dimethyl-2-(2,4,6-trimethyl-phenoxy)-pyridin-4-yl]-morpholin-4-yl-amine;

4-(1-ethyl-propoxy)-2-(4-methoxy-2-methyl-phenylamino)-6-methyl-nicotinic acid;

2-(4-chloro-2-methyl-phenylamino)-4-(1-ethyl-propoxy)-6-methyl-nicotinic acid;

4-(1-ethyl-propylamino)-6-methyl-2-(2,4,6-trimethyl-pyridin-3-yloxy)-nicotinic acid;

N2-[3,6-dimethyl-2-(2,4,6-trimethyl-phenoxy)-pyridin4-yl]-N1-pyridin-3-ylmethyl-butane-1,2-diamine;

N2-[3,6-dimethyl-2-(2,4 ,6-trimethyl-phenoxy)-pyridin-4-yl]-N1-thiazol-2-ylmethyl-butane-1,2-diamine;

2-(2,4-dimethyl-phenylamino)-4-(1-ethyl-propoxy)-6-methyl-nicotinic acid;

[2-(4-chloro-2-methyl-phenylamino)-4-(1-ethyl-propoxy)-6-methyl-pyridin-3-yl]-methanol;

2-(4-chloro-2,6-dimethyl-phenoxy)-4-(1-hydroxymethyl-propylamino)-6-methyl-nicotinonitrile;

1-(4-chloro-2-methyl-phenyl)-5-(1-ethyl-propoxy)-7-methyl-1,4-dihydro-2H-3-oxa-1,8-diaza-naphthalene;

4-(1-ethyl-propylamino)-2-methyl-7-(2,4,6-trimethyl-phenyl)-7H-pyrrolo[2,3-d]pyrimidine-5,6-dione;

4-(1-ethyl-propylamino)-2-methyl-7-(2,4,6-trimethyl-phenyl)-5,7-dihydro-pyrrolo[2,3-d]pyrimidin-6-one;

4-[3-cyano-4-(1-ethyl-propylamino)-6-methyl-pyridin-2-yloxy]-3-methoxy-benzoic acid;

2-(4-chloro-2,6-dimethyl-phenoxy)-4-(1-methoxymethyl-propylamino)-6-methyl-nicotinamide;

2-(4-chloro-2,6-dimethyl-phenoxy)-4-(1-methoxymethyl-propylamino)-6,N-dimethyl-nicotinamide;

2-(4-chloro-2,6-dimethyl-phenoxy)-N-(1-hydroxymethyl-propyl)-4-(1-hydroxymethyl-propylamino)-6-methyl-nicotinamide;

and pharmaceutically acceptable salts of the above compounds.

The invention also relates to a pharmaceutical composition for the treatment of (a) a disorder or condition the treatment of which can be effected or facilitated by antagonizing CRF, including but not limited to disorders induced or facilitated by CRF, or (b) a disorder or condition selected from inflammatory disorders such as rheumatoid arthritis and osteoarthritis, pain, asthma, psoriasis and allergies; generalized anxiety disorder; panic; phobias, including social phobia, agoraphobia, and specific phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies or addictions, including dependencies or addictions to alcohol, cocaine, heroin, benzodiazapines, or other drugs; drug or alcohol withdrawal symptoms; stress-induced psychotic episodes; euthyroid sick syndrome; syndrome of inappropriate antidiuretic hormone; obesity; infertility; head trauma; spinal cord trauma; ischemic neuronal damage, including cerebral ischemia, for example cerebral hippocampal ischemia; excitotoxic neuronal damage; epilepsy; stroke; immune dysfunctions including stress induced immune dysfunctions, including porcine stress syndrome, bovine shipping fever, equine paroxysmal fibrillation, confinement dysfunction in chicken, sheering stress in sheep, and human-animal interaction stress in dogs; muscular spasms; urinary incontinence; senile dementia of the Alzheimer's type; multiinfarct dementia; amyotrophic lateral sclerosis; hypertension; tachycardia; congestive heart failure; osteoporosis; premature birth; hypoglycemia, and Syndrome X in a mammal, including a human, or bird comprising an amount of a compound of the formula I, II or III, or a pharmaceutically acceptable salt thereof, that is effective in the treatment of such disorder or condition, and a pharmaceutically acceptable carrier.

The invention further includes a method for the treatment of (a) a disorder or condition the treatment of which can be effected or facilitated by antagonizing CRF, including but not limited to disorders induced or facilitated by CRF, or (b) a disorder or condition selected from inflammatory disorders such as rheumatoid arthritis and osteoarthritis, pain, asthma, psoriasis and allergies; generalized anxiety disorder; panic; phobias, including social phobia, agoraphobia, and specific phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies or addictions, including dependencies or addictions to alcohol, cocaine, heroin, benzodiazapines, or other drugs; drug or alcohol withdrawal symptoms; stress-induced psychotic episodes; euthyroid sick syndrome; syndrome of inappropriate antidiuretic hormone; obesity; infertility; head trauma; spinal cord trauma; ischemic neuronal damage, including cerebral ischemia, for example cerebral hippocampal ischemia; excitotoxic neuronal damage; epilepsy; stroke; immune dysfunctions including stress induced immune dysfunctions, including porcine stress syndrome, bovine shipping fever, equine paroxysmal fibrillation, confinement dysfunction in chicken, sheering stress in sheep, and human-animal interaction stress in dogs; muscular spasms; urinary incontinence; senile dementia of the Alzheimer's type; multiinfarct dementia; amyotrophic lateral sclerosis; hypertension; tachycardia; congestive heart failure; osteoporosis; premature birth; hypoglycemia, and Syndrome X in a mammal, including a human, or bird comprising administering to a subject in need of said treatment an amount of a compound of the formula I, II or III or a pharmaceutically acceptable salt thereof, that is effective in treating such disorder or condition.

The present invention also provides a pharmaceutical composition for and a method of treating a condition comprising administering a compound of I, II, or III, in an amount effective to treat said condition, wherein said condition is selected from the group consisting of: a) abnormal circadian rhythm; b) depression, further wherein a second compound for treating depression is administered, said second compound for treating depression having an onset of action that is delayed with respect to that of said CRF antagonist; and c) emesis. The aforementioned method can practiced according to the information provided in U.S. Provisional Patent Application No. 60/151,183, filed Aug. 27, 1999, which describes treatment of the aforementioned conditions using CRF antagonists in general and which is incorporated herein by reference in its entirety.

The compounds of formula I, II, and III, described herein can also be used to treat forms of heart failure described in U.S. Ser. No. 09/248,073, supra, and can be made into pharmaceutical compositions therefore.

Examples of more specific forms or manifestations of abnormal circadian rhythm that can be treated according to the present invention include, but are not limited to, time zone change syndrome resulting, seasonal affective disorder, shift-work sleep disorder, irregular sleep-wake pattern, delayed sleep phase syndrome resulting from said abnormal circadian rhythm, advanced sleep phase syndrome, or non-24 hour sleep wake disorder resulting from said abnormal circadian rhythm. Moreover, the compound of formula I, II, or III can be combined in the method or pharmaceutical composition for treatment of abnormal circadian rhythm with a second compound that is useful for treating a sleep disorder, for example tachykinin antagonists, agonists for GABA brain receptors, metalonergic compounds, GABA brain receptor agonists, $5HT_2$ receptor antagonists, and D4 receptor binding compounds. However, other compounds or substances useful for treating a sleep disorder can be combined with a compound of formula I, II, or III. Such methods and compositions are described in greater detail in U.S. Provisional Patent Application No. 60/151,183, supra.

In another embodiment, said condition is depression, and the second compound having delayed action for treating depression is selected from the group consisting of selective serotonin reuptake inhibitors, tricyclic antidepressants, norepinephrine uptake inhibitors, lithium, bupropion, sertraline, fluoxetine, trazodone, and a tricyclic antidepressant selected from the group consisting of imipramine, amitriptyline, trimipramine, doxepin, desipramine, nortriptyline, protriptyline, amoxapine, clomipramine, maprotiline, and carbamazepine, and pharmaceutically acceptable salts and esters of the above-recited compounds.

In another embodiment, the condition being treated is emesis, and the method further comprises administering a second compound for treating emesis. The second compound for treating emesis can be selected from, but is not limited to, tachykinin antagonists, 5HT3 antagonists, GABA agonists, and substance P inhibitors. More specific categories of emesis encompassed in the present invention include emesis induced by a condition or agent selected from the group consisting of pregnancy, vestibular disorder, postoperative sickness, gastrointestinal obstruction, reduced gastrointestinal motility, visceral pain, migraine, change in intercranial pressure, chemotherapy, radiation, toxins, and opioid analgesics.

DETAILED DESCRIPTION OF THE INVENTION

Methods of preparing the compounds and compositions of this invention are described below. In the discussion and reaction schemes that follow, $R_1$ through $R_9$, $R_{11}$, $R_{12}$, $R_{16}$, $R_{17}$, $R_{19}$, A, B, G, the dashed lines and structural formulae I, II, III, X, XI, XII and IV, unless otherwise indicated, are defined as above.

Whenever reference is made herein to alkyl, both straight and branched chain alkyl groups are encompassed. For example, "$C_1$–$C_6$ alkyl" encompasses both straight and branched chain alkyl groups of one to six carbon atoms, including (but not limited to) methyl, ethyl, isopropyl, t-butyl and hexyl.

Whenever $R_2$ or $R_5$ is a heterocyclic group, attachment of the group is through a carbon atom.

Whenever reference is made herein to $C_1$–$C_4$ alkyl or $C_1$–$C_6$ alkyl which "may contain one double or triple bond" in the above definitions, it is understood that at least two carbons are present in the alkyl for one double or triple bond.

Whenever reference is made herein to halo or halogen; fluoro, chloro, bromo or iodio is meant unless indicated otherwise.

The terms "treatment", "treating", and the like, are meant to include both slowing or reversing the progression of a disorder, as well as curing the disorder. These terms also include alleviating or reducing the symptoms of a disorder or condition, even if the disorder or condition is not actually eliminated and even if progression of the disorder or condition is not itself slowed or reversed. The term "treatment" and like terms also include prophylactic treatment of disorders and conditions.

The term "haloalkyl" refers to an alkyl group substituted by one or more halogen atoms, i.e. one or more fluoro, bromo, iodo, or chloro atoms. Moreover, it is understood that when an alkyl group can be, according to this specification and claims, substituted with, e.g., one to nine, e.g., nine atoms, that the optional one to nine fluorine atoms are only an option when a sufficient number of carbon atoms is present in the alkyl group.

The term "aryl" in the definitions above means, unless otherwise indicated, an organic radical derived from an aromatic hydrocarbon by removal of one hydrogen atom. Examples of aryl groups are phenyl and naphthyl.

The term "heterocycloalkyl", unless otherwise specified means a 4 to 8 membered mono-carbocyclic ring or bicyclic ring, wherein at least one carbon atom is replaced with a hetero member selected from oxygen, nitrogen, N-(alkyl), or $S(O)_m$, wherein m is zero, 1, 2, or 3. Generally, heterocycloalkyl groups comprise up to four hetero members, preferably 1, 2, or 3 hetero members. Heterocycloalkyl groups of the compounds of the invention can contain optionally from one to three double bonds. The term "heterocycloalkyl" also includes heteroaryl groups. Examples of heteroaryl groups include thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl. Other examples of aryl groups are pyrazolyl, triazolyl, tetrazolyl, isoxazolyl, oxazolyl, pyrrolyl, isoquinolinyl, cinnolinyl, indazolyl, indolizinyl, phthalazinyl, pyridazinyl, triazinyl, isoindolyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Preferred heteroaryl groups are thiazolyl, thienyl, benzothienyl, pyridyl, quinolyl, quinazolinyl, quinoxalinyl, pyrazinyl, pyrimidinyl, indazolyl, imidazolyl, furanyl, benzimidazolyl, benzofuranyl, benzothiazolyl, benzisoxazolyl, isothiazolyl, pyrazolyl, pyrrolyl, indolyl, pyrrolopyridyl, oxazolyl, benzoxazolyl, and benzothiadiazolyl. Other preferred heterocycloalkyl groups are tetrahydrofurano, tetrahydropyrano, morpholino, pyrrolidino, piperidino, piperazino, [2,2,1]-azabicyclic rings, [2,2,2]-azabicyclic rings, [3,3,1]azabicyclic rings, quinuclidino, azetidino, azetidinono, oxindolo, dihydroimidazolo, and pyrrolidinono. Heterocyclolalkyl groups in the compounds of the invention may be C-attached or N-attached where such is possible.

Compounds of the formula I wherein B is —$NR_1R_2$, —$NHCHR_1R_2$, —$OCHR_1R_2$ or —$SCHR_1R_2$, and $R_3$ is methyl, ethyl or chloro (hereinafter $R_{19}$) may be prepared by reaction of a compound of the formula IV wherein D is Cl, and A, $R_4$, $R_5$, and Z are as defined above with reference to formula I, with a compound of the formula BH wherein B is as defined immediately above. The reaction is carried out in a solvent in the presence of a base at a temperature of between about 0° to about 230° C. Suitable solvents are organic solvents such as tetrahydrofuran (THF), acetonitrile, dimethylsulfoxide (DMSO), acetone, $C_2$–$C_{15}$ alkyl alcohol, chloroform ($CHCl_3$), benzene, xylene, toluene, sulfolane, pyridine, quinoline, 2,4,6-trimethylpyridine, acetamide, di-($C_1$–$C_2$)alkylacetamide or 1-methyl-2-pyrrolidinone.

A preferred method of preparing compounds of the formula I wherein A is —$CR_7$ and B is —$NR_1R_2$ or —$NHCHR_1R_2$ is the two step procedure described below. First, a compound of the formula IV is reacted with an excess of $R_1NH_2$ or $NH_3$ or an equivalent $NH_3$ precursor (e.g., $NaN_3$, $nBu_4N^+N_3$— or $NH_2OH$) at temperature from about 75° C. to about 250° C. and at a pressure from about 0 to about 300 psi, in an appropriate solvent, as described above, to form a compound of the formula I wherein B is —$NHR_1$, —$NH_2$, —$NH_2OH$ or —$N_3$. Compounds of the formula I wherein B is —$N_3$ or —$NH_2OH$ can be converted into the corresponding compounds of formula I wherein B is —$NH_2$ by methods well known in the art such as hydrogenation or reduction. Alkylation of a compound of the formula I wherein B is —$NHR_1$ or —$NH_2$ with an appropriate alkyl halide in the presence of an appropriate base such as lithium or sodium bistrimethylsilylamide, lithium or sodium diisopropylamide, n-butyllithium or potassium t-butoxide, in an appropriate solvent such as THF, dioxane or methylene chloride, will yield the corresponding compound of formula I wherein B is —$NR_1R_2$. Alternatively, reductive amination of a compound of the formula I wherein B is —$NHR_1$, or —$NH_2$, for example, acylation, followed by reduction with a borohydride (e.g., sodium borohydride) will form the corresponding compound of formula I wherein B is —$NR_1R_2$ or $NHCHR_1R_2$.

When B is —$NR_1R_2$ or —$NHCHR_1R_2$, an excess of BH may be used both as a reagent and as a base. Bases other than BH such as potassium carbonate, tri-($C_1$–$C_6$)alkylamine or sodium hydride may also be used. The reaction is carried out at a temperature of about 75° to 230° C. When the reaction is carried out in the presence of a base, such as sodium hydrilde, potassium $C_1$–$C_4$ alkoxide, or an organolithium compound such as n-butyllithium, a molar equivalent of the amine is used.

When B is —$OCHR_1R_2$ or —$SCHR_1R_2$, a base which is capable of deprotonating BH may be used, such as an alkali metal hydride such as sodium or potassium hydride, or an organometallic base such as sodium diisopropylamide, sodium bis(trimethylsilyl)amide, lithium diisopropylamide, lithium bis(trimethylsilyl)amide, sodium or potassium $C_1$–$C_4$ alkoxide, or n-butyllithium. The solvent used can be, for example, tetrahydrofuran, acetonitrile, dimethylsulfoxide, acetone, methylene chloride, toluene, a $C_2$–$C_5$ alcohol, chloroform, benzene, xylene, or 1-methyl-2-pyrrolidinone, and the reaction temperature can range from about 0° C. to about 180° C., and is preferably from about 50° C. to about 80° C.

Compounds of the formulae I, II and III wherein B is as defined with reference to formulae I, II and III and $R_3$ is defined with reference to the same except that $R_3$ is not methyl or ethyl (hereinafter $R_{20}$, which is defined as $R_3$ with the exception that it can not be methyl or ethyl) may be prepared by reacting a compound of the formulae I, II or III wherein $R_3$ is chloro with a nucleophile of the formula $R_{20}H$ with or without an organic or inorganic base. Suitable bases include sodium and sodium hydride, when $R_{20}H$ is an alkanol or an alkane thiol; and weaker bases such as potassium carbonate or triethylamine when $R_{20}H$ is an amine. The compounds of formula I wherein $R_{20}$ is fluoro may be prepared from the corresponding compounds wherein $R_{20}$ is chloro on reaction with tetrabutylammonium fluoride. Suitable solvents are dimethylsulfoxide, tetrahydrofuran, or methylene chloride, preferably tetrahydrofuran.

Compounds of the formula I wherein B is —$CR_1R_2R_{11}$, —$C(C=CR_2R_{12})R_1$, —$CHR_2OR_{12}$, —$CHR_2SR_{12}$, or —$C(O)R_2$, and $R_3$ is $R_{19}$, as defined above, may be prepared as depicted in Scheme I.

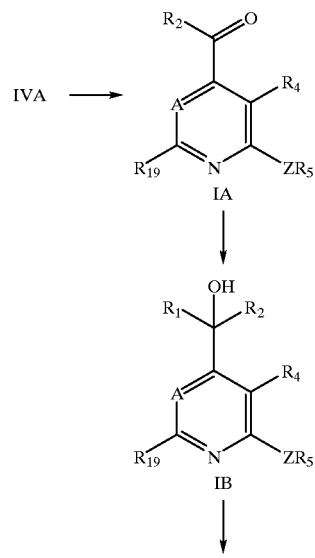

SCHEME 1

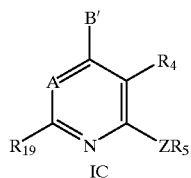

IC

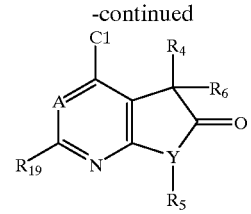

VII

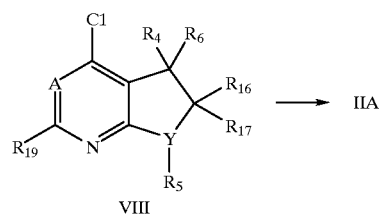

VIII → IIA

Compounds of the formula IV wherein D is cyano and A, $R_4$, $R_5$, and $R_{19}$ are as defined above having formula IVA (not shown), prepared by reacting the corresponding compound wherein D is chloro with potassium cyanide or copper cyanide in dimethylsulfoxide, 1-methyl-2-pyrrolidinone, N,N-dimethylformamide (DMF) or acetamide, are reacted with a Grignard reagent containing group $R_2$, as defined above, to form the compounds of formula IA. Further reaction of the compound of formula IA with a Grignard reagent containing $R_1$ as defined above provides the compound of formula IB. Corresponding compounds of formula IC wherein B" is —$CR_1R_2R_{11}$, or —$C(C=CR_2R_{12})R_1$ may be prepared by conventional methods. Thus, reaction of IB with an acid, such as concentrated sulfuric acid in acetic acid, or Burgess inner salt, such as (carboxysulfamoyl) triethylammonium hydroxide methyl ester, gives a compound of formula IC wherein B' is —$C(=CR_2R_{12})R_1$. Hydrogenation of a compound wherein B' is —$C(=CR_2R_{12})R_1$ using a palladium/carbon (Pd/C) or platinum dioxide catalyst gives a compound IC wherein B' is $CHR_1R_2$. Reaction of compound IB with diethylaminosulfur trifluoride or triphenylphosphine/carbontetrachloride affords a compound IC wherein B' is —$CR_1R_2F$ or —$CR_1R_2Cl$, respectively. Reduction of a compound of formula IA with sodium borohydride gives a compound I wherein B is —$CHR_2OH$. Alkylation of this —$CHR_2OH$ group with alkyl halide such as alkyl iodide in the presence of a base such as sodium hydride at room temperature affords a compound of formula I wherein B is —$CHR_2OR_{12}$.

Compounds of the formula II wherein $R_3$ is $R_{19}$ as defined above may be prepared from compounds of the formula IV wherein $R_{19}$, $R_4$, $R_5$ and A are as defined before, D is chloro, and $YR_{21}$ is NH or —$CHR_{21}$ wherein $R_{21}$ is cyano or —$COO(C_1-C_4$ alkyl), hereafter formula IVB, as shown in Scheme 2.

SCHEME 2

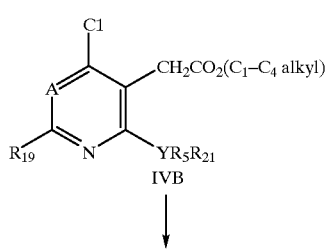

IVB

Compounds of the formula VII wherein $R_4$ and $R_6$ are each hydrogen and Y is N may be prepared by heating compounds of formula IVB with an acid catalyst in a suitable solvent such as toluene, benzene, t-butanol, acetonitrile and acetone, preferably toluene. The acid catalyst may be sulfuric acid, hydrochloric acid, p-toluene sulfonic acid, or methylsulfonic acid, preferably p-toluene sulfonic acid.

When Y in formula IVB is CH or N, a base may be used to deprotonate the proton of the compound of formula IVB. Suitable solvents are tetrahydrofuran, toluene, and methylene chloride, suitable reaction temperatures are between about −78° C. and 100° C., preferably −78° to 50° C., and suitable bases are sodium hydride, potassium hydride, potassium t-butoxide, lithium bis(trimethylsilyl) amide, and lithium or sodium diisopropylamide.

Compounds of the formula VII wherein $R_4$ and $R_6$ are each hydrogen may be deprotonated with a base such as sodium hydride, or an organometallic compound such as lithium bis(trimethylsilyl)amide followed by quenching with an electrophile compound containing the group $R_4$, such as $R_4L$ wherein L is a leaving group such as iodo, bromo, mesylate, tosylate or with p-tolyl-N-fluoro-N— $C_1-C_6$ alkyl sulfonamide, iodine, p-nitrobenzene, dimethylformamide, di($C_1-C_4$ alkyl)ketone, formaldehyde, ($C_1-C_4$ alkyl) aldehyde or bromine, to provide a compound of formula VII wherein $R_4$ is fluoro, chloro, bromo, iodo, hydroxy, $C_1-C_4$ alkyl, S($C_1-C_4$ alkyl), CHO, CH(OH) ($C_1-C_4$ alkyl), C(OH)(di—$C_1-C_4$ alkyl) or $CH_2OH$. Further conventional alkylation of the hydroxy group or oxidation of the thioalkyl group leads to compounds of formula VII wherein $R_4$ is $C_1-C_4$ alkoxy and $SO_n(C_1-C_4$ alkyl) wherein n is 1 or 2, respectively. Oxidation of compounds of formula VII wherein $R_4$ is hydroxy and $R_6$ is hydrogen affords corresponding compounds wherein $CR_4R_6$ is C=O, which on reductive amination with an appropriate amine convert into corresponding compounds wherein $R_4$ is amino. The compounds of formula VII wherein $R_4$ is nitro or amino may be formed by reacting compounds of formula VII wherein $R_4$ and $R_6$ are both hydrogen with alkyl nitrite to form compounds wherein $CR_4R_6$ is C=NOH and oxidizing or reducing to give the compounds of formula VII wherein $R_4$ is nitro or amine, respectively.

Compounds of the formula VII, when one of $R_4$ and $R_6$ is hydrogen, may be converted into corresponding compounds wherein $R_{16}$ and $R_{17}$ are both hydrogen by reduction with a reducing agent such as lithium aluminum hydride in tetrahydrofuran. The same reduction leads to compounds wherein $R_{16}$ is hydrogen and $R_{17}$ is hydroxy, when both of $R_4$ and $R_6$ are riot hydrogen. Alkylation when $R_{17}$ is hydroxy with $C_1$–$C_4$ alkyl iodide in the presence of sodium hydride gives the corresponding compound wherein $R_{17}$ is $O(C_1$–$C_4$ alkyl). Reaction of compounds of formula VII with an organometallic compound such as $di(C_1$–$C_6$ alkyl)zinc, $C_1$–$C_6$ alkyl lithium, or $C_1$–$C_6$ alkyl magnesiumbromide affords compounds of formula VII wherein one of $R_{16}$ or $R_{17}$ is $C_1$–$C_6$ alkyl and the other is hydroxy.

The conversion of compounds of formula VIII to corresponding compounds of formula IIA is by the methods described above for preparation of compounds of formula I.

The compounds of formula III wherein G is oxygen or sulfur and $R_6$ is hydrogen may be prepared by reacting compounds of formula I wherein $R_4$ is amino and Z is NH with phosgene, diphosgene, triphosgene or thiophosgene. The reaction is in the presence of a base such as $tri(C_1$–$C_4$ alkyl)amine in a suitable solvent, preferable tetrahydrofurane at about $-78°$ to about $50°$ C., preferably at $0°$ C. to room temperature. Standard alkylation of these compounds wherein $R_6$ is hydrogen with a suitable base such as sodium hydride in a suitable solvent such as dry tetrahydrofuran provides compounds of the formula III wherein $R_6$ is $C_1$–$C_4$ alkyl.

Compounds of the formula III wherein G is alkyl may be prepared by reacting a compound of the formula I wherein $R_4$ is amino and Z is NH with a compound of the formula $GC(OC_1$–$C_2$ alkyl)$_3$ in the presence of an acid such as p-toluenesulfonic acid (p-TsOH), methanesulfonic acid (MsOH), hydrogen chloride gas (HCl$_g$) or concentrated sulfuric acid ($H_2SO_4$) in an appropriate sovient such as toluene, xylene, benzene, dioxane or THF at a tempeature from about room temperature to about $140°$ C., preferably from about $50°$ C. to about the reflux temperature. Alternatively, a compound of the formula I wherein $R_4$ is amino and Z is NH can be reacted with $[G(C=O)]_2O$, $G(C=O)Cl$ or $G(C=O)F$ in the presence of a base such as pyridine, a derivative of pyridine or a $tri$-$(C_1$–$C_4)$ alkylamine, in an appropriate solvent such as $CH_2Cl_2$, $CHCl_3$, THF, dioxane, toluene or benzene, at a temperature from about $0°$ C. to about the reflux temperature of the reaction mixture, preferably from about $0°$ C. to about room temperature, followed by ring cyclization under acidic conditions (e.g., with pTSOH, MSOH, HCl$_g$, hydrogen bromide gas (HBr$_g$) or concentrated $H_2SO_4$). The ring cyclization can be carried out in an appropriate solvent such as a $C_1$–$C_5$ alcohol, toluene, xylene, benzene, dioxane or THF. Suitable temperatures for this reaction can range from about room temperature to about $140°$ C. Preferably, the reaction temperature is between about $50°$ C. and about the reflux temperature.

Compounds of the formula III wherein G is —O—($C_1$–$C_2$ alkyl) or —OCF$_3$ may be prepared by reacting a compound of the formula III wherein G is oxygen and $R_6$ is hydrogen with a compound of the formula $GOSO_2CF_3$ in the presence of a base such as $tri(C_1$–$C_4$ alkyl)amine, or with lithium bistrimethylsilylamide in HMPA or DMF, and then quenching the reaction with a compound of the formula $GOSO_2OG$ or G—X wherein X is bromo, chloro or $SO_3CF_3$.

The compounds of formula IV wherein D is chloro and $ZR_5$ is $NHR_5$ may be prepared from compounds of formula V:

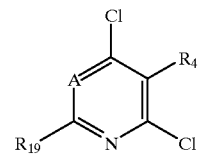

wherein A and $R_4$ are as defined with reference to formula I and $R_{19}$ is as defined above, by reaction with $R_5NH_2$. The reaction is in tetrahydrofuran or dimethylsulfoxide at about $0°$ C. to about $150°$ C., preferably $50°$ to $130°$ C. The compounds of formula IV wherein D is chloro and Z is O, S, $CHR_{21}$ wherein $R_{21}$ is an electron deficient group such as cyano, $C(=O)R$, COOR, wherein R is $C_1$–$C_4$ alkyl, benzoyl or allyl, or $SO_n$— phenyl wherein n=0, 1 or 2 may be prepared by reacting compounds of formula V with $R_5OH$, $R_5SH$, $R_5NH_2$ or $R_5CHR_{21}$. The reaction proceeds in the presence of a base which is capable of deprotonating $R_5ZH$, such as sodium hydride, potassium hydride, potassium carbonate, lithium or sodium bis(trimethylsilyl)amide, lithium or sodium dialkylamide, sodium or potassium ($C_1$–$C_4$ alkoxide) or n-butyllithium, with or without other organometal halides such as copper (I) bromide, iodide or chloride, copper (II) oxide, copper (I) oxide, copper metal and trialkyltinchloride. Examples of solvents that may be used are tetrahydrofuran, dimethylsulfoxide, acetonitrile, methylene chloride, 1-methyl-2-pyrrolidinone, pyridine, quinoline, N,N-dialkylacetamides, 2,4,6,-trimethylpyridine, N,N-dialkylformamides, e.g., N,N-dimethylformamide (DMF), hexamethyl phosphoramide and toluene. The reaction temperature may range from about $0°$ C. to about $180°$ C., and is preferably from about $0°$ to about $150°$ C.

Compounds of the formula IV wherein A is $CR_7$, D is chloro and Z is O, S, $CHR_{21}$ may be prepared by reduction of compounds of formula X, depicted below, wherein $R_7$ and Z are as defined immediately above, with a reducing agent such as phosphorous trichloride in an appropriate solvent such as methylene chloride or chloroform at temperature from about $0°$ C. to about $100°$ C., preferably from about room temperature to about the reflux temperature of the solvent.

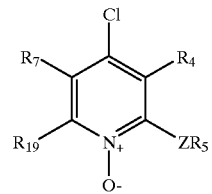

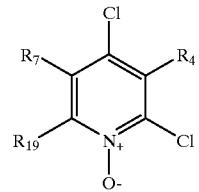

Compounds of the formula X may be prepared from compounds of the formula XI, depicted above, wherein $R_4$ is as defined as it is for formula I and $R_{19}$ is as defined above (i.e., methyl or ethyl), by reaction with a compound of the formula $R_5OH$, $R_5SH$ or $R_5CHR_{21}$. This reaction proceeds in the presence of a base which is capable of deprotonating $R_5ZH$, such as sodium hydride, potassium hydride, lithium, sodium or potassium bis(trimethylsilyl)amide, lithium, sodium or potassium dialkylamide, sodium or potassium $C_1$–$C_4$alkoxide, or n-butyllithium Suitable solvents include tetrahydrofuran, dioxane, dimethylsulfoxide, 1-methyl-2-pyrrolidinone, pyridine, N,N-di-($C_1$–$C_4$ alkyl)acetamides, acetamide, N,N-di-($C_1$–$C_4$ alkyl)formamides, acetonitrile, methylene chloride, touluene and xylene. Suitable reaction temperatures may range from about −78° C. to about 150° C., and are preferably between about −40° C. to about 150° C.

Compounds of the formula XI may be prepared by reacting the corresponding compounds of formula a V wherein A is —$CR_7$ and $R_4$ and $R_{19}$ are defined as above, with an oxidizing agent such as m-chloroperbenzoic acid, peracetic acid or pertrifluoroacetic acid, in a solvent such as methylene chloride, chloroform, acetic acid, DMF, methanol or a mixture of one or more of the foregoing solvents, at temperature from about 0° C. to about 100° C., preferably from about room temperature to about 60° C.

When $R_4$ is an electron withdrawing group such as a $NO_2$, —COO($C_1$–$C_4$ alkyl), —COOH, CN or —CO($C_1$–$C_4$)alkyl, the reaction order for the coupling reactions that introduce the B arid $ZR_5$ groups in the synthesis of compounds of formula I may be reversed. The B group may be introduced before the $ZR_5$ coupling step using the methods analogous to those described above. For example, compounds of the formula I wherein $R_4$ is an election deficient group may be prepared by reacting a compound of the formula XII with a compound of the formula $HZR_5$. Compounds of the formula XII may be prepared by reacting a compound of the formula V wherein A is $CR_7$ and $R_{19}$ and $R_4$ are defined as above with a compound of the formula B"H in the presence of a base.

Compounds of the formula IV wherein D is chloro and Z is —N($C_1$–$C_4$ alkyl) may be prepared by reacting the corresponding compounds wherein Z is NH with a base, at a temperature from about −78° C. to about 100° C., preferably from about 0° C. to about room temperature, followed by quenching with $C_1$–$C_4$ alkyl iodide or bromide. Suitable bases include, for example, sodium hydride, lithium or sodium bis(trimethylsilyl)amide, lithium or sodium dialkylamide, and n-butyllithium. Suitable solvents include, for example, tetrahydrofuran, dimethylsulfoxide, toluene, benzene or methylene chloride.

Compounds of the formula IV wherein D is chloro, hydroxy or OP wherein P is a standard protecting group for hydroxy and Z is —$CR_{13}R_{14}$ may be prepared by alkylation, using an $R_{13}$ containing alkylating agent such as $R_{13}$l, compounds of the formula IV wherein Z is —$CHR_{21}$ in the presence of a base that is capable of deprotonating the proton in the Z group, as mentioned above, followed by quenching with an $R_{14}$ containing alkylating agent such as $R_{14}$l. Heating compounds of the formula IV wherein D is chloro or hydrogen and Z is —CH(CN) in about 85% phosphoric acid at about the reflux temperature yields the corresponding compounds of formula IV wherein D is hydroxy and Z is $CH_2$. Deprotonation of the compounds of formula IV wherein Z is $CH_2$ with a base, such as described above for deprotonation of $R_5ZH$, followed by quenching with a suitable electrophile such as a ($C_1$–$C_6$ alkyl)iodide, iodine, bromine, acetylchloride, formaldehyde, acetone, p-tolyl-N-fluoro-N—($C_1$–$C_6$ alkyl)sulfonamide, nitrobenzene, $C_1$–$C_6$ alkylnitrite, ethylene oxide or dihaloethane yields the corresponding compounds of formula IV wherein Z is —$CHR_{13}$, —CH(OH), cyclopropyl or —C(NOH). Further alkylation of compounds wherein Z is —$CHR_{13}$, eg., as described immediately above, with an alkylating agent of the formula $R_{14}$l, produces the corresponding compounds wherein Z is —C($R_{13}R_{14}$).

Conversion of —C($R_5$)NOH or —CH(OH)$R_5$ to C(O)$R_5$ may be accomplished by known methods. Hydrogenation or reduction of compounds wherein Z is —C=NOH provides compounds wherein Z is —$CHNH_2$. Some of the intermediates may require a protecting or deprotecting procedure to control the reaction selectivity using standard organic chemistry.

Compounds of the formula V wherein A is N (hereinafter referred to as compounds of the formula VB) or A is $CR_7$ (i.e., compounds of the formula VA), and $R_4$ and $R_{19}$ are defined as they are for formula I, may be prepared by reacting the corresponding compounds of formulae VIB and VIA, respectively, with 1 equivalent or an excess of $POCl_3$ at a temperature from about room temperature to about 180° C., preferably at the reflux temperature, with or without a solvent. Compounds of formula VIA may be prepared by the methods analogous to those described in the literature and well known to those skilled in the art. (See *Helv. Chimica Acta.*, 25, p. 1306–1313 (1942)).

Compounds of formula VIB may be prepared by reacting 1 equivalent of the HCl salt of $R_{19}C(=NH)(NH_2)$, 1 equivalent of $R_4CH(COO—(C_1–C_2 alkyl))_2$, and 2 equivalents of a base such as a sodium alkoxide, e.g., sodium methoxide in a mixture of an alcohol (e.g., methanol), and acetone at a temperature from about 50° C. to about 200° C., preferably at the reflux temperature.

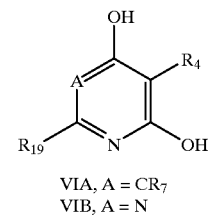

VIA, A = $CR_7$
VIB, A = N

When compounds of this invention contain one or more chiral centers, it is understood that the invention includes the racemic mixtures as well as all individual enantiomers and diastereomers of such compounds, and mixtures thereof.

The subject invention also includes isotopically-labeled compounds, which are identical to those recited in formulas I, II, or III, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Compounds of the present invention and pharmaceutically acceptable salts of said compounds that contain the aforementioned isotopes and/or other isotopes of other atoms are within the scope of this invention. Isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation arid detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formulas I, II, or III of this invention can generally be prepared by carrying out the procedures disclosed in the Schemes and/or in the Examples below, by substituting a readily available isotopically labeled reagent for a non-isotopically labeled reagent.

The acid addition salts of compounds of the formulae I, II and III ("the active compounds of this invention) can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The active compounds of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formulae I, II and III and their pharmaceutically acceptable carriers can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for compounds of the formulae I, II or III and their salts will depend on the intended route of administration and factors such as the age and weight of the patient, as generally known to a physician. The dosages will also depend on the particular illness to be treated. For instance, the daily dosage for stress-induced illnesses, inflammatory disorders, Alzheimer's disease, gastrointestinal diseases, anorexia nervosa, hemorrhagic stress and drug and alcohol withdrawal symptoms will generally range from about 0.1 to about 50 mg/kg body weight of the patient to be treated. The effective dose can be determined by those of ordinary skill in the art by reference to texts pertaining to treatment of the particular disorder or condition to be treated.

Methods that may be used to determine the CRF antagonist acivity of the active compounds of this invention and their pharmaceutically acceptable salts are described in *Endocrinology*, 116, 1653–1659 (1985) and *Peptides*, 10, 179–188 (1985). The binding activities for compounds of formulae I, II and III, expressed as $IC_{50}$ values, generally range from about 0.5 nanomolar to about 10 micromolar.

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochloroforin ($CDCl_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

The following abbreviations are used in the Examples: Ph=phenyl; iPr=isopropyl; HRMS=high resolution mass spectrum.

EXAMPLE 1

The compounds below were prepared by reaction of (2-chloro-6-methyl-3-nitric-pyridin-4-yl)-(alkyl- or dialkyl)-amine with substituted phenol by a method analogous to the following: To a mixture of (2-chloro-6-methyl-3-nitro-pyridin-4-yl)-(alkyl- or dialkyl)-amine (1 mmol) and 2,4,6-trimethylphenol (1 mmol) in dry THF was added potassium tert-butoxide (1 mmol) and the resulting mixture was stirred at room temperature until all starting material was consumed. The mixture was quenched with water and extracted with ethyl acetate. The organic layer was dried and concentrated to give the title compound after purification through silica gel column chromatography:

2-[2-(4-Chloro-2,6-dimethyl-phenoxy)-6-methyl-3-nitro-pyridin-4-(S)-ylamino]-butan-1-ol 1H NMR(CDCl$_3$) d 7.69(,1H), 6.289s,1H), 3.65–3.80(m, 2H), 3.60m,1H), 2.12(s,3H), 2.08(s,6H), 1.8(brs,1H), 1.5–1.8(m,2H), 1.01 (t,3H) ppm.

(1-Methoxymethyl-propyl)-[6-methyl-3-nitro-2-(4-trifluoromethoxy-phenoxy)-pyridin-4-yl]-amine yellow solid, mp. 75–76° C., Anal. For $C_{18}H_{20}N_3O_5F_3$, calc. C52.05; H, 4.85; N, 10.12; found, C, 52.14; H, 5.04; N, 10.13

2-(2-Amino-4,6-dichloro-phenoxy)-6-methyl-3-nitro-pyridin-4-yl]-(1-methoxymethyl-propyl)-amine 1H NMR (CDCl$_3$) d 9.55(d,1H), 7.23(d,1H), 7.00(d,1H), 6.05(s,1H), 3.69(m,1H), 3.49(m,2H), 3.38(s,3H), 2.35(s, 3H), 1.78(m,1H), 1.65(m,1H), 0.99(t,3H) ppm.

3-Methoxy-2-[4-(1-methoxymethyl-propylamino)-6-methyl-3-nitro-pyridin-2-yloxy]-benzaldehyde yellow solid, mp. 126.5–130.5° C., Anal. For $C_{19}H_{23}N_3O_6$, calc. C58.60; H, 5.95; N, 10.79; found, C, 58.45; H, 6.11; N, 10.32

[2-(2,6-Dibromo-4-trifluoromethoxy-phenoxy)-6-methyl-3-nitro-pyridin-4-yl]-(1-methoxymethyl-propyl)-amine yellow solid, 1H NMR(CDCl$_3$) d 8.00(d,1H), 7.49(,2H), 6.35(s,1H), 3.64(m,1H), 3.53(m,2H), 3.43(s,3H), 2.20(s, 3H), 1.6–1.9(m,4H), 1.04(t,3H)ppm.

[2-(2-Bromo-4-chloro-6-methoxy-phenoxy)-6-methyl-3-nitro-pyridin4-yl]-(1-methoxymethyl-propyl)-amine yellow solid, mp. 111.8–113.6° C., Anal. For $C_{15}H_{21}N_3O_5BrCl$, calc, C, 45.54; H, 4.46; N, 8.85; found, C, 45.94; H, 4.32; N, 8.68

[2-(2,4-Dichloro-phenoxy)-6-methyl-3-nitro-pyridin-4-yl]-(1-methoxymethyl-propyl)-amine 1H NMR (CDCl$_3$) d 7.83(d,1H), 7.46(d,1H), 7.30(dd,1H), 7.15(dd,1H), 6.33(s,1H), 3.65(m,1 H), 3.51 (m,2H), 3.42(s, 3H), 2.21(s,3H), 1.82(m,1H), 1.66(m,1H), 1.03(t,3H) ppm.

[2-(2-Bromo-6-chloro-4-methoxy-phenoxy)-6-methyl-3-nitro-pyridin-4-yl]-(1-methoxymethyl-propyl)-amine 1H NMR(CDCl$_3$) d 7.88(d,1H), 7.04(d,1H), 6.93(d,1H), 6.27(s,1H), 3.79(s,3H), 3.60(m,1H), 3.4–3.5(m,2H), 3.38(s, 3H), 2.15(s,3H), 1.78(m,1H), 1.64(m,1H), 0.99(t,3H)

(1-Methoxymethyl-propyl)-[6-methyl-3-nitro-2-(2,4,6-trimethoxy-phenoxy)-pyridin-4-yl]-amine mp. 126.8–129.5° C.; Anal. For $C_{20}H_{27}N_3O_7$ calc. C, 57.00; H, 6.46; N, 9.97; found C, 56.94; H, 6.85; N, 9.66.

EXAMPLE 2

2-Chloro-N-[4-(1-ethyl-propylamino)-6-methyl-2-(2,4,6-trimethyl-phenoxy)-pyridin-3-yl]-acetamide To a solution of N-4-(1-ethyl-propyl)-6-methyl-2-(2,4,6-trimethyl-phenoxy)-pyridine-3,4-diamine (250 mg, 0.763 mmol) in dry THF was added chloroacetyl chloride (86 mg, 0.763 mmol) and triethylamine (77 mg, 0.763 mmol) at 0° C. The resulting mixture was warmed to room temperature and stirred for 1 hr. The mixture was quenched with water and extracted with ethyl acetate. The organic layer was dried over anhydrous sodium sulfate, filtered, and concentrated to dryness to give the title compound as a solid. The solid was purified through silica gel column chromatography to give 280 mg (91%) of tan crystals, mp. 152–154° C.

1H NMR(CDCl$_3$) d 8.07(brs,1H), 6.88(s,2H), 6.16(s,1H), 4.75(m,1H), 4.25(s,2H), 3.33(m,1 H), 2.30(s,3H), 2.18(s, 3H), 2.08(s,6H), 1.4–1.75(m,4H), 0.97(t,6H) ppm.

The following compounds were prepared by an analogous method to that in the preceding paragraph:

3-Chloro-N-[4-(1-ethyl-propylamino)-6-methyl-2-(2,4,6-trimethyl-phenoxy)-pyridin-3-yl]-propionamide tan solid,mp. 183–185° C. Anal. For $C_{23}H_{32}ClN_3O_2$ calc C, 66.09; H, 7.72; N, 10.05; found, C, 66.27; H, 7.87; N, 9.99.

2-Chloro-N-[4-(1-ethyl-propylamino)-6-methyl-2-(2,4,6-trimethyl-phenoxy)-pyridin-3-yl]-propionamide mp. 170–172° C., Anal. For $C_{23}H_{32}ClN_3O_2$ calc. C, 66.09; H, 7.72; N, 10.05; found C, 66.20; H, 7.52; N, 10.09.

EXAMPLE 3

N3-Allyl-N4-(1-ethyl-propyl)-6-methyl-2-(2,4,6-trimethyl-phenoxy)-pyridine-3,4-diamine To a solution of N-4-(1-ethyl-propyl)-6-methyl-2-(2,4,6-trimethyl-phenoxy)-pyridine-3,4-diamine (500 mg, 1.52 mmol) in dry THF was added 1M in THF of lithium bis(trimethylsilyl)amide (1.6 ml, 1.6 mmol) at −78° C. After stirring at −78° C. for 10 min, allyl bromide (0.13 ml, 1.52 mmol) was added and the resulting mixture was stirred at that temperature for 20 min, then warmed to room temperature overnight. The mixture was quenched with water and extracted with ethyl acetate. The organic layer was dried over anhydrous sodium sulfate, filtered, and concentrated to dryness to give the title compound ;as a green-blue oil. The oil was purified through silica gel column chromatography using 5% ethyl acetate in hexane as eluent to give a yellow crystal, mp. 86–88° C.

1H NMR(CDCl$_3$) d 6.87(s,2H), 6.0(m,2H), 5.2–5.35(m, 2H), 4.8(d,1H), 3.54(d,2H), 3.3(m,1H), 3.05(s,1H), 2.30(s, 3H), 2.14(s,3H), 2.09(s,6H), 1.4–1.6(m,4H), 0.96(t,6H) ppm.

The following compounds were prepared by an analogous method:

N3-(3-Chloro-propyl)-N4-(1-ethyl-propyl )-6-methyl-2-(2,4,6-trimethyl-phenoxy)-pyridine-3,4-diamine 1H NMR(CDCl$_3$) d 6.85(s,2H), 6.05(s,1H), 4.9(d,1H), 3.8(m,2H), 3.3(m,1H), 3.1(m,2H), 2.3(s,3H), 2.159s,3H), 2.04(s,6H), 1.79m,2H), 1.5(m,2H), 1.0(m,6H) ppm.

N4-(1-Ethyl-propyl)-6-methyl-N3-propa-1,2-dienyl-2-(2,4,6-trimethyl-phenoxy)-pyridine-3,4-diamine 1H NMR(CDCl$_3$) d 8.93(d,1H), 6.86(s,2H), 6.66(m,1H), 6.09(s,1H), 5.4–5.6(m,2H), 5.54(d,1H), 3.27(m,1H), 2.27(s, 3H), 2.12(s,3H), 2.05(s,6H), 1.6(m,4H), 0.94(t,6H) ppm.

EXAMPLE 4

2-[3-Amino-2-(4-chloro-2,6-dimethyl-phenoxy)-6-methyl-pyridin-4-(S)-ylamino]-butan-1-ol A mixture of 2-[2-(4-Chloro-2,6-dimethyl-phenoxy)-6-methyl-3-nitro-pyridin-4-(S)-ylamino]-butan-1-ol (120 mg) and Fe (73 mg) in 12 ml of 1:1 of AcOH:H2O was heated at reflux for 2 hr. The reaction mixture was concentrated to dryness. The residue was quenched with water, basified to pH 12 and filtered through celite. The filtrate was extracted with chloroform. The organic layer was washed with brine, dried and concentrated to give the title compound as a yellow solid. The solid was purified through silica gel column chromatography using 1:1 EtOAc:hexane as eluent to give the title compound as a white solid, mp. 161–162° C.

1H NMR(CDCl$_3$) d 7.03(s,2H), 6.15(s,1H), 3.75(m,2H), 3.47(m,1H), 2.25(brs,3H), 2.08(s,6H), 1.5–1.8(m,2H), 0.98t,3H) ppm

EXAMPLE 5

2-(4-Chloro-2,6-dimethyl-phenoxy)-4-(1-ethyl-propylamino)-6-methyl-nicotinic acid methyl ester A mixture of 4-chloro-6-methyl-2-(4-Chloro-2,6-dimethyl-phenoxy)-nicotinic acid methyl ester (77 mg, 0.226 mmol) and 1-ethyl-propyl-amine in DMSO was heated at 120° C. for 4 hr. The mixture was quenched with sat. ammonium chloride, water, brine and extracted with ethyl acetate. The organic layer was dried and concentrated to give 140 mg of yellow solid. 1HNMR(CDCl$_3$) d 8.10(d, 1H), 7.03(s,2H), 6.09(s,1H), 3.88(s,3H), 3.35(m,1H), 2.10 (s,3H), 2.08(s,6H), 1.5–1.7(m,4H), 0.96(t,6H) ppm.

EXAMPLE 6

2-(4-Bromo-2,6-dimethyl-phenoxy)-4-(1-ethyl-propylamino)-6-methyl-nicotinic acid methyl ester A mixture of 4-chloro-6-methyl-2-(4-bromo-2,6-dimethyl-phenoxy)-nicotinic acid methyl ester and 1-ethyl-propyl-amine in DMSO was heated at 120° C. for 16 hr. The mixture was quenched with water, brine and extracted with ethyl acetate. The organic layer was dried and concentrated to dryness. The residue was purified through silica gel column chromatography using hexane to 3% ethyl acetate in hexane as eluent to give the title compound as a white solid. 1H NMR(CDCl$_3$) d 8.1(d,1H), 7.18(s,2H), 6.08(s,1H), 3.87 (s,3H), 3.35(m,1H), 2.10(s,3H), 2.08(s,6H), 1.4–1.7(m,4H), 0.96(t,6H) ppm.

EXAMPLE 7

4-(1-Ethyl-prop-2-ynylamino)-6-methyl-2-(2,4,6-trimethyl-phenoxy)-nicotinic acid methyl ester A mixture of 4-chloro-6-methyl-2-(2,4,6-trimethyl-phenoxy)-nicotinic acid methyl ester and 1-ethyl-propyl-amine in DMSO was heated at 130° C. overnight. The mixture was quenched with water, brine and extracted with ethyl acetate. The organic layer was dried and concentrated to dryness. The residue was purified through silica gel column chromatography to give the title compound. 1H NMR(CDCl$_3$) d 8.26(d,1H), 6.87(s,2H), 6.26(s,1H), 4.11 (m,1H), 3.87(s,3H), 2.324(m,1H), 2.30(s,3H), 2.17s,3H), 2.08(s,6H), 1.92(q,2H), 1.16(t,3H) ppm.

EXAMPLE 8

4-(s)-(1-Hydroxymethyl-propylamino)-6-methyl-2-(2,4,6-trimethyl-phenoxy)-nicotinic acid methyl ester A mixture of 4-chloro-2-(2,4,6-trimethyl-phenoxy)-6-methyl-nicotinic acid methyl ester (500 mg, 1.56 mmol) and (S)-2-amino-1-butanol (696 mg, 7.82 mmol) in DMSO was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give 610 mg of crude product as an oil. The oil was purified through silica gel column chromatography using 30% ethyl acetate in hexane as eluent to give the title compound. Anal. calc. for $C_{21}H_{28}N_2O_4 \cdot \frac{1}{2}H_2O$: C, 66.11; H, 7.66; N, 7.34; found: C, 66.27; H, 7.60; N, 7.21.

EXAMPLE 9

4-(1-Ethyl-2-hydroxy-propylamino)-6-methyl-2-(2,4,6-trimethyl-phenoxy)-nicotinic acid methyl ester A mixture of 4-chloro-2-(2,4,6-trimethyl-phenoxy)-6-methyl-nicotinic acid methyl ester (250 mg, 0.78 mmol) and 3-amino-pentan-2-ol (320 mg, 3.13 mmol) in DMSO was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give 280 mg of crude product as an oil. The oil was purified through silica gel column chromatography using 20% ethyl acetate in hexane as eluent to give the title compound as a yellow solid, mp 116–120° C.

1H NMR(CDCl$_3$) d 8.17(m,1H), 6.87(s,2H), 6.21&6.14 (two s, 1H), 3.88(s,3H), 3.8–4.0(m,2H), 3.5(m,1H), 3.3(m, 1H), 2.30(s,3H), 2.12(s,3H), 2.09(s,6H), 1.8(d,1H), 1.5–1.8 (m,2H), 1.26(d,3H), 0.99(t,3H) ppm.

EXAMPLE 10

2-(4-Bromo-2,6-dimethyl-phenoxy)-4-(S)-(1-hydroxymethyl-propylamino)-6-methyl-nicotinic acid methyl ester A mixture of 4-chloro-2-(4-bromo-2,6-trimethyl-phenoxy)-6-methyl-nicotinic acid methyl ester (850 mg) and (S)-2-amino-1-butanol in DMSO was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give 764 mg of crude product as an oil. The oil was purified through silica gel column chromatography to give the title compound. 1H NMR (CDCl$_3$) d 8.15(d,1H), 7.16(s,2H), 6.18(s,1H), 3.86 (s,3H), 3.72(m,1H), 3.70(m,1H), 3.54(m,1H), 2.10(s,3H), 2.06(s,6H), 1.5–1.8(m,2H), 1.00(t,3H) ppm.

EXAMPLE 11

2-(4-Bromo-2,6-dimethyl-phenoxy)-4-(S)-(1-methoxymethyl-propylamino)-6-methyl-nicotinic acid methyl ester A mixture of 4-chloro-2-(4-bromo-2,6-trimethyl-phenoxy)-6-methyl-nicotinic acid methyl ester and 1-methoxymethyl-propylamine in DMSO was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give crude product. The crude compound was purified through silica gel column chromatography to give the title compound.

EXAMPLE 12

2-(4-Chloro-2,6-dimethyl-phenoxy)-4-(1-hydroxymethyl-propylamino)-6-methyl-nicotinic acid methyl ester A mixture of 4-chloro-2-(4-chloro-2,6-dimethyl-phenoxy)-6-methyl-nicotinic acid methyl ester (9.000 g, 26.45 mmol) and (S)-2-amino-1-butanol (12.7 ml) in 1-methyl-2-pyrrolidinone was heated at 130° C. for 2 hr. then at 100° C. overnight. The mixture cooled to rt and poured into ice-water and diluted with ethyl acetate. The organic layer was separated, washed with water, dried over anhydrous sodium sulfate, filtered, and concentrated to dryness to give 13.6 g of crude product as a light yellow oil. The oil was purified through silica gel column chromatography using chloroform to 2% MeOH in chloroform as eluent to give 6.6839 g (64%) of the title compound as a white glass foam. The glass foam was triturated with hexane to give a white solid. The solid was recrystallized from di-iso-propyl ether to give a white crystals, mp 122.5–124° C. Anal. calc. for $C_{20}H_{25}ClN_2O_4$: C, 61.14; H, 6.41; N, 7.13; found: C, 60.98; H, 6.43; N, 6.95.

EXAMPLE 13

2-(4-Chloro-2-methoxy-phenoxy)-4-(S)-(1-hydroxymethyl-propylamino)-6-methyl-nicotinic acid methyl ester A mixture of 4-chloro-2-(4-Chloro-2-methoxy-phenoxy)-6-methyl-nicotinic acid methyl ester and (S)-2-amino-1-butanol in 1-methyl-2-pyrrolidinone was heated at 130° C. overnight. The mixture cooled to room temperature and poured into ice-water and diluted with ethyl acetate. The organic layer was separated, washed with water, dried over anhydrous sodium sulfate, filtered, and concentrated to dryness. The residue was purified through silica gel column chromatography to give the title compound as a solid mp. 92.8–93.8° C., Anal. For $C_{19}H_{23}N_2O_5Cl$ calc. C, 57.80; H, 5.87; 7.09; found, C, 57.70; H, 5.89;, 7.02.

EXAMPLE 14

2-(4-Chloro-2,6-dimethyl-phenoxy)-4-(1-ethyl-2-hydroxy-propylamino)-6-methyl-nicotinic acid methyl ester A mixture of 4-chloro-2-(4-chloro-2,6-dimethyl-phenoxy)-6-methyl-nicotinic acid methyl ester (500 mg, 1.47 mmol) and 3-amino-pentan-2-ol (758 mg, 7.35 mmol) in 1-methyl-2-pyrrolidinone was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give an oil. The oil was purified through silica gel column chromatography using 20% ethyl acetate in hexane as eluent to give the title compound as a white crystal, mp 133–135° C.

1H NMR(CDCl$_3$) d 8.19(m,1H), 7.00(s,2H), 6.20&6.14 (two sets of s,1H), 3.8–3.9(m,1H), 3.86(s,3H), 3.3&3.5(two sets of m,1H), 2.07(s,3H), 2.06(s,6H), 1.75(m,1H), 1.55(m, 1H), 1.24(d,3H), 0.96(t,3H)ppm.

EXAMPLE 15

2-(4-Chloro-2,6-dimethyl-phenoxy)-4-(1-ethyl-2-methoxy-propylamino)-6-methyl-nicotinic acid methyl ester To a solution of 2-(4-chloro-2,6-dimethyl-phenoxy)-4-(1-ethyl-2-hydroxy-propylamino)-

6-methyl-nicotinic acid methyl ester (50 mg, 0.123 mmol) in dry THF was added NaH and stirred for 20 min. An excess of MeI was added and the resulting mixture was stirred at rt overnight. The mixture cooled to rt and quenched with water and extracted with ethyl acetate. The organic layer was separated, washed with water, dried over anhydrous sodium sulfate, filtered, and concentrated to dryness to give an oil. The oil was purified through silica gel column chromatography using 20% ethyl acetate in hexane asan eluent to give the title compound as a clear oil. 1H NMR(CDCl$_3$) d 8.20(d,1H), 7.00(s,2H), 6.14&6.10(two sets of s,1H), 3.859s,3H), 3.47(m,1H), 3.39&3.37(two sets of s,3H), 2.08 (s,3H), 2.06(s,6H), 1.75(m,1H), 1.58(m,1H), 1.14(t,3H), 0.95(t,3H)ppm.

EXAMPLE 16

2-(4-Chloro-2,6-dimethyl-phenoxy)-4-(1-ethyl-2-oxo-propylamino)-6-methyl-nicotinic acid methyl ester The title compound was prepared by Dess-Martin oxidation of 2-(4-chloro-2,6-dimethyl-phenoxy)-4-(1-ethyl-2-hydroxy-propylamino)-6-methyl-nicotinic acid methyl ester. A, white solid was obtained after silica gel column chromatography. 1H NMR(CDCl$_3$) d 8.6(d,1H), 7.01(s,2H), 5.899s,1H), 3.9–4.0(m,1H), 3.90(s,3H), 2.17(s,3H), 2.07(s, 3H), 2.05(s,3H), 1.859m, 1H), 1.93(m, 1H), 1.00(t,3H) ppm.

EXAMPLE 17

2-(4-Chloro-2,6-dimethyl-phenoxy)-4-(1-formyl-propylamino)-6-methyl-nicotinic acid methyl ester The title compound was prepared by Dess-Martin oxidation of 2-(4-chloro-2,6-dimethyl-phenoxy)-4-(1-hydroxymethyl-propylamino)-6-methyl-nicotinic acid methyl ester. The title compound was obtained after column chromatography. 1H NMR (CDCl$_3$) 9.54(d,1H), 8.56(d,1H), 7.01(s,2H), 5.93(s,1H), 3.92(m,1H), 3.89(s,3H), 2.08(s,3H), 2.05(s,6H), 1.05(t,3H) ppm.

EXAMPLE 18

2-(4-Chloro-2,6-dimethyl-phenoxy)-4-(S)-(4-ethyl-2-oxo-oxazolidin-3-yl)-6-methyl-nicotinic acid methyl ester A mixture of 2-(4-chloro-2,6-dimethyl-phenoxy)-4-(1-hydroxymethyl-propylamino)-6-methyl-nicotinic acid methyl ester (106 mg, 0.27 mmol), triphosgene )27 mg, 0.090 mmol), triethylamine (27 mg, 0.27 mmol) in dry THF was stirred at room temperature for 2 hr. The mixture was quenched with water and extracted with ethyl acetate. The organic layer was separated, washed with water, dried over anhydrous sodium sulfate, filtered, arid concentrated to dryness to give 13.6 g of crude product as a white glass foam. The foam was triturated with hexane/diethyl ether to give a white solid, mp. 144–145.5° C., Anal. For $C_{21}H_{23}ClN_2O_5$ calc.: C, 60.22; H, 5.53; N, 6.69; found: C, 60.10, H, 5.79; N, 6.66.

EXAMPLE 19

2-(4-Chloro-2,6-dimethyl-phenoxy)-4-(S)-{1-[(2-hydroxy-ethylamino)-methyl]-propylamino}-6-methyl-nicotinic acid methyl ester To a solution of 2-(4-chloro-2,6-dimethyl-phenoxy)-4-(1-formyl-propylamino)-6-methyl-nicotinic acid methyl ester in dichloroethane was added 2-amino-ethanol, sodium cyanoborohydride, acetic acid, anhydrous sodium sulfate. The resulting mixture was heated at reflux and cooled to rt. The mixture was quenched with water and extracted with chloroform. The organic layer was separated, washed with water, dried over anhydrous sodium sulfate, filtered, and concentrated to dryness. After chromatography, the title compound was obtained as a white glass foam. 1H NMR (CDCl$_3$) d 8.3(d,1H), 7.0(s,2H), 6.1(s,1H), 3.9(s,3H), 3.64 (m,2H), 3.57(m,1H), 2.90(m,2H), 2.83(m,2H), 2.5(brs,2H), 2.09(s,3H), 2.06(s,6H), 1.65(m,2H), 0.97(t,3H) ppm.

EXAMPLE 20

4-[Ethyl-(2-hydroxy-ethyl)-amino]-6-methyl-2-(2,4,6-trimethyl-phenoxy)-nicotinic acid methyl ester A mixture of 4-chloro-6-methyl-2-(2,4,6-trimethyl-phenoxy)-nicotinic acid methyl ester and 1-ethyl-propyl-amine in 1-methyl-2-pyrrolidinone was heated at 130° C. until starting material was consumed. The mixture was quenched with water, brine and extracted with ethyl acetate. The organic layer was dried and concentrated to dryness.

The residue was purified through silica gel column chromatography to give the title compound. 1H NMR(CDCl$_3$) d 6.85(s,2H), 6.40(s,1H), 3.88(s,3H), 3.73(t,2H), 3.43(t,2H), 3.31(q,2H), 2.27(s,3H), 2.22(s,3H), 2.06(s,6H), 1.15(t,3H) ppm.

EXAMPLE 21

4-[Ethyl-(2-methanesulfonyloxy-ethyl-amino]-6-methyl-2-(2,4,6-trimethyl-phenoxy)-nicotinic acid methyl ester A mixture of 4-[ethyl-(2-hydroxy-ethyl)-amino]-6-methyl-2-(2,4,6-trimethyl-phenoxy)-nicotinic acid methyl ester, methanesulfonyl chloride and triethylamine in methylene chloride was stirred at rt until all starting material were consumed. The mixture was quenched with water, brine and extracted with methylene chloride. The organic layer was dried and concentrated to dryness. The residue was purified through silica gel column chromatography to give the title compound. 1H NMR(CDCl$_3$) d 6.83(s,2H), 6.25(s,1 H), 4.34(t,2H), 3.86(s,3H), 3.6(t,2H), 3.38(t,2H), 3.09(s,3H), 2.25(s,3H), 2.20(s,3H), 2.04(s,6H), 1.18(t,3H) ppm.

EXAMPLE 22

4-[(2-Hydroxy-ethyl)-thiophen-2-ylmethyl-amino]-6-methyl-2-(2,4,6-trimethyl-phenoxy)-nicotinic acid methyl ester A mixture of 4-chloro-6-methyl-2-(2,4,6-trimethyl-phenoxy)-nicotinic acid methyl ester and 2-[(thiophen-2-ylmethyl)-amino]-ethanol in 1-methyl-2-pyrrolidinone was heated at 130° C. overnight. The mixture was quenched with water, brine and extracted with ethyl acetate. The organic layer was dried and concentrated to dryness. The residue was purified through silica gel column chromatography to give the title compound. 1H NMR (CDCl$_3$) d 7.22(m,1H), 6.94m,2H), 6.84(s,2H), 6.44(s,1H), 4.52(s,2H), 3.91(s,3H), 3.679t,2H), 3.369t,2H), 2.279s,3H), 2.20(s,3H), 2.07(s,6H) ppm.

EXAMPLE 23

The following compounds were prepared by the method analogous to that in Example 5, starting with an appropriate 4-chloro-6-methyl-2-(substituted-phenoxy)-nicotinic acid alkyl ester with an appropriate alkyl- or dialkyl-amine.

4-(2,2-Dimethyl-4-phenyl-[1,3]dioxan-5-ylamino)-6-methyl-2-(2,4,6-trimethyl-phenoxy)-nicotinic acid methyl ester 1H NMR (CDCl$_3$) d 8.71(d,2H), 7,1–7.4(m,5H), 6.82(s, 2H), 5.55(s,1H), 5.229s,1H), 4.29(d,1H), 3.97(d,1H), 3.869s,3H), 3.61(d,1H), 2.25(s,3H), 2.01(s,6H), 1.91(s,3H), 1.65(s,3H), 1.61(s,3H) ppm.

2-(4-Chloro-2,6-dimethyl-phenoxy)-4-(S)-(1-hydroxymethyl-propylamino)-6-methyl-nicotinic acid ethyl ester 1H NMR(CDCl$_3$) d 8.01(d,1H), 7.02(s,2H), 6.17(s,1H), 4.33(q,2H), 3.71(m,1H), 3.66(m,1H), 3.54m,1H), 2.10(s, 3H), 2.07(s,6H), 1.5–1.8(m,2H), 1.33(t,3H), 1.00(t,3H) ppm.

4-[Ethyl-(2-methoxy-ethyl)-amino]-6-methyl-2-(2,4,6-trimethyl-phenoxy)-nicotinic acid methyl ester 1H NMR(CDCl$_3$) d 6.83(s,2H), 6.19(s,1H), 3.869s,3H), 3.35–3.6(m,4H), 3.35(s,3H), 2.26(s,3H), 2.15(s,3H), 2.06(s, 6H), 1.179t,3H) ppm.

2-(4-Chloro-2,6-dimethyl-phenoxy)-4-(S,R)-&(S,S)-(1-ethyl-2-hydroxy-propylamino)-6-methyl-nicotinic acid methyl ester 1H NMR(CDCl$_3$) d 8.2(d,1H), 7.01(s2H), 6.20(s, 0.2H), 6.15(s,0.8H), 3.92(m,1H), 3.87(s,3H), 3.48(m,0.2H), 3.31 (m,0.8H), 2.08(s,3H), 2.06(s,6H), 1.5–1.8(m,2H), 1.25(d, 3H), 0.96(t,3H) ppm.

2-(4-Chloro-2,6-dimethyl-phenoxy)-4-(R)-(1-hydroxymethyl-propylamino)-6-methyl-nicotinic acid methyl ester 1H NMR(CDCl$_3$) 8.12(d,1H), 7.00(s,2H), 6.16(s,1H), 3.85(s,3H), 3.6–3.8(m,2H), 3.53(m,1H), 2.08(s,3H), 2.05(s, 6H), 1.5–1.8(m,2H), 0.98(t,3H)ppm.

4-(2-Hydroxy-1-hydroxymethyl-ethylamino)-6-methyl-2-(2,4,6-trimethyl-phenoxy)-nicotinic acid methyl ester 1H NMR(CDCl$_3$) d 8.44(d,1H), 6.84(s,2H), 6.17(s,1H), 3.8–4.0(m,4H), 3.85(s,3H), 3.70(m,1H), 2.60(s,3H), 2.27(s, 3H), 2.11(s,2H), 2.05(s,6H) ppm.

4-(2-Methoxy-1-methoxymethyl-ethylamino)-6-methyl-2-(2,4 6-trimethyl-phenoxy)-nicotinic acid methyl ester 1H NMR(CDCl$_3$) d 8.38(d,1H), 6.88(s,2H), 6.18(s,1H), 3.88(s,3H), 3.78(m,1H), 3.56(m,2H), 3.44(s,6H), 2.31(s, 3H), 2.15(s,3H), 2.09(s,6H) ppm.

4-(1-Hydroxymethyl-2-methoxy-ethylamino)-6-methyl-2-(2,4,6-trimethyl-phenoxy)-nicotinic acid methyl ester 1H NMR(CDCl$_3$) d 8.44(d,1H), 6.88(s,2H), 6.21(s,1H), 3.89(s,3H), 3.80(m,1H), 3.5–3.7(m,2H), 3.45(s,3H), 2.31(s, 3H), 2.16(s,3H), 2.09(s,6H) ppm.

2-(4-Chloro-2,6-dimethyl-phenoxy)-4-(1-ethyl-2-hydroxy-butylamino)-6-methyl-nicotinic acid methyl ester 1H NMR (CDCl$_3$) d 8.34(d,1H), 7.069s,2H), 6.16(s,1H), 3.91(s,3H), 3.70(m,1H), 3.5(m, 1H), 2.13(s,3H), 2.11 (s,6H), 1.5–1.9(m,4H), 1.01 (m,6H) ppm.

EXAMPLE 24

[2-(4-Chloro-2,6-dimethyl-phenoxy)-4-(1-ethyl-propylamino)-6-methyl-pyridin-3-yl]-methanol A mixture of 4-(1-ethyl-propylamino)-6-methyl-2-(2,4,6-trimethyl-phenoxy)-nicotinic acid methyl ester (130 mg, 0.332 mmol) and an excess of 1M diisobutyl aluminum hydride in THF in dry THF was stirred at −78° C. for 10 min, then warmed to rt. The mixture was quenched with methanol and stirred at room temperature for 20 min, filtered through celite and washed with methanol and chloroform. The filtrate was concentrated to dryness. The residue was purified through silica gel column chromatography to give the title compound. 1HNMR(CDCl$_3$) d 7.03(s,2H), 6.11(s,1H), 5.03(d,1H), 4.96(s,2H), 3.32(m,1H), 2.14(s,3H), 2.07(s,6H), 1.4–1.7(m,4H), 0.96(t,6H) ppm.

[2-(4-Bromo-2,6-dimethyl-phenoxy)-4-(1-ethyl-propylamino)-6-methyl-pyridin-3-yl]-methanol The title compound was prepared by the method analogous to that in the preceding paragraph. 1H NMR(CDCl$_3$) d 7.18(s,2H), 6.11(s,1H), 5.05(d,1H), 4.91(d,2H), 3.31(m, 1H), 2.14(s,3H), 2.07(s,6H), 1.4–1.7(m,4H), 0.96(t,6H) ppm.

EXAMPLE 25

2-[3-Hydroxymethyl-6-methyl-2-(2,4,6-trimethyl-phenoxy)-pyridin-4-(S)-ylamino]-butan-1-ol A mixture of 4-(s)-(1-hydroxymethyl-propylamino)-6-methyl-2-(2,4,6-trimethyl-phenoxy)-nicotinic acid methyl ester and 1M lithium aluminum hydride and aluminum chloride in THF in dry THF was heated at reflux. The mixture was cooled and quenched with water, 2N NaOH, then of water and stirred at room temperature for 10 min. White solid formed and was filtered through celite, washed with THF. The filtrate was concentrate to dryness to give the title compound as a white solid after column chromatography, mp. 135–137° C.; Anal. For $C_{20}H_{28}N_2O_3$ calc. C, 69.74; H, 8.19; N, 8.13; found C, 69.42; H, 8.34; N, 7.95

The following compounds were prepared by a method analogous to that in the preceding paragraph, starting with the corresponding ester and reaction thereof with lithium aluminum hydride and aluminum chloride.

3-[2-(4-Chloro-2,6-dimethyl-phenoxy)-3-hydroxymethyl-6-methyl-pyridin-4-ylamino]-pentan-2ol mp. 180–182° C. 1H NMR(CDCl$_3$) 7.0(s,2H), 6.18&6.15 (two sets of s,1H), 5.1 and 5.22(m,1H), 4.92(m,2H), 3.80–4.0(m,1H), 3.20–3.5(m,1H), 2.11(s,3H), 2.04(s,6H), 1.4–1.8(m,2H), 1.23(m,3H), 0.98(m,3H) ppm.

2-[2-(2,6-Dimethyl-phenoxy)-3-hydroxymethyl-6-methyl-pyridin-4-ylamino]-butan-1-ol 1H (CDCl$_3$) d 7.05(m,3H), 6.20(s,1H), 4.8–5.0(m,2H), 3.74(m,1H), 3.66(m,1H), 3.50(m,1H), 2.0–2.29m,9H), 1.55–1.75(m,2H), 0.99(t,3H) ppm.

3-[3-Hydroxymethyl-6-methyl-2-(2,4,6-trimethyl-phenoxy)-pyridin-4-ylamino]-pentan-2-ol 1H NMR(CDCl$_3$) d 6.86(s,2H), 6.17(s, 1H), 4.0(d,1H), 3.9(m,1H), 3.3(m,1H), 2.29(s,3H), 2.14(s,3H), 2.13(s,3H), 2.07(s,6H), 1.8(d,1H), 1.4–1.8(m,2H), 1.25(d,3H), 0.99(t, 3H) ppm.

2-[2-(4-Chloro-2-methoxy-phenoxy )-3-hydroxymethyl-6-methyl-pyridin-4-ylamino]-butan-1-ol 1H NMR(CDCl$_3$) 6.8–7.0(m,3H), 6.2(s,1H), 5.02(d,1H), 4.7(ABq,2H), 3.74(m,5H), 3.350–3.5(m,2H), 2.9(brs,2H), 2.18(s,3H), 1.4–1.7(m,2H), 1.23(m,3H), 0.95(t,3H) ppm.

EXAMPLE 26

2-[2-(4-Chloro-2,6-dimethyl-phenoxy)-3-hydroxymethyl-6-methyl-pyridin-4-ylamino]-butan-1-ol A mixture of 4-(s)-(1-hydroxymethyl-propylamino)-6-methyl-2-(4-chloro-2,6-dimethyl-phenoxy)-nicotinic acid methyl ester and 1M lithium aluminum hydride in THF was stirred at rt for 2 hr. The mixture was cooled and quenched with water, 2N NaOH, then of water and stirred at room temperature for 10 min. White solid formed and was filtered through celite washed with THF. The filtrate was concentrated to dryness to give the title compound as a white solid after column chromatography, mp 133–135° C., 1H NMR (CDCl$_3$) 7.00(s,2H), 6.17(s,1H), 5.12(d,1H), 4.90(m,2H), 3.4–3.8(m,3H), 2.12(s,3H), 2.04(s,6H), 1.4–1.6(m,2H), 0.99 (t,3H) ppm.

The following compounds were prepared by the method analogous to that in the preceding paragraph, starting with the corresponding methyl ester with lithium aluminum hydride:

2-{Ethyl-[3-hydroxymethyl-6-methyl-2-(2,4,6-trimethyl-phenoxy)-pyridin-4-yl]-amino}-ethanol 1H NMR(CDCl$_3$) d 1H NMR(CDCl$_3$) 6.86(s,2H), 6.53 (s,1H), 4.94(s,2H), 3.67(m,2H), 3.1–3.3 (m,4H), 2.28(s,3H), 2.20(s,3H), 2.04(s,6H), 1.09(t,3H) ppm.

4-[2-(4-Chloro-2,6-dimethyl-phenoxy)-3-hydroxymethyl-6-methyl-pyridin-4-ylamino]-hexan-3-ol mp. 145–148° C. 1H NMR(CDCl$_3$) d 1H NMR(CDCl$_3$) 7.05(s,2H), 6.16(s,1H), 5.3(d,1H), 4.94(s,2H), 3.67(m,1H), 3.40 (m,1H), 2.151(s,3H), 2.09(s,6H), 1.4–1.8(m,4H), 1.23 (m,3H), 1.02(m,6H) ppm.

2-[2-(4-Chloro-2-methoxy-phenoxy)-3-hydroxymethyl-6-methyl-pyridin-4-(S)-ylamino]-butan-1-ol 1H NMR (CDCl$_3$) d 7.8–7.95(m,2H), 5.02(d,1H), 4.74 (ABq,2H), 3.74(s,3H), 3.72(m,2H), 3.45m,1H), 2.98(brs, 1H), 2.18(s,3H), 1.4–1.7(m,2H), 0.95(t,3H) ppm.

4-[2-(4-Chloro-2,6-dimethyl-phenoxy)-3-hydroxymethyl-6-methyl-pyridin-4-ylamino]-hexan-3-ol 1H NMR (CDCl$_3$) d 7.05(s,2H), 6.16(s,1H), 5.30(d,1H), 4.94(s,2H), 3.67(m,1H), 3.4(m,1H), 2.15(s,3H), 2.09(s,6H), 1.5–1.9(m,4H), 1.01(m,6H) ppm.

[2-(2,4-Dimethoxy-phenylamino)-4-(1-methoxymethyl-propoxy)-6-methyl-pyridin-3-yl]-methanol 1H NMR(CDCl$_3$) d 6.90(d,1H), 6.42(s,1H), 6.40(d,1H), 5.91(s,1H), 4.42(m,1H), 4.28(s,2H), 3.79(s,3H), 3.76(s,3H), 3.56(m,2H), 3.40(s,3H), 2.33(s,3H), 1.5–1.85(m,2H,), 1.02 (t,3H) ppm.

EXAMPLE 27

2-(4-Chloro-2,6-dimethyl-phenoxy)-4-(S)-(1-hydroxymethyl-propylamino)-6-methyl-nicotinic acid A mixture of 2-(4-chloro-2,6-dimethyl-phenoxy)-4-(S)-(1-hydroxymethyl-propylamino)-6-methyl-nicotinic acid methyl ester (113 mg) and lithium hydroxide in dioxane/THF/water was stirred at room temperature over night. The mixture was quenched with ammonium chloride and extracted with chloroform. The organic layer was dried and concentrated to give 78 mg of the title compound as a white solid. 1H NMR(CDCl$_3$) d 10.55(brs,1H), 9.2(d,1H), 7.06(s, 2H), 6.3(s,1H), 3.5–3.8(m,3H), 2.11(s,3H), 2.09(s,3H), 2.08 (s,3H), 1.78(m,1H), 1.62(m,1H), 1.00(t,3H) ppm.

4-(1-Ethyl-prop-2-ynylamino)-6-methyl-2-(2,4,6-trimethyl-phenoxy)-nicotinic acid mp. 131–133° C., 1H NMR(CDCl$_3$) d 11.29(brs,1H), 9.35(d,1H), 6.91 (s,2H), 6.38(s,1H), 4.12(m,1H), 2.88(m, 1H), 2.32(s,3H), 2.19(s,3H), 2.09(s,6H), 1.96(m,2H), 1.17 (t,6H) ppm.

2-(4-Bromo-2,6-dimethyl-phenoxy)-4-(S)-(1-methoxymethyl-propylamino)-6-methyl-nicotinic acid 1H NMR (CDCl$_3$) d 10.5(brs, 1H), 8.6(d,1H), 7.15(d,2H), 6.25(s,1H), 3.3–3.6(m,3H), 3.38(s,3H), 2.11 (s,3H), 2.09(s, 3H), 2.08(s,3H), 1.5–1.85(m,2H), 0.91(t,3H) ppm.

4-(2-Methoxy-1-methoxymethyl-ethylamino)-6-methyl-2-(2,4,6-trimethyl-phenoxy)-nicotinic acid 1H NMR(CDCl$_3$) d 9.44(d,1H), 6.92(s,2H), 6.30(s,1H), 3.80(m,1H), 3.58(m,2H), 3.44(s,6H), 2.33(s,3H), 2.16(s, 3H), 2.10(s,6H) ppm.

EXAMPLE 28

The following compounds were prepared by reacting the corresponding [2-(substituted-phenoxy)-3-chloromethyl-6-methyl-pyridin-4-yl]-(alkyl)-amine with an appropriate amine.

[2-(4-Chloro-2,6-dimethyl-phenoxy)-3-isobutoxymethyl-6-methyl-pyridin-4-yl]-(1-ethyl-propyl)-amine 1H NMR(CDCl$_3$) d 6.94(s,2H), 6.0(s,1H), 5.13(d,1H), 4.7(s,2H), 3.2(m,1H), 3.16(d,2H), 2.02(s,3H), 1.96(s,6H), 1.8(m,1H), 1.3–1.6(m,4H), 0.82(t,6H), 0.8(d,6H) ppm.

[3-Ethoxymethyl-6-methyl-2-(2,4,6-trimethyl-phenoxy)-pyridin-4-yl]-(1-ethyl-propyl)-amine 1H NMR (CDCl$_3$) d 6.86(s,2H), 6.03(s,1H), 5.30(d,1H), 4.83(s,2H), 3.58(q,2H), 3.35(m,1H), 2.29(s,3H), 2.15(s,3H), 2.06(s,6H), 1.5–1.78(m,4H), 1.23(t,3H), 0.967(t,6H)ppm.

2-[3-Butoxymethyl-6-methyl-2-(2,4,6-trimethyl-phenoxy)-pyridin-4-ylamino]-butan-1-ol 1H NMR(CDCl$_3$) d 6.85(s,2H), 6.179s,1H), 5.3(d,1H), 4.82(Abq,2H), 3.5–3.8(m,2H), 3.5(t,2H), 2.3(s,3H), 2.15(s, 3H, 2.02(s,6H),1.75(brs,1H), 1.5–1.8(m,4H), 1.3–1.5(m, 2H), 1.02(t,3H), 0.9(t,3H) ppm.

EXAMPLE 29

1-[4-(1-Ethyl-propylamino)-6-methyl-2-(2,4,6-trimethyl-phenoxy)-pyridin-3-yl)-ethanol The title compound was prepared by reacting 4-(1-ethyl-propylamino)-6-methyl-2-(2,4,6-trimethyl-phenoxy)-pyridine-3-carbaldehyde with methyllithium lithium in THF at −78° C. The desired product was isolated after silica gel column chromatography to give 60.1% of a colorless oil. 1H NMR(CDCl$_3$) d 6.87(s,2H), 6.06(s,1H), 5.7(q,1H), 3.3(m, 1H), 2.29(s,3H), 2.12(s,6H), 2.069s,3H), 1.4–1.7(m,4H), 1.59(d,3H), 0.8–1.0(m,6H) ppm.

EXAMPLE 30

Acetic acid 4-(1-ethyl-propylamino)-6-methyl-2-(2,4,6-trimethyl-phenoxy)-pyridin-3-ylmethyl ester The title compound was obtained by acetylation of [2-(2,4,6-trimethyl-phenoxy)-3-hydroxymethyl-6-methyl-pyridin-4-yl]-(1-ethyl-propyl)-amine.

1H NMR(CCl$_3$) d 6.84(s,2H), 6.04(s,1H), 5.35(s,2H), 5.23(d,1H), 3.32(m,1H), 2.28(s,3H), 2.12(s,3H), 2.08(s,3H), 2.07(s,6H), 1.4–1.7(m,4H), 0.93(t,6H) ppm.

EXAMPLE 31

2-[2-(4-Chloro-2,6-dimethyl-phenoxy)-3-(1-hydroxy-1-methyl-ethyl )-6-methyl-pyridin-4-(S)-ylamino]-butan-1-ol The title compound was prepared by reacting 2-(4-chloro-2,6-dimethyl-phenoxy) 4-(1-hydroxymethyl-propylamino)-6-methyl-nicotinic acid methyl ester with an excess of 1M methyl magnesium bromide in THF at room temperature overnight. Standard work-up procedure gave the title compound after silica gel chromatography.

1H NMR(CDCl$_3$) d 7.4(brs,1H), 7.01(s,2H), 6.13(s,1H), 3.7(m,1H), 3.6(m,1H), 3.45(m,1H), 2.04(s,3H), 2.03(s,3H), 2.02(s,3H), 1.5–1.7(m,2H), 0.98(t,3H) ppm.

EXAMPLE 32

[2-(4-Chloro-2,6-dimethyl-phenoxy)-3,6-dimethyl-pyridin-4-yl]-(1-ethyl-propyl)-amine To a solution of [2-(4-Chloro-2,6-dimethyl-phenoxy)-3-chloromethyl-6-methyl-pyridin-4-yl]-(1-ethyl-propyl)-amine (75 mg, 0.196 mmol) in dry THF was added 1.0M BH$_3$ in THF (0.59 ml, 0.59 mmol) and stirred for 2 hr. The mixture was quenched with dilute HCl and stirred for 5 min. The reaction mixture was neutralized with 2N NaOH, water and extracted with ethyl acetate. The organic layer was separated, dried and concentrated to dryness. The residue was purified through silca gel column chromatography to give the title compound as a colorless oil.

1H NMR(CDCl$_3$) d 7.03(s,2H), 6.08(s,1H), 3.73(d,1H), 3.3(m,1H), 2.15(s,3H), 2.12(s,3H), 2.08(s,6H), 1.4–1.6(m, 4H), 0.96(t,6H) ppm.

EXAMPLE 33

[2-(2,6-Dimethyl-phenoxy)-3,6-dimethyl-pyridin-4-yl]-(1-ethyl-propyl )-amine

To a solution of [2-(4-bromo-2,6-dimethyl-phenoxy)-4-(1-ethyl-propylamino)-6-methyl-pyridin-3-yl]-methanol (43 mg, 0.106 mmol) in dry THF was added 1.0M lithium aluminum hydride in diethyl ether (0.25 ml) and aluminum chloride (28 mg). The resulting mixture was stirred at room temperature overnight. The mixture was quenched with water, 2NaOH, then water. Solid formed and filtered through celite, washed with THF, then chloroform. The filtrate was concentrated to dryness. The residue was diluted with water and ethyl acetate. The organic layer was separated, dried and concentrated to give the crude material. The title compound was isolated after silca gel chromatography. 1H NMR (CDCl$_3$) d 6.9–7.1(m,3H), 6.07(s,1H), 3.35(d,1H), 3.33(m, 1H), 2.14(s,3H), 2.13(s,3H), 2.12(s,6H), 1.5–1.8(m,4H), 0.97(t,6H) ppm.

EXAMPLE 34

[2-(4-Bromo-2,6-dimethyl-phenoxy)-3,6-dimethyl-pyridin-4-yl]-(1-ethyl-propyl)-amine The title compound was prepared by the method analogous to that in Example 145 as a white solid. 1H NMR(CDCl$_3$) d 7.19(s,2H), 6.09(s,1H), 3.36(d,1H), 3.33(m,1H), 2.15(s, 3H), 2.12(s,3H), 2.09(s,6H), 1.4–1.8(m,4H), 0.97(t,6H) ppm.

EXAMPLE 35

4-[4-(1-Ethyl-propylamino)-3,6-dimethyl-pyridin-2-yloxy]-3,5-dimethyl-benzaldehyde To a solution of [2-(4-bromo-2,6-dimethyl-phenoxy)-3,6-dimethyl-pyridin-4-yl]-(1-ethyl-propyl)-amine in dry THF was added n-butyllithium at −78° C. After stirring at −78° C. for 10 min, n,N-dimethylformamide was added and the resulting mixture was stirred at −78° C. for 20 min, the dry-ice bath was removed. After stirring for 5 min, the mixture was quenched with diluted HCl, water and adjusted to pH7.5 and extracted with ethyl acetate. The organic layer was separated, dried, and concentrated to dryness. The residue was purified through silica gel chromatography to give the title compound. 1H NMR(CDCl$_3$) d 9.93(s,1H), 7.60(s,2H), 6.10(s,1H), 3.75(d,1H), 3.35(m1H), 2.17(s,6H), 2.13(s,3H), 2.12(s,3H), 1.4–1.8(m,4H), 0.97(t,6H) ppm.

EXAMPLE 36

{4-[4-(1-Ethyl-propylamino)-3,6-dimethyl-pyridin-2-yloxy]-3,5-dimethyl-phenyl}-methanol A mixture of 4-[4-(1-Ethyl-propylamino)-3,6-dimethyl-pyridin-2-yloxy]-3,5-dimethyl-benzaldehyde and sodium borohydride in methanol was stirred at room temperature. After standard work-up procedure and purification, the title compound was obtained as a solid. 1H NMR(CDCl$_3$) d 7.06(s,2H), 6.08(s,1H), 4.64(s,2H), 3.74(d,1H), 3.33(m,1H), 2.14(s,3H)., 2.13(s,3H), 2.11(s,6H) ppm.

EXAMPLE 37

(1-Ethyl-propyl)-[2-(4-methoxymethyl-2,6-dimethyl-phenoxy)-3,6-dimethyl-pyridin-4-yl]-amine To a solution of {4-[4-(1-Ethyl-propylamino)-3,6-dimethyl-pyridin-2-yloxy]-3,5-dimethyl-phenyl}-methanol in dry THF was added 60% NaOH in oil and stirred for 5 min. Excess of MeI was added and stirred at room temperature for 2 hr. After standard worked up procedure and purification, the title compound was obtained as a clear golden oil. 1H NMR(CDCl$_3$) d 7.02(s,2H), 6.06(s,1H), 4.40(s,3H), 3.72(d,1H), 3.39(s,3H), 3.36(m,1H), 2.12(s,3H), 2.11(s,3H), 2.10(s,6H), 1.4–1.7(m,4H), 0.95(t,6H) ppm.

EXAMPLE 38

[2-(4-Ethyl-2,6-dimethyl-phenoxy)-3,6-dimethyl-pyridin-4-yl]-(1-ethyl-propyl)-amine To a solution of [2-(4-bromo-2,6-dimethyl-phenoxy)-3,6-dimethyl-pyridin-4-yl]-(1-ethyl-propyl)-amine in dry THF was added n-butyllithium at –78° C. After stirring at –78° C. for 10 min, ethyl iodide was added and the resulting mixture was stirred at –78° C. for 30 min, the dry-ice bath was removed. After stirring for 5 min, the mixture was quenched with brine and extracted with ethyl acetate. The organic layer was separated, dried, and concentrated to dryness. The residue was purified through silica gel chromatography to give the title compound. 1H NMR(CDCl$_3$) d 6.89(s,2H), 6.07(s,1H), 3.72(d,1H), 3.34(m,1H), 2.58(q,2H), 2.16(s,3H), 2.12(s,3H), 2.09(s,6H), 1.4–1.7(m,4H), 1.25(t,3H), 0.96(t,6H) ppm.

EXAMPLE 39

2-{4-[4-(1-Ethyl-propylamino)-3,6-dimethyl-pyridin-2-yloxy]-3,5-dimethyl-phenyl}-propan-2-ol To a solution of [2-(4-bromo-2,6-dimethyl-phenoxy)-3,6-dimethyl-pyridin-4-yl]-(1-ethyl-propyl)-amine in dry THF was added n-butyllithium at –78° C. After stirring at –78° C. for 10 min, acetone was added and the resulting mixture was stirred at –78° C. for 30 min. The dry-ice bath was removed. After stirring for 5 min, the mixture was quenched with brine and extracted with ethyl acetate. The organic layer was separated, dried, and concentrated to dryness. The residue was purified through silica gel chromatography to give the title compound. 1H NMR(CDCl$_3$) d 7.17(s,2H), 6.08(s,1H), 3.73(d,1H), 3.33(m,1H), 2.19(s,3H), 2.15(s,3H), 2.12(s,6H), 1.4–1.7(m,4H), 1.26(s,6H), 0.96(t,6H) ppm.

EXAMPLE 40

1-{4-[4-(1-Ethyl-propylamino)-3,6-dimethyl-pyridin-2-yloxy]-3,5-dimethyl-phenyl}-ethanol To a solution of [2-(4-bromo-2,6-dimethyl-phenoxy)-3,6-dimethyl-pyridin-4-yl]-(1-ethyl-propyl)-amine in dry THF was added n-butyllithium at –78° C. After stirring at –78° C. for 10 min, acetaldehyde was added and the resulting mixture was stirred at –78° C. for 30 min, the dry-ice bath was removed. After stirring for 5 min, the mixture was quenched with brine and extracted with ethyl acetate. The organic layer was separated, dried, and concentrated to dryness. The residue was purified through silica gel chromatography to give the title compound. 1H NMR(CDCl$_3$) d 7.06(s,2H), 4.84(m,1H), 6.08(s,1H), 3.73(d,1H), 3.35(m, 1H), 2.14(s,3H), 2.12(s,3H), 2.11 (s,6H), 1.4–1.7(m,4H), 1.51 (d,3H), 0.96(t,6H) ppm.

EXAMPLE 41

(1-Ethyl-propyl)-[2-(4-isopropenyl-2,6-dimethyl-phenoxy)-3,6-dimethyl-pyridin-4-yl]-amine The title compound was prepared by reacting of 2-{4-[4-(1-Ethyl-propylamino)-3,6-dimethyl-pyridin-2-yloxy]-3,5-dimethyl-phenyl}-propan-2-ol with Burgess Inner salt (Et$_3$NS(O)$_2$NCOOMe) in benzene at reflux for 30 min. 1H NMR(CDCl$_3$) d 7.17(s,2H), 6.08(s,1H), 5.34(s,1H), 5.02(s, 1H), 3.72(d,1H), 3.32(m,1H), 2.12 and 2.15 (two sets of s, 12H), 1.4–1.6(m,4H), 0.97(t,6H) ppm.

EXAMPLE 42

(1-Ethyl-propyl)-[2-(4-isopropyl-2,6-dimethyl-phenoxy)-3,6-dimethyl-pyridin-4-yl]-amine The title compound was prepared by hydrogenation of (1-ethyl-propyl)-[2-(4-isopropenyl-2,6-dimethyl-phenoxy)-3,6-dimethyl-pyridin-4-yl]-amine using 10% Pd/C as catalyst in ethyl acetate at 55 psi until all starting material were consumed. The title compound was obtained as an oil after purification. 1H NMR(CDCl$_3$) d 6.93(s,2H), 6.10(s,1H), 3.73(brs,1H), 3.36(m,1H), 2.18(s,3H), 2.14(s,3H), 2.12(s, 6H), 1.4–1.8(m,4H), 1.27(d,6H), 0.98(t,6H) ppm.

EXAMPLE 43

[3,6-Dimethyl-2-(2,4,6-trimethyl-phenoxy)-pyridin-4-yl]-(1-ethyl- allyl)-amine

The title compound was prepared as a clear oil by reduction of 4-(1-Ethyl-prop-2-ynylamino)-6-methyl-2-(2, 4,6-trimethyl-phenoxy)-nicotinic acid with lithium aluminum hydride and aluminum chloride. 1H NMR(CDCl$_3$) d 6.87(s,2H), 6.08(s,1H), 5.7–5.9(m,1H), 5.1-5.3(m,2H), 3.75–4.0(m,2H), 2.30(s,3H), 2.16(s,3H), 2.15(s,3H), 2.08(s, 6H), 1.70(m,2H), 1.03(t,3H)ppm.

EXAMPLE 44

(1-Ethyl-propyl)-[2-(4-fluoro-2,6-dimethyl-phenoxy)-3,6-dimethyl-pyridin-4-yl]-amine To a solution of [2-(4-bromo-2,6-dimethyl-phenoxy)-3,6-dimethyl-pyridin-4-yl]-(1-ethyl-propyl)-amine in dry THF was added n-butyllithium at −78° C. After stirring at −78° C. for 10 min, (PhSO2)2NF was added and the resulting mixture was stirred at −78° C. for 30 min, the dry-ice bath was removed. After stirring for 5 min, the mixture was quenched with brine and extracted with ethyl acetate. The organic layer was separated, dried, and concentrated to dryness. The residue was purified through silica gel chromatography to give the title compound. 1H NMR(CDCl$_3$) d 6.77(s,1H), 6.73(s,1H), 6.08(s,1H), 3.3(m,1H), 2.12(s,3H), 2.09(s,6H), 2.08(s,3H), 1.4–1.8(m,4H), 0.97(t,6H)ppm.

EXAMPLE 45

2-[2-(2,6-Dimethyl-phenoxy)-3,6-dimethyl-pyridin-4-ylamino]-butan-1-ol

The title compound was prepared by the method analogous to that in Example 33.

1H NMR(CDCl$_3$) d 7.05(m,3H), 6.24(s,1H), 3.4–3.8(m, 3H), 2.24(s,3H), 2.16(s,3H), 2.10(s,6H), 1.5–1.8(m,2H), 0.99(t3H)ppm.

EXAMPLE 46

2-[3,6-Dimethyl-2-(2,4,6-trimethyl-phenoxy)-pyridin-4-(S)-ylamino]-butan-1-ol

To a solution of 2-(2,4,6-trimethyl-phenoxy)-4-(1-hydroxymethyl-propylamino)-6-methyl-nicotinic acid methyl ester in dry THF was added 1.0M lithium aluminium hydride in diethyl ether (0.25 ml) and aluminum chloride. The resulting mixture was heated at reflux for 2 hr. The mixture was quenched with of water, 2NaOH, then water and stirred. Solid formed and was filtered through celite, then washed with water and ethyl acetate. The organic layer was separated, dried, concentrated, and purification to give the title compound as a white solid. Anal. For C$_{20}$H$_{28}$N$_2$O$_2$·½H$_2$O calc. C, 70.90; H, 8.52; N, 8.01; found C, 71.18; H, 8.66; N, 8.30

The following compounds were prepared by the method analogous to that in the preceding paragraph, using the corresponding 2-(substituted phenoxy)-4-(alkyl-amino)-6-methyl-nicotinic acid methyl ester with lithium aluminum hydride and aluminum chloride.

3-[3,6-Dimethyl-2-(2,4,6-trimethyl-phenoxy)-pyridin-4-ylamino]-pentan-2-ol

1H NMR(CDCl$_3$) d 6.86(s,2H), 6.17&6.13(two sets of s, 1H), 5.0–5.2(m,1 H), 4.9(s,2H), 3.9–4.1(m,1H), 3.5(m,1H), 3.3(m,1H), 2.29(s,3H), 2.14(s,3H), 2.08(s,6H), 1.4–1.8(m, 2H), 1.27(m,3H), 0.98(m,3H) ppm.

3-[2-(4-Chloro-2,6-dimethyl-phenoxy)-3,6-dimethyl-pyridin-4-ylamino]-pentan-2-ol 1H NMR(CDCl$_3$) d 7.01(s,2H), 6.14&6.11(two sets of s,1H), 4.04&3.82(two sets of d,1H), 3.92(m,1H), 3.4&3.2 (m,1H), 2.13(s,3H), 2.11(s,3H), 2.05(s,6H), 1.4–1.8(m,2H), 1.25(two sets of d, 3H), 0.98&0.96(two sets of t,3H) ppm.

EXAMPLE 47

Benzyl-[3,6-dimethyl-2-(2,4,6-trimethyl-phenoxy)-pyridin-4-yl]-ethyl-amine

A mixture of 4-bromo-3,6-dimethyl-2-(2,4,6-trimethyl-phenoxy)-pyridine (250 mg, 0.78 mmol), benzylethylamine (127 mg, 0.937 mmol), Pd(OAc)2(3.6 mg, 0.0156 mmol), (S)-2,2'-bis(diphenylphosphino)-1,1'-binaphthyl (BINAP) (9.7 mg, 0.0156 mmol), potassium t-butoxide (105 mg, 0.781 mmol) in 25 ml of toluene was heated at reflux for 2 hr. The mixture was cooled to rt, quenched with water and extracted with ethyl acetate. The organic layer was separated, dried (Na$_2$SO$_4$), filtered, and concentrated to give a brown oil. The crude material was purified through silica gel column chromatography to give the title compound. 1H NMR(CDCl$_3$) d 7.2–7.4(m,5H), 6.86(s,2H), 6.41(s,1H), 4.23(s,2H), 3.07(q,2H), 2.31(s,3H), 2.29(s,3H), 2.16(s,3H), 2.06(s,6H), 1.05(t,3H) ppm.

The following compounds were prepared by the method analogous to that in the preceding paragraph, using an appropriate 4-bromo-2-(substituted phenoxy)-3-methyl-6-alkyl or alkoxy-pyridine with an appropriate amine.

[2-(4-Chloro-2,6-dimethyl-phenoxy)-3,6-dimethyl-pyridin-4-yl]-(1-methoxymethyl-propyl)-amine 1H NMR(CDCl$_3$) d 7.06(s,2H), 6.13(s,1H), 4.14(d,1H), 3.3-3.6(m,3H), 3.42(s,3H), 2.16(s,3H), 2.14(s,3H), 2.09(s, 6H), 1.5–1.8(m,2H0, 1.03(t,3H) ppm.

2-[3,6-Dimethyl-2-(2,4,6-trimethyl-phenoxy)-pyridin-4-ylamino]-3-phenyl-propan-1-ol 1H NMR(CDCl$_3$) d 8.6(d,1H), 7.2–7.4(m5H), 6.84(s,2H), 6.169s,1H), 4.099d,1H), 3.82(m,1H), 3.5–3.7(m,2H), 2.95 (d,2H), 2.96(s,3H), 2.27(s,3H), 2.14(s,3H), 2.05(s,6H) ppm.

[2-(4-Chloro-2,6-dimethyl-phenoxy)-3,6-dimethyl-pyridin-4-yl]-(1-methoxymethyl-propyl)-amine 1H NMR(CDCl$_3$) d 7.06(s,2H), 6.13(s,1H), 4.2(m,1H), 3.53(m,2H), 3.42(s,3H), 2.19(s,3H), 2.14(s,3H), 2.10(s,6H), 1.5–1.8(m,2H), 1.03(t,3H) ppm.

[2-(4-Chloro-2,6-dimethyl-phenoxy)-3,6-dimethyl-pyridin-4-yl]-(1-ethoxymethyl-propyl)-amine 1H NMR(CDCl$_3$) d 7.06(s,2H), 6.14(s,1H), 4.24(d,1H), 4.4–4.65(m,5H), 2.19(s,3H), 2.14(s,3H), 2.10(s,6H), 1.8(m, 1H), 1.65(m,1H), 1.25(t,3H), 1.03(t,3H) ppm.

[3,6-Dimethyl-2-(2,4,6-trimethoxy-phenoxy)-pyridin-4-yl]-(1-methoxymethyl-propyl)-amine 1H NMR(CDCl$_3$) d 6.20(s,2H), 6.08(s,1H), 3.80(s,3H), 3.73(s,6H), 3.8(m,2H), 3.39(m,1H), 3.36(s,3H), 2.23(brs, 3H), 2.10(s,3H), 1.74(m,1H), 1.59(m,1H), 0.969t,3H) ppm.

[2-(4-Bromo-2,6-dimethyl-phenoxy)-3-methoxy-6-methyl-pyridin-4-yl]-(1-ethy-propyl)-amine 1H NMR(CDCl$_3$) d 7.18(s,2H), 6.09(s,1H), 4.43(d,1H), 3.89(s,3H), 3,25(m,1H), 2.10(s,9H), 1.4–1.8(m,4H), 0.95(t, 6H) ppm.

(1-Ethyl-propyl)-[3-methoxy-6-methyl-2-(2,4,6-trimethyl-phenoxy)-pyridin-4-yl]-amine 1H NMR(CDCl$_3$) d6.85(s,2H), 6.07(s,1H), 4.44(m,1H), 3.89(s,3H), 3.23(m,1H), 2.27(s,3H), 2.09(s,6H), 2.08(s,3H), 1.65(m,2H), 1.45(m,2H), 0.93(m,6H) ppm.

[2-(4-Chloro-2,6-dimethyl-phenoxy)-6-methyl-3-propyl-pyridin-4-yl]-(1-ethyl-propyl)-amine

[2-(4-Bromo-2,6-dimethyl-phenoxy)-6-methyl-3-propyl-pyridin-4-yl]-(1-ethyl-propyl)-amine 1H NMR(CDCl$_3$) d 7.03(s,2H), 6.13(s,1H), 3.8(m,1H), 3.74(s,2H), 3.38(m,1H), 2.15(s,3H), 2.05(s,6H), 1.50–1.7 (m,4H), 0.97(t,6H) ppm.

(1-Ethyl-propyl)-[6-methyl-3-propyl-2-(2,4,6-trimethyl-phenoxy)-pyridin-4-yl]-amine

[2-(2,4-Dichloro-6-methyl-phenoxy)-3-methoxy-6-methyl-pyridin-4-yl]-(1-ethyl-propyl)-amine 1H NMR(CDCl$_3$) 7.24(d,1H), 7.1(d,1H), 6.1(s,1H), 4.47 (d,1H), 3.9(s,3H), 3.22(m,1H), 2.12(s,3H), 2.08(s,3H), 1.4–1.7(m,4H), 0.9(t,6H) ppm.

[2-(4-Chloro-2,6-dimethyl-phenoxy)-3-methoxy-6-methyl-pyridin-4-yl]-(1-ethyl-propyl)-amine 1H NMR(CDCl$_3$) 7.02(s,2H), 6.07(s,1H), 4.44(brs,1H), 3.8–3.95(m,3H), 3.23(m,1H), 2.09(s,6H), 2.08(s,3H), 1.4–1.7(m,4H), 0.93(t,6H)ppm.

[2-(4-Chloro-2,6-dimethyl-phenoxy)-3-methoxy-6-methyl-pyridin-4-yl]-(1-methoxymethyl-propyl)-amine 1H NMR(CDCl$_3$) d 7.02(s,2H), 6.11(s,1H), 4.71(d,1H), 3.88(s,3H), 3.45(m,2H), 3.37(s,3H), 2.10(s,3H), 2.09(s,6H), 1.73(m,1H), 1.59(m,1H), 0.98(m,3H) ppm.

[2-(2,4-Dichloro-6-methyl-phenoxy)-3-methoxy-6-methyl-pyridin-4-yl]-(1-methoxymethyl-propyl)-amine 1H NMR (CDCl$_3$) d 7.1–7.25(m,2H), 6.13(s,1H), 4.74(d, 1H), 3.91(s,3H), 3.47(m,1H), 3.39(m,2H), 3.37(s,3H), 2.14 (s,3H), 2.10(s,3H), 1.78(m,1H), 1.59(m, 1H), 0.98(t,3H) ppm.

[2-(4-Chloro-2-methoxy-phenoxy)-3-methoxy-6-methyl-pyridin-4-yl]-(1-methoxymethyl-propyl)-amine 1H NMR (CDCl$_3$) d 6.8–7.0(m,3H), 6.17(s,1H), 4.76(d, 1H), 3.82(s,3H), 3.75(s,3H), 3.3–3.5(m,3H), 3.35(s,3H), 2.19(s,3H), 1.73(m,1H), 1.56(m,1H), 0.96(t,3H) ppm.

[2-(3-Chloro-2,6-dimethoxy-phenoxy)-3-methoxy-6-methyl-pyridin-4-yl]-(1-methoxymethyl-propyl)-amine 1H NMR(CDCl$_3$) d 7.12(d,1H), 6.64(d,1H), 6.12(s,1H) <4.73(d,1H), 3.88(s,3H). 3.78(s,3H), 3.70(s,3H), 3.3–3.5(m, 3H), 3.35(s,3H), 2.11(s,3H), 1.5–1.8(m,2H), 0.96(t,3H) ppm.

(1-Methoxymethyl-propyl)-[3-methoxy-6-methyl-2-(2,4,6-trimethoxy-phenoxy)-pyridin-4-yl]-amine 1H NMR(CDCl$_3$) d 6.19(s,2H), 6.10s,1H), 4.75(m,1H), 3.87(s,3H), 3.80(s,3H), 3.73(s,6H), 3.3–3.5(m,2H), 3.35(s, 3H), 2.17(s,3H), 1.78(m,1H), 1.5(m,1H), 0.96(t,3H) ppm.

[3-Methoxy-2-(4-methoxy-2,6-dimethyl-phenoxy)-6-methyl-pyridin-4-yl]-(1-ethoxymethyl-propyl)-amine 1H NMR(CDCl$_3$) d 6.59(s,2H), 6.10(s,1H), 4.70(d,1H), 3.89s,3H), 3.77(s,3H), 3.48(m,1H), 3.39(m,2H), 3.37(s,3H), 2.11 (s,3H), 2.10(s,6H), 1.74(m,1H), 1.57(m,1H), 0.98(t, 3H) ppm.

[2-(4-Chloro-2,6-dimethyl-phenoxy)-3-ethoxy-6-methyl-pyridin-4-yl]-(1-methoxymethyl-propyl)-amine 1H NMR(CDCl$_3$) d 7.07(s,2H), 6.16(s,1H), 4.82(d,1H), 4.20(q,2H), 3.54(m,1H), 3.43(m,2H), 3.42(s,3H), 2.15(s, 3H), 2.13(s,6H), 1.5–1.9(m,2H), 1.439t,3H), 1.02(t,3H) ppm.

EXAMPLE 48

2-[2-(4-Chloro-2,6-dimethyl-phenoxy)-3,6-dimethyl-pyridin-4-(S)-ylamino]-butan-1-ol To a solution of [1-(tert-butyl-dimethyl-silanyloxymethyl)-propyl]-[2-(4-chloro-2,6-dimethyl-phenoxy)-3,6-dimethyl-pyridin-4-yl]-amine in dry THF was added 1M tetrabutylammonium fluoride in THF at room temperature. The mixture was stirred at room temperature for 2 hr, quenched with water, extracted with ethyl acetate. The organic layer was separated, dried and concentrated to dryness. The residue was purified by Biotage using 15% ethyl acetate in hexane as eluent to give the title compound as a white solid. 1H NMR(CDCl$_3$) d 7.06(s,2H), 6.18(s,1H), 4.04(d,1H), 3.74(m,1H), 3.69(m,1H), 3.53(m,1H), 2.18(s, 3H), 2.16(s,3H), 2.10(s,6H), 1.6–1.8(m,2H), 1.04(t,3H) ppm.

The following compounds were prepared by the method analogous to that in the preceding paragraph, starting with the corresponding tert-butyl-dimethyl-silanyloxymethyl derivative with tetrabutylammonium fluoride.

2-[3-Methoxy-6-methyl-2-(2,4,6-trimethyl-phenoxy)-pyridin-4-(S)-ylamino]-butan-1-ol 1H NMR (CDCl$_3$) d 6.85(s,2H), 6.15(s,1H), 4.57(d,1H), 3.91(s,3H), 3.72(m,1H), 3.61(m,1H), 3.41(m,1H), 2.27(s, 3H), 2.10(s,3H), 2.07(s,6H), 1.5–1.8(m,3H), 0.98(t,3H) ppm.

2-[2-(4-Chloro-2,6-dimethyl-phenoxy)-3-methoxy-6-methyl-pyridin4-ylamino]-butan-1ol 1H NMR(CDCl$_3$) d 7.02(s,2H), 6.16(s,1H), 4.60(d,1H), 3.91(s,3H), 3.71(m,1H), 3.61(m,1H), 3.40(m,1H), 2.10(s, 3H), 2.08(s,6H), 1.8(brs,1H), 1.71(m,1H), 1.68(m,1H), 0.99 (t,3H) ppm.

4-[4-(1-Hydroxymethyl-propylamino)-3-methoxy-6-methyl-pyrid in-2-yloxy]-3,5-dimethyl-benzonitrile 1H NMR(CDCl$_3$) d 7.35(s,2H), 6.19(s,1H), 4.7(brs,1H), 3.88(s,3H), 3.731(m,1H), 3.64(m,1H), 3.43(m,1H), 2.14(m, 9H), 1.8(brs,1 H), 1.71 (m,1H), 1.58(m,1H), 0.99(t,3H) ppm.

EXAMPLE 49

3-[2-(4-Chloro-2,6-dimethyl-phenoxy)-3,6-dimethyl-pyridin-4-ylamino]-pentan-2-ol The title compound was prepared by Dess Martin oxidation of 2-[2-(4-chloro-2,6-dimethyl-phenoxy)-3,6-dimethyl-pyridin-4-(S)-ylamino]-butan-1-ol methylene chloride at room temperature, followed by Gringard reaction using methyl magnesium bromide in THF.1H NMR(CDCl$_3$) d 7.07(s,2H), 6.18(s,1H), 4.3(brs,1H), 4.0(m,1H), 3.32(m, 1H), 2.22(s,3H), 2.17(s,3H), 2.11(s,6H), 1.6–1.8(m,2H), 1.30(d,3H), 1.01(t,3H)ppm.

EXAMPLE 50

2-[2-Methyl-6-(2,4,6-trimethyl-phenoxy)-pyridin-4-ylamino]-butan-1-ol

The title compound was prepared as an oil by heating 2-(2,4,6-trimethyl-phenoxy)-4-(S)-(1-hydroxymethyl-propylamino)-6-methyl-nicotinic acid in 160° C. until all starting material were consumed. Anal. For $C_{19}OH_{26}N_2O_2$ $H_2O$ calc. C, 68.65; H, 8.49; N, 8.42; found C, 69.04; H, 8.14; N, 8.91

EXAMPLE 51

(1-Ethyl-prop-2-ynyl)-[2-methyl-6-(2,4,6-trimethyl-phenoxy)-pyridin-4-yl]-amine]

The title compound was prepared by the method analogous to that in Example 163.

1H NMR(CDCl$_3$) d 6.89(s,2H), 6.12(d,1H), 5.41(d,1H), 3.9–4.2(m,2H), 2.37s,3H), 2.30(s,3H), 2.27(m,1H), 1.76(m, 2H), 1.05(t,3H) ppm.

EXAMPLE 52

2-(4-Bromo-2,6-dimethyl-phenoxy)-4-(1-ethyl-propylamino)-6-methyl-pyridin-3-ol

To a solution of [2-(4-bromo-2,6-dimethyl-phenoxy)-3-methoxy-6-methyl-pyridin-4-yl]-(1-ethy-propyl)-amine in methylene chloride was added BBr$_3$ at 0° C. and stirred for hr. The mixture was quenched with water and extracted with chloroform. The organic layer was separated, dried, and concentrated to give the title compound. 1H NMR(CDCl$_3$) d 7.20(s,2H), 6.12(s,1H), 4.77(d,1H), 3.27(m,1H), 2.13(s, 3H), 2.10(s,6H), 1.4–1.8(m, 4H), 0.97(t,6H) ppm.

The following compounds were prepared by the method analogous to that in the preceding paragraph, starting with an appropriate [2-(substituted phenoxy)-3-methoxy-6-methyl-pyridin-4-yl]-(alkyl)-amine with BBr$_3$ or BCl$_3$.

4-(1-Ethyl-propylamino)-6-methyl-2-(2,4,6-trimethyl-phenoxy)-pyridin-3-ol

1H NMR(CDCl$_3$) d6.85(s,2H), 6.10(s,1H), 5.12(brs,1H), 4.21(m,1H), 3.27(m,1H), 2.28(s,3H), 2.09(s,9H), 1.5–1.8 (m,4H), 0.96(m,6H) ppm.

4-(S)-(1-Hydroxymethyl-propylamino)-6-methyl-2-(2,4,6-trimethyl-phenoxy)-pyridin-3-ol 1H NMR (CDCl$_3$) d 6.85(s,2H), 6.17(s,1H), 5.13(brs,1H), 4.28(d,1H), 3.73(m,1H), 3.60(m,1H), 3.50(m,1H), 2.27(s, 3H), 2.12(s,3H), 2.07(s,6H), 1.75(brs,1H), 1.5–1.7(m,2H), 0.99(t,3H) ppm.

2-(4-Chloro-2,6-dimethyl-phenoxy)-4-(1-hydroxymethyl-propylamino)-6-methyl-pyridin-3-ol 1H NMR(CDCl$_3$) d 7.032(s,2H), 6.10(s,1H), 5.2(brs,1H), 4.35(brs,1H), 3.71(m,1H), 3.61 (m,1H), 3.40(m,1H), 2.07 (s,9H), 1.8(brs,1 H), 1.71 (m,1H), 1.60(m,1H), 0.99(m,3H) ppm.

2-(4-Chloro-2,6-dimethyl-phenoxy)-4-(1-ethyl-propylamino)-6-methyl-pyridin-3-ol

1H NMR(CDCl$_3$) d 7.02(s,2H), 6.10(s,1H), 5.02(brs,1H), 4.22(brs,1H), 3.25(brs,1H), 2.08(brs,9H), 1.62(m,2H), 1.52 (m,2H), 0.95(brs,6H) ppm.

EXAMPLE 53

Chloro-acetic acid 4-(1-ethyl-propylamino)-6-methyl-2-(2,4,6-trimethyl-phenoxy)-pyridin-3-yl ester The title compound was prepared by reacting 4-(1-ethyl-propylamino)-6-methyl-2-(2,4,6-trimethyl-phenoxy)-pyridin-3-ol with chloroacetyl chloride /triethylamine in THF at 0° C. to rt. 1H NMR(CDCl$_3$) d 6.84(s,2H), 6.15(s, 1H), 4.3(s,2H), 4.0(d,1H), 3.3(m,1H), 2.28(s,3H), 2.17(s, 3H), 2.08(s,6H), ⅙–1.7(m,4H), 0.9(t,6H) ppm.

EXAMPLE 54

2-(4-Chloro-2,6-dimethyl-phenoxy)-4-[(1-ethyl-propyl)-methyl-amino]-6-methyl-pyridin-3-ol 1H NMR(CDCl$_3$) d 7.03(s,2H), 6.25(s,1H), 5.4(brs,1H), 3.93(m,1H), 2.70(s,3H), 2.12(s,3H), 2.08(s,6H),1.55(m, 4H), 0.89(t,6H) ppm.

EXAMPLE 55

[4-(1-Ethyl-propylamino)-6-methyl-2-(2,4,6-trimethyl-phenoxy)-pyridin-3-yl]-acetonitrile 1H NMR(CDCl$_3$) d 6.87(s,2H), 6.13(s,1H), 3.83(d,1H), 3.79(S,2H), 3.38(m,1H), 2.30(s,3H), 2.27(s,3H), 2.21 (s,6H), 1.4–1.8(m,4H), 1.00(t,6H) ppm.

EXAMPLE 56

4-(1-Ethyl-propylamino)-6-methyl-2-(2,4,6-trimethyl-phenoxy)-pyridine-3-carbaldehyde 1H NMR(CDCl$_3$) d 10.52(s,1H), 9.26(d,1H), 6.89(s,2H), 6.11(s,1H), 3.42(m,1H), 2.31(s,3H0, 2.15(s,3H), 2.11 (s,6H), 1.45–1.75(m,4H), 0.97(t,6H) ppm.

EXAMPLE 57

(1-Ethyl-propyl)-[3-[(1-ethyl-propylimino)-methyl]-6-methyl-2-(2,4,6-trimethyl-phenoxy)-pyridin-4-yl]-amine 1H NMR(CDCl$_3$) d 10.33(d,1H), 8.94(s,1H), 6.89(s,2H), 6.10(s,1H), 3.41(m,1H), 2.86(m,1H), 2.99(s,3H), 2.14(s, 3H), 2.10(s,6H), 1.4–1.89 m,8H), 0.94(t,6H), 0.87(t,6H) ppm.

EXAMPLE 58

2-[4-(1-Ethyl-propylamino)-6-methyl-2-(2,4,6-trimethyl-phenoxy)-pyridin-3-ylmethyl]-malonic acid dimethyl ester To a solution of dimethylmalonate (60 mg, 0.44 mmol) and 60% NaH in oil (20 mg, 0.44 mmol) in dry THF was added [3-Chloromethyl-6-methyl-2-(2,4,6-trimethyl-phenoxy)-pyridin-4-yl]-(1-ethyl-propyl)-amine hydrogen chloride (50 mg, 0.146 mmol) at room temperature for 1 hr. The mixture was quenched with water and extracted with ethyl acetate. The organic layer was separated, dried and concentrated to dryness. The residue was purified through silica gel column chromatography to give the title compound as a clear oil. 1H NMR (CDCl$_3$) d 6.88(s,2H), 6.03(s,1H), 4.85(m,1H), 4.03(t,1H), 3.73(s,6H), 3.26(m,1H), 3.18(d, 2H), 2.30(s,3H), 2.13s,3H), 2.07(s,6H), 1.5–1.8(m,4H), 0.97 (t,6H)ppm.

EXAMPLE 59

2-[4-(1-Ethyl-propylamino)-6-methyl-2-(2,4,6-trimethyl-phenoxy)-pyridin-3-ylmethyl]-malonic acid diisopropyl ester The title was prepared by the method analogous to that in Example 581. 1H NMR (CDCl$_3$) d 6.87(s,2H), 6.03(s,1H), 5.10(m,2H), 4.90(d,1 H), 3.94(t,1H), 3.31(m,1H), 3.16(d, 2H), 2.30(s,3H), 2.13s,3H0, 2.08(s,6H), 1.5–1.8(m,4H), 1.1–1.3(two sets of d, 6H), 0.97(t,6H)ppm.

EXAMPLE 60

4-(1-Ethyl-propoxy)-6-methyl-3-nitro-2-(2,4,6-trimethyl-phenoxy)-pyridine

To a mixture of 2-chloro-4-(1-ethyl-propoxy)-6-methyl-3-nitro-pyridine (500 mg, 1.93 mmol) and 2,4,6- trimethylphenol (289 mg, 2.13 mmol) in dry THF was added potassium t-butoxide. The resulting mixture was stirred at rt. overnight. The mixture was quenched with water, brine and extracted 3 times with ethyl acetate. The organic layer was separated, dried (MgSO$_4$) and concentrated to dryness. After silica gel column chromatography purification, the title compound was obtained as a light yellow crystal, mp 106–109° C. Anal. For $C_{20}H_{26}N_2O_4$ calc. C, 67.02; H, 7.31; N, 7.82; found, C, 67.34; H, 7.40; N, 7.42.

EXAMPLE 61

4-(1-Ethyl-propoxy)-6-methyl-2-(2,4,6-trimethyl-phenoxy)-pyridin-3-ylamine

A mixture of 4-(1-ethyl-propoxy)-6-methyl-3-nitro-2-(2,4,6-trimethyl-phenoxy)-pyridine (150 mg, 0.418 mmol) and 10% Pd/C (23 mg) in ethanol was hydrogenated at 50 psi for 15 hours. An additional 10 Pd/C was added and the resulting mixture was hydrogenated for an additional 24 hr. The mixture was filtered through celite and the filtrate was concentrated to dryness to give 200 mg of the crude material. After column chromatography, the title compound was prepared as a the corresponding HCl salt as a white solid, mp 96–98° C.

EXAMPLE 62

[4-(1-Ethyl-propoxy)-6-methyl-2-(2,4,6-trimethyl-phenoxy)-pyridin-3-yl]-dimethyl-amine To a solution of 4-(1-ethyl-propoxy)-6-methyl-2-(2,4,6-trimethyl-phenoxy)-pyridin-3-ylamine in dry THF was added lithium bis(trimethylsilyl)amide at −78° C. After stirring at −78° C. for 10 minutes, an excess of methyl iodide was added. The title compound was isolated after quenching with water and extracting with ethyl acetate. The crude material was purified by silica gel column chromatography to give the title compound as a tan foam.

EXAMPLE 63

N-[4-(1-Ethyl-propoxy)-6-methyl-2-(2,4,6-trimethyl-phenoxy)-pyridin-3-yl]-succinamic acid A mixture of 4-(1-ethyl-propoxy)-6-methyl-2-(2,4,6-trimethyl-phenoxy)-pyridin-3-ylamine (100 mg, 0.304 mmol), succinic anhydride 31 mg, 0.304 mmol) and triethylamine in methylene chloride was stirred at rt. overnight. The mixture was quenched with water, and extracted with methylene chloride. The organic layer was separated, dried and concentrated to give a solid. The title compound was isolated as a white crystal after silica gel column chromatography.

1H NMR(CDCl$_3$) d 6.90(brs,1H), 6.84(s,2H), 6.37(s,1H), 4.2(m,1H), 2.6–2.8(m,4H), 2.28(s,3H), 2.22(s,3H), 2.03(s,6H), 1.69(m,4H), 0.94(t,6H) ppm.

EXAMPLE 64

4-(1-Ethyl-propoxy)-3,6-dimethyl-2-[3-(2,4,6-trimethyl-pyridinoxy)]-pyridine To a solution of 3-pentanol (0.11 ml) in dry THF was added sodium hydride (60% in oil, 20 mg). After stirring for 5 min, a solution of 4-chloro-2,5-dimethyl-6-[3-(2,4,6-trimethyl-pyridinoxy)]-pyridine (92 mg, 0.332 mmol) in THF was added. DMSO was added and the resulting mixture was heated at 130° C. oil bath overnight. The mixture was quenched with water, brine and extracted 3 times with ethyl acetate. The organic layer was separated, dried (MgSO$_4$) and concentrated to dryness. After silica gel column chromatography purification, the title compound was obtained as a clear oil. 1H NMR (CDCl$_3$) d 6.88 (s,1H), 6.37(s,1H), 4.21 (m,1H), 2.5(s,3H), 2.29(s,3H), 2.19(s,3H), 2.18(s,3H), 2.07 (s,3H), 1.70(m,4H), 0.98(t,6H) ppm. The oil was prepared as the corresponding HCl salt to give a white solid (63 mg).

The title compounds of the following Examples 65 and 66 were prepared by the methods analogous to that in Example 64, starting with an appropriate 6-alkyl-4-chloro-or bromo-3-methyl-2-(2,4,6-trimethyl-phenoxy)-pyridine with 3-pentanol/NaH:

EXAMPLE 65

6-Ethyl-4-(1-ethyl-propoxy)-3-methyl-2-(2,4,6-trimethyl-phenoxy)-pyridine

1H NMR(CDCl$_3$) d 6.87(s,2H), 6.28(s,1H), 4.20(m,1H), 2.46(q,2H), 2.30(s,3H) 2.20(s,3H), 2.07(s,6H), 1.72(m,4H), 1.05(t,3H), 0.99(t,6H) ppm.

EXAMPLE 66

4-(1-Ethyl-propoxy)-2-(4-fluoro-2,6-dimethyl-phenoxy)-3,6-dimethyl-pyridine colorless oil. Anal. For $C_{20}H_{26}FNO_2$ calc. C, 72.48; H, 7.91; N, 4.23; found C, 72.39; H, 7.77; N, 4.10.

EXAMPLE 67

[4-(1-Ethyl-propoxy)-3,6-dimethyl-pyridin-2-yl]-(2,4,6-trimethyl-phenyl)-amine To a solution of 4-(1-ethyl-propoxy)-6-methyl-2-(2,4,6-trimethyl-phenylamino)-nicotinic acid (240 mg, 0.673 mmol) in dry THF was added lithium aluminum hydride and aluminum chloride. The resulting mixture was heated at reflux for 3 hours. The mixture was quenched with 0.1 ml water and 0.1 ml 2N NaOH, then quenched with water and ethyl acetate. The organic layer was separated, dried and concentrated to give 250 mg of brown oil. After silica gel column chromatography, 170 mg(78%) of the title compound was obtained which was prepared as a HCl salt as a white solid, mp. 132–133° C. 1H NMR(CDCl$_3$) d 6.87(s,2H), 6.09(s,1H), 5.399brs,1H), 4.13(m,1H), 2.27(s,3H), 2.22(s,3H), 2.15(s,6H), 1.98(s,3H), 1.67(m,4H), 0.94(t,6H) ppm.

EXAMPLE 68

[4-(1-Ethyl-propoxy)-6-methyl-2-(2,4,6-trimethyl-phenylamino)-pyridin-3-yl-methanol To a solution of 4-(1-ethyl-propoxy)-6-methyl-2-(2,4,6-trimethyl-phenylamino)-nicotinic acid (100 mg, 0.281 mmol) in dry THF was added BH$_3$.DMS. The resulting mixture was heated at reflux overnight. The mixture was quenched with dilute HCl and stirred for 30 minutes, adjusted pH to 7.5–8.5, then extracted with ethyl acetate. The organic layer was separated, dried and concentrated to give 100 mg of brown oil. After silica gel column chromatography, 91 mg(95%) of the title compound was obtained as a white foam. Anal. For $C_{21}H_{30}N_2O_2 \cdot \frac{1}{2}H_2O$ cal. C, 71.76; H, 8.89; N, 7.97; found: C, 71.97; H, 8.90; N, 7.69.

EXAMPLE 69

[4-(1-Ethyl-propoxy)-6-methyl-2-(2,4,6-trimethyl-phenylamino)-pyridin-3-yl]-oxo-acetonitrile The title compound was prepared by reacting [4-(1-ethyl-propoxy)-6-methyl-2-(2,4,6-trimethyl-phenylamino)- pyridin-3-yl]-methanol with thionyl chloride in benzene, concentrated to dryness, followed by reacting with diethylaluminum cyanide. After standard workup procedure and silica gel column chromatography, the title compound was obtained as a yellow crystal, mp. 108–110° C.

1H NMR(CDCl$_3$) d 8.57(s,1H), 6.97(s,2H), 6.37(s,1H), 4.46(m,1H), 2.35(s,3H), 2.34(s,3H), 2.09(s,6H), 1.6–1.8(m, 4H), 0.99(t,6H) ppm.

EXAMPLE 70

[4-(1-Ethyl-propoxy)-6-methyl-2-(2,4,6-trimethyl-phenylamino)-pyridin-3-yl]-imidazol-1-yl-methanone To a solution of 4-(1-ethyl-propoxy)-6-methyl-2-(2,4,6-trimethyl-phenylamino)-nicotinic; acid (250 mg, 0.701 mmol) in 2 ml of DMF was added carbonyldiimidazole (190 mg, 1.19 mmol) and the resulting mixture was stirred at room temperature overnight. After standard workup procedure and silica gel column chromatography, 260 mg(91.2%) of the title compound was obtained as a golden crystal, mp. 120–122° C., Anal. For $C_{24}H_{30}N_4O_2 \cdot \frac{1}{4}H_2O$ calc: C, 70.13; H, 7.48; N, 13.63; Found: C, 70.06; H, 7.69; N, 13.37.

EXAMPLE 71

2-[4-(1-Ethyl-propoxy)-6-methyl-2-(2,4,6-trimethyl-phenylamino)-pyridin-3-yl]-propan-2-ol The title compound was prepared by reacting [4-(1-ethyl-propoxy)-6-methyl-2-(2,4,6-trimethyl-phenylamino)-pyridin-3-yl]-imidazol-1-yl-methanone with an excess MeMgBr in THF at rt. After standard workup procedure and silica gel column chromatography, the title compound was obtained as a tan solid, mp. 81–83° C.; Anal. For $C_{22}H_{30}N_2O_2 \cdot 1.5 \ H_2O$ calc.: C,69.49; H, 9.38; N, 7.04; found: C, 69.49; H, 9.27; N, 6.86

EXAMPLE 72

2-[4-(1-Ethyl-propoxy)-6-methyl-2-(2,4,6-trimethyl-phenylamino)-pyridin-3-ylmethyl]-malonic acid dimethyl ester The title compound was prepared by reacting [4-(1-ethyl-propoxy)-6-methyl-2-(2,4,6-trimethyl-phenylamino)-pyridin-3-yl]-methanol with thionyl chloride in benzene, concentrated to dryness, followed by reacting with methyl malonate/NaH in DMSO. After standard workup procedure and silica gel column chromatography, the title compound was obtained as a solid, mp. 96–98° C.; Anal. For $C_{26}H_{36}N_2O_5 \cdot \frac{1}{3}H_2O$ calc.: C, 67.51; H, 7.99; N, 6.04; found: C, 67.48; H, 7.99; N, 6.02.

EXAMPLE 73

3-[4-(1-Ethyl-propoxy)-6-methyl-2-(2,4,6-trimethyl-phenylamino)-pyridin-3-yl]-propionic acid Hydrolysis of 2-[4-(1-ethyl-propoxy)-6-methyl-2-(2,4,6-trimethyl-phenylamino)-pyridin-3-ylmethyl]-malonic acid dimethyl ester with phosphoic/water at reflux to give the title compound as a white foam. Anal. For $C_{23}H_{32}N_2O_3 \cdot \frac{3}{4}H_2O$ calc.: C,69.40; H, 8.48; N, 7.04; found: C, 69.17; H, 8.62; N, 6.90.

EXAMPLE 74

[3-Aminomethyl-4-(1-ethyl-propoxy)-6-methyl-pyridin-2-yl]-(2,4,6-trimethyl-phenyl)-amine The title compound was prepared by reacting [4-(1-ethyl-propoxy)-6-methyl-2-(2,4,6-trimethyl-phenylamino)-pyridin-3-yl]-methanol with thionyl chloride in benzene, concentrated to dryness, followed by reacting with NH$_3$(g) at room temperature. After standard workup procedure and silica gel column chromatography, the title compound was obtained as a golden oil (80%), Anal. For $C_{21}H_{31}N_3O$. calc.: C,73.86; H, 9.15; N, 12.3; found: C, 73.50; H, 9.25; N, 11.39.

EXAMPLE 75

2-Chloro-N-[4-(1-ethyl-propoxy)-6-methyl-2-(2,4,6-trimethyl-phenylamino)-pyridin-3-ylmethyl]-acetamide The title compound was prepared by acylation of 3-aminomethyl-4-(1-ethyl-propoxy)-6-methyl-pyridin-2-yl]-(2,4,6-trimethyl-phenyl)-amine with chloroacetyl chloride. After standard workup procedure and silica gel column chromatography, the title compound was obtained as an off-white crystal, mp. 142–144° C.; Anal. For $C_{23}H_{32}ClN_3O_2$. calc.: C, 66.09; H, 7.72; N, 10.05; found: C, 65.81; H, 7.64; N, 9.86.

EXAMPLE 76

[3-Dimethylaminomethyl-4-(1-ethyl-propoxy)-6-methyl-pyridin-2-yl]-(2,4,6-trimethyl-phenyl)-amine hydrochloride salt The title compound was prepared by reacting [4-(1-ethyl-propoxy)-6-methyl-2-(2,4,6-trimethyl-phenylamino)-pyridin-3-yl]-methanol with thionyl chloride in benzene, concentrated to dryness, followed by reacting with dimethylamine at room temperature. After standard work-up procedure and silica gel column chromatography, the title compound was obtained as an oil. The corresponding HCl salt was prepared as a white solid, mp. 85–88° C.; Anal. For $C_{23}H_{35}N_3O \cdot 2HCl \cdot 1.5 \ H_2O$ calc.: C,58.83; H, 8.588; N, 8.94; found: C, 58.32; H, 8.5327; N, 8.64.

EXAMPLE 77

Dithiocarbonic acid O-ethyl ester S-[4-(1-ethyl-propoxy)-6-methyl-2-(2,4,6-trimethyl-phenylamino)-pyridin-3-ylmethyl] ester The title compound was prepared by reacting [4-(1-ethyl-propoxy)-6-methyl-2-(2,4,6-trimethyl-phenylamino)-pyridin-3-yl]-methanol with thionyl chloride in benzene, concentrated to dryness, followed by reacting with NaSC-SOEt at room temperature. After standard work-up procedure and silica gel column chromatography, the title compound was obtained as a white solid, mp. 55–57° C.; Anal. For $C_{24}H_{34}N_2O_2S_2$. calc.: C, 64.54; H, 7.67; N, 6.27; found: C, 64.67; H, 7.78; N, 6.26.

EXAMPLE 78

4-(1-Ethyl-propoxy)-6-methyl-2-(2,4,6-trimethyl-phenylamino)-nicotinamide

The title compound was prepared by reacting 4-(1-ethyl-propoxy)-6-methyl-2-(2,4,6-trimethyl-phenylamino)-nicotinic acid with thionyl chloride in benzene, concentrated to dryness, followed by reacting with NH$_3$(g) at room temperature. After standard work-up procedure and silica gel column chromatography, the title compound was obtained as an oil. The corresponding HCl salt was prepared as an off-white solid, mp 185–187° C.; Anal. For $C_{21}H_{29}N_3O_2$. calc.: C,70.96; H, 8.22; N, 11.82; found: C, 71.30; H, 8.33; N, 11.78.

EXAMPLE 79

4-(1-Ethyl-propoxy)-6-methyl-2-(2,4,6-trimethyl-phenylamino)-nicotinonitrile

The title compound was prepared by reacting 4-(1-ethyl-propoxy)-6-methyl-2-(2,4,6-trimethyl-phenylamino)-nicotinamide with triphosgen/triethylamine in THF. mp 105–107° C., 1H NMR(CDCl3) d 6.90(s,2H), 6.26(brs,1H), 6.05(s,1H), 4.24(m,1 H), 2.28(s,3H), 2.25(s,3H), 2.17(s, 6H), 1.72(m,4H), 0.97(t,6H) ppm.

EXAMPLE 80

4-(1-Ethyl-propoxy)-6,N,N-trimethyl-2-(2,4,6-trimethyl-phenylamino)-nicotinamide The title compound was prepared by reacting 4-(1-ethyl-propoxy)-6-methyl-2-(2,4,6-trimethyl-phenylamino)-nicotinic acid with thionyl chloride in benzene, concentrated to dryness, followed by reacting with dimethylamine at room temperature. After standard work-up procedure and silica gel column chromatography, the title compound was obtained as an oil. The corresponding HCl salt was prepared as a white solid, mp. 197–200° C.; Anal. For $C_{23}H_{33}N_3O_2 \cdot H_2O$. calc.: C,63.07; H, 8.28; N, 9.59; found: C, 63.24; H, 8.07; N, 9.61.

EXAMPLE 81

[4-(1-Ethyl-propoxy)-6-methyl-2-(2,4,6-trimethyl-phenylamino)-pyridin-3-yl]-acetonitrile The title compound was prepared by reacting [4-(1-ethyl-propoxy)-6-methyl-2-(2,4,6-trimethyl-phenylamino)-pyridin-3-yl]-methanol with thionyl chloride in benzene, concentrated to dryness, followed by reacting with potassium cyanide in DMSO at room temperature. After standard work-up procedure and silica gel column chromatography, the title compound was obtained as a pale orange solid, mp. 112–115° C., 1H NMR(CDCl$_3$) d 6.9(s,2H), 6.14(s,1H), 5.6(brs,1H), 4.22(m,1H), 3.49(s,2H), 2.28(s,3H), 2.22(s, 3H), 2.16(s,6H), 1.71(m,4H), 0.95(t,6H) ppm.

EXAMPLE 82

[2-(4-Bromo-2,6-dimethyl-phenylamino)-4-(1-ethyl-propoxy)-6-methyl-pyridin-3-yl]-methanol To a solution of 4-(1-ethyl-propoxy)-6-methyl-2-(4-bromo-2,6-dimethyl-phenylamino)-nicotinic acid (130 mg, 0.309 mmol) in dry THF was added BH$_3$.DMS. The resulting mixture was heated at reflux overnight. The mixture was quenched with dilute HCl and stirred for 30 min, adjusted pH to 7.5–8.5, then extracted with ethyl acetate. The organic layer was separated, dried and concentrated to give 100 mg of brown oil. After silica gel column chromatography, 110 mg(87.3%) of the title compound was obtained as a white semi-solid. 1H NMR(CDCl$_3$) d 7.25(s,2H), 6.85(brs,1H), 4.8(brs,2H), 4.18(m,1H), 2.2(s,3H), 2.07(s,6H), 1.7(m,4H), 0.95(t,6H) ppm.

EXAMPLE 83

[2-(4-chloro-2,6-dimethyl-phenylamino)-4-(1-ethyl-propoxy)-6-methyl-pyridin-3-yl]-methanol To a solution of 4-(1-ethyl-propoxy)-6-methyl-2-(4-chloro-2,6-dimethyl-phenylamino)-nicotinic acid in dry THF was added BH$_3$.DMS. The resulting mixture was heated at reflux overnight. The mixture was quenched with dilute HCl and stirred for 30 minutes, adjusted pH to 7.5–8.5, then extracted with ethyl acetate. The organic layer was separated, dried and concentrated to give a brown oil. After silica gel column chromatography, the title compound was obtained as a green oil. 1H NMR(CDCl$_3$) d. 7.02(s,2H), 6.83(brs,1H), 4.78(s,2H), 4.14(m,1H), 2.2(s,3H), 2.13(s, 6H), 1.66(m,4H), 0.93(9t,6H) ppm.

EXAMPLE 84

[2-(2,4-Dichloro-phenylamino)-4-(1-ethyl-propoxy)-6-methyl-pyridin-3-yl]-methanol To a solution of 4-(1-ethyl-propoxy)-6-methyl-2-(2,4-dichloro-phenylamino)-nicotinic acid in dry THF was added BH$_3$.DMS. The resulting mixture was heated at reflux overnight. The mixture was quenched with dilute HCl and stirred for 30 min, adjusted pH to 7.5–8.5, then extracted with ethyl acetate. The organic layer was separated, dried and concentrated to give a golden oil. After silica gel column chromatography, the title compound was obtained as a golden oil. 1H NMR(CDCl$_3$) d 8.44(d,1H), 8.18(s,1H), 7.32(d,1H), 7.179d,1H), 6.28(s,1H), 4.82(s,2H), 4.21(m, 1H), 2.42(s,3H), 1.6–1.8(m,4H), 0.94(t,6H) ppm.

EXAMPLE 85

[2-(2,4-Dimethoxy-phenylamino)-4-(1-methoxymethyl-propoxy)-6-methyl-pyridin-3-yl]-methanol The title compound was prepared by a method analogous to that described for Example 84, starting with the corresponding nicotinic acid with BH$_3$.DMS. 1H NMR(CDCl$_3$) d 6.91(d,1H), 6.50(m,2H),5.91(s,1H), 4.42(m,1H), 4.281(s, 2H), 3.79(s,3H), 3.76(s,3H), 3.56(m,2H), 3.40(s,3H), 2.33 (s,3H), 1.6–1.8(m,2H), 1.02(t,3H) ppm.

EXAMPLE 86

[4-(1-Ethyl-propylamino)-6-methyl-2-(2,4,6-trimethyl-phenoxy)-pyridin-3-yl]-imidazol-1-yl-methanone The title compound was prepared by a method analogous to that described for Example 70, starting with the corresponding nicotinic acid with carbonyldiimidazole. 1HNMR (CDCl$_3$) d 8.1(s,1H), 7.52(s,1H), 7.05(s,1H), 6.78(s,2H), 6.17(s,1H), 5.97(d,1H), 3.3(m,1H), 2.23(s,3H), 2.18(s,3H), 2.00(s,6H), 1.4–1.7(m,4H), 0.93(t,6H)ppm.

EXAMPLE 87

1-[4-(1-Ethyl-propylamino)-6-methyl-2-(2,4,6-trimethyl-phenoxy)-pyridin-3-yl]-ethanone The title compound was prepared by reacting [4-(1-Ethyl-propylamino)-6-methyl-2-(2,4,6-trimethyl-phenoxy)-pyridin-3-yl]-imidazol-1-yl-methanone with methylmagnesium bromide/ethyl ether in methylene chloride. 1H NMR (CDCl$_3$) d 9.7(d,1H), 6.88(s,2H), 6.10(s,1H), 3.32(m,1H), 2.73(s,3H), 2.31(s,3H), 2.10(s,3H), 2.09(s,6H), 1.5–1.7(m, 4H), 0.95(t,6H)ppm.

EXAMPLE 88

(1-Ethyl-propyl)-[6-methyl-3-propyl-2-(2,4,6-trimethyl-phenoxy)-pyridin-4-yl]-amine 1H NMR(CDCl$_3$) d 6.84(s,2H), 6.04(s,1H), 3.81(d,1H), 3.31(m,1H), 2.56(t,2H), 2.27(s,3H), 2.12(s,3H), 2.04(s,6H), 1.4–1.7(6H), 1.02(t,3H), 0.93(t,6H) ppm.

EXAMPLE 89

2-[4-(1-Ethyl-propylamino)-6-methyl-2-(2,4,6-trimethyl-phenoxy)-pyridin-3-ylmethyl]-2-methyl-malonic acid dimethyl ester The title compound was prepared by a method analogous to that described for Example 72. 1H NMR(CDCl$_3$) 6.87(s, 2H), 6.01(s,1H), 5.05(m,1H), 3.70(s,6H), 3.4(s,2H), 3.3(m, 1H), 2.27(s,3H), 2.12(s,3H), 2.07(s,6H), 1.4–1.7(m,4H), 1.48(s,3H), 0.949t,6H) ppm.

EXAMPLE 90

[4-(1-Ethyl-propoxy)-6-methyl-pyridin-2-yl]-(2,4,6-trimethyl-phenyl)-amine

The title compound was prepared by decarboxylation of the corresponding nicotinic acid at 160° C. oil bath. mp. 98–100° C.; Anal. For $C_{20}H_{28}N_2O$ calc. C, 76.88; H, 9.03; N, 8.97; found: C, 76.97; H, 9.21; N, 8.99.

The following title compounds of Examples 204 and 205 were prepared by reacting of 3-methoxy-6-methyl-2-(2,4,6-trimethyl-phenoxy)-pyridine4-carbaldehyde with alkyl-magnesium bromide in THF:

EXAMPLE 91

2-Ethyl-1-[3-methoxy-6-methyl-2-(2,4,6-trimethyl-phenoxy)-pyridin-4-yl]-butan-1-ol 1H NMR(CDCl$_3$) 6.87(s,2H), 6.72(s,1H), 4.90(t,1H), 4.00(s,3H), 2.29(s,3H), 2.19(s,3H), 2.06(s,6H), 1.2–1.6(m, 5H), 0.92(t,3H), 0.88(t,3H) ppm.

EXAMPLE 92

1-[3-Methoxy-6-methyl-2-(2,4,6-trimethyl-phenoxy)-pyridin-4-yl]-2-methyl-butan-1-ol 1H NMR(CDCl$_3$) 6.88(s,2H), 6.74(s,1H), 5.00(m,1H), 4.00(s,3H), 2.29(s,3H)., 2.19(s,3H), 2.06(s,6H), 1.4–1.9(m, 3H), 0.992(t,3H), 0.989(d,3H) ppm.

EXAMPLE 93

1-[3,6-Dimethyl-2-(2,4,6-trimethyl-phenoxy)-pyridin-4-yl]-propan-1-ol

To a −78° C. solution of 4-bromo-3,6-dimethyl-2-(2,4,6-trimethyl-phenoxy)-pyridine in dry THF was added nBuLi and stirred at that temperature for 20 minutes. Excess propionaldehyde was added and stirred for 2 hours at −78° C. The mixture was quenched with water, extracted with ethyl acetate. The organic layer was washed with brine, dried and concentrated. After column chromatography, an off-white solid was obtained, mp. 119–120° C.1H NMR (CDCl$_3$) d 6.86(s,3H), 4.90(m,1H), 2.281(s,3H), 2.28(s,3H), 2.21(s,3H), 2.02(s,6H), 1.65–1.8(m,2H), 1.00(t,3H) ppm.

EXAMPLE 94

4-(1-Methoxy-propyl )-3,6-dimethyl-2-(2,4,6-trimethyl-phenoxy)-pyridine

The title compound was prepared by reaction of 1-[3,6-Dimethyl-2-(2,4,6-trimethyl-phenoxy)-pyridin-4-yl]-propan-1-ol with sodium hydride, followed by quenching with methyl iodide. 1H NMR(CDCl$_3$) d 6.87(s,2H), 6.74(s, 1H), 4.33(m,1H), 3.25(s,3H), 2.28(s,3H), 2.27(s,3H), 2.21 (s,3H), 2.03(s,6H), 1.6–1.8(m,2H), 0.94(t,3H) ppm.

EXAMPLE 95

4-(1-Ethoxy-propyl)-3,6-dimethyl-2-(2,4,6-trimethyl-phenoxy)-pyridine

The title compound was prepared by reaction of 1-[3,6-Dimethyl-2-(2,4,6-trimethyl-phenoxy)-pyridin-4-yl]-propan-1-ol with sodium hydride, followed by quenching with ethyl iodide.

1H NMR(CDCl$_3$) d 6.86(s,2H), 6.77(s,1H), 4.41(m,1H), 3.22–3.45(m,2H), 2.28(s,3H), 2.27(s,3H), 2.21(s,3H), 2.03 (s,6H), 1.6–1.8(m,2H), 1.20(t,3H), 0.95(t,3H) ppm.

EXAMPLE 96

4-(1-Allyloxy-propyl )-3,6-dimethyl-2-(2,4,6-trimethyl-phenoxy)-pyridine

The title compound was prepared by reaction of 1-[3,6-Dimethyl-2-(2,4,6-trimethyl-phenoxy)-pyridin-4-yl]-propan-1-ol with sodium hydride, followed by quenching with allyl bromide.

1H NMR(CDCl$_3$) d 6.87(s,2H), 6.78(s,1H), 5.93(m,1H), 5.1–5.3(m,2H), 4.48(m,1H), 3.95(m,1H), 3.76(m,1H), 2.29 (s,3H), 2.26(s,3H), 2.21(s,3H), 2.03(s,6H), 1.6–1.8(m,2H), 0.96(t,3H) ppm.

EXAMPLE 97

4-(1-Butoxy-propyl)-3,6-dimethyl-2-(2,4,6-trimethyl-phenoxy)-pyridine

The title compound was prepared by reacting of 1-[3,6-Dimethyl-2-(2,4,6-trimethyl-phenoxy)-pyridin-4-yl]-propan-1-ol with sodium hydride, followed by quenching with butyl iodide.

1H NMR(CDCl$_3$) d 6.86(s,2H), 6.76(s,1H), 4.37(m,1H), 3.35(m,1H), 3.25(m,1H), 2.28(s,3H), 2.26(s,3H), 2.20(s, 3H), 2.03(s,6H), 1.6–1.8(m,2H), 1.5–1.65(m,2H), 1.3–1.5 (m,2H), 0.96(t,3H), 0.89(t,3H) ppm.

The title compounds of the following Examples 98 through 102 were prepared by a method analogous to that described in Example 93 starting with an appropriate 4-bromo-2-(substituted-phenoxy)-pyridine derivative with nBuLi, followed by quenching with an appropriate aldehyde.

EXAMPLE 98

1-[2-(2,4-Dichloro-6-methyl-phenoxy)-3-methoxy-6-methyl-pyridin-4-yl]-2-ethyl-butan-1-ol one racemate 1H NMR(CDCl$_3$) d 7.28(d,1H), 7.14(d,1H), 6.80(s,1H), 4.92(d,1H), 4.00(s,3H), 2.21(s,3H), 2.13(s,3H), 1.3–1.65(m,5H), 0.93(t,3H), 0.87(t,3H) ppm.

The other racemate 1H NMR (CDCl$_3$) d 7.18(s,1H), 7.08(d,1H), 6.74(d,1H), 5.17(m,1H), 3.93(s,3H), 2.75(m, 1H), 2.1–2.25(m,1H), 2.16(s,3H), 2.13(s,3H), 1.6–1.8(m, 2H), 1.0–1.3(m,2H), 0.93(t,3H), 0.72(t,3H) ppm.

EXAMPLE 99

1-[3,6-Dimethyl-2-(2,4,6-trimethyl-phenoxy)-pyridin-4-yl]-2,2,2-trifluoro-ethanol mp. 134–139° C., Anal. For $C_{18}H_{20}F_3NO_2$ calc.: C, 63.71; H, 5.94; N, 4.13; found: C, 63.59; H, 6.00; N, 4.02.

EXAMPLE 100

1-[2-(4-Chloro-2,6-dimethyl-phenoxy)-3,6-dimethyl-pyridin-4-yl]-2,2,2-trifluoro-ethanol 1H NMR(CDCl$_3$) d 6.979s,2H), 6.19(s,1H), 2.14(s,6H), 2.06(s,6H) ppm.

EXAMPLE 101

[2-(4-Chloro-2,6-dimethyl-phenoxy)-3,6-dimethyl-pyridin-4-yl]-pyridin-2-yl-methanol 1H NMR(CDCl$_3$) d 8.61(d,1H), 7.71(m,1H), 7.30(m,1H), 7.10(m,1H), 7.03(s,2H),6.70(s,1H), 6.03(s,1H), 2.37(s,3H), 2.16(s,3H), 2.03(s,6H), ppm.

EXAMPLE 102

1-[2-(4-Chloro-2,6-dimethyl-phenoxy)-3-methoxy-6-methyl-pyridin-4-yl]-2-ethyl-butan-1-ol 1H NMR(CDCl$_3$) d 7.05(s,2H), 6.759s,1H), 4.90(t,1H), 3.98(s,3H), 2.19(s,3H), 2.06(s,6H), 2.13(d,1H), 1.25–1.65 (m,5H), 0.92(t,3H), 0.87(t,3H) ppm.

The title compounds of the following Examples 103 through 106 were prepared by oxidation of the corresponding alcohol with Dess Martin reagent in DMSO/methylene chloride or pyridinium chlorochromate in methylene chloride.

EXAMPLE 103

1-[3,6-Dimethyl-2-(2,4,6-trimethyl-phenoxy)-pyridin-4-yl]-propan-1-one mp. 82–85.5° C., Anal. For C$_{19}$H$_{25}$NO$_2$ calc.: C, 76.74; H, 7.80; N, 4.71; Found: C, 76.61; H, 7.94; N, 4.66.

EXAMPLE 104

1-[2-(4-Chloro-2,6-dimethyl-phenoxy)-3,6-dimethyl-pyridin-4-yl]-2,2,2-trifluoro-ethanone 1H NMR(CDCl$_3$) d 7.06(s,2H), 6.99(s,1H), 2.42(s,3H), 2.30(s,3H), 2.03(s,6H) ppm.

EXAMPLE 105

[2-(4-Chloro-2,6-dimethyl-phenoxy)-3,6-dimethyl-pyridin-4-yl]-pyridin-2-yl-methanone 1H NMR(CDCl$_3$) d 8.72(d,1H), 8.17(d,1H), 7.95(m,1H), 7.52(m,1H), 7.05(s,2H),6.75(s,1H), 2.25(s,3H), 2.22(s,3H), 2.07(s,6H) ppm.

EXAMPLE 106

1-[2-(4-Chloro-2,6-dimethyl-phenoxy)-3-methoxy-6-methyl-pyridin-4-yl]-2-ethyl-butan-1-one 1H NMR(CDCl$_3$) d 7.05(s,2H), 6.67(s,1H), 3.98(s,3H), 3.09(m,1H), 2.61(s,3H), 2.06(s,6H), 1.76(m,2H), 1.51 (m,2H), 0.92(t,6H) ppm.

EXAMPLE 107

4-(1-Ethoxy-2,2,2-trifluoro-ethyl)-3,6-dimethyl-2-(2,4,6-trimethyl-phenoxy-pyridine The title compound was prepared by reacting the corresponding alcohol with NaH, followed by quenching with ethyl iodide.

1H NMR(CDCl$_3$) d 6.92(s,1H), 6.87(s,2H), 4.92(m,1H), 3.60(m2H), 2.349s,3H), 2.29(s,3H), 2.26(s,3H), 2.03(s,6H), 1.26(t,3H) ppm.

The title compounds of the following Examples 108 through 109 were prepared by reacting of the corresponding ketone with alkyl lithium or alkyl magnesium.

EXAMPLE 108

2-[3,6-Dimethyl-2-(2,4,6-trimethyl-phenoxy)-pyridin-4-yl]-butan-2-ol

1H NMR(CDCl$_3$) d 6.86(m,3H), 2.48(s,3H), 2.28(s,3H), 2.21(s,3H), 2.02(s,6H), 1.8–2.1(m,2H), 1.61(s,3H), 0.84(t, 3H) ppm.

EXAMPLE 109

3-[3,6-Dimethyl-2-(2,4,6-trimethyl-phenoxy)-pyridin-4-yl]-pentan-3-ol

1H NMR(CDCl$_3$) d 6.87(s,1H), 6.86(s,2H), 2.43(s,3H), 2.28(s,3H0, 2.21(s,3H), 2.0–2.2(m,2H), 2.02(s,6H), 1.7–1.9 (m,2H), 1.69(brs,1H), 0.8(t,6H) ppm.

EXAMPLE 110

1-[2-(4-Chloro-2,6-dimethyl-phenoxy)-3-hydroxy-6-methyl-pyridin-4-yl]-2-ethyl-butan-1-one The title compound was prepared by reacting 1-[2-(4-Chloro-2,6-dimethyl-phenoxy)-3-methoxy-6-methyl-pyridin-4-yl]-2-ethyl-butan-1-one with BBr$_3$ or BCl$_3$ in THF or methylene chloride.

1H NMR (CDCl$_3$) d 7.04(s,2H), 7.01(s,1H), 3.26(m,1H), 2.24(s,3H), 2.08(s,6H), 1.80(m,2H), 1.63(m,2H), 0.91 (t,6H) ppm.

EXAMPLE 111

4-(1-Ethyl-propylamino)-6-methyl-2-(2,4,6-trimethyl-phenoxy)-nicotinamide

To a solution of 4-(1-ethyl-propylamino)-6-methyl-2-(2, 4,6-trimethyl-phenoxy)nicotinic acid in anhydrous methylene chloride was added thionyl chloride. After stirring for 1 hr, the reaction mixture was concentrated to dryness. The residue was dissolved in dry THF and NH3(g) was bubbled in. The reaction mixture was quenched with water and extracted with ethyl acetate. The organic layer was separated, dried and concentrated to give a light yellow solid. The solid was purified through silica gel column chromatography using 1% methanol in chloroform as eluent to give the title compound as a white solid, mp. 85–88° C.

1H NMR(CDCl$_3$) d 9.69(brs,1H), 8.01(brs,1H), 6.87(s,2H), 6.11(s,1H), 5.48(brs,1H), 3.31(m,1H), 2.29(s,3H), 2.10(s, 3H), 2.07(s,6H), 1.60(m,4H), 0.95(t,6H) ppm.

The title compounds of the following Examples 112 through 118 were prepared by a method analogous to that described in the preceding paragraph, starting with the corresponding nicotinic acid or pyrimidine-5-carboxylic derivative and quenching with an appropriate nucleophile.

EXAMPLE 112

4-(1-Ethyl-propylamino)-6,N-dimethyl-2-(2,4,6-trimethyl-phenoxy)-nicotinamide

1H NMR(CDCl$_3$) d 9.8(brs,1H), 8.21(brs,1H), 6.88(s, 2H), 6.11(s,1H), 3.31(m,1H), 2.92(d,3H), 2.30(s,3H), 2.10 (s,3H), 2.07(s,6H), 1.60(m,4H), 0.95(t,6H) ppm.

EXAMPLE 113

2-(4-Chloro-2,6-dimethyl-phenoxy)-4-(S)-(1-hydroxymethyl-propylamino)-6-methyl-nicotinamide 1H NMR(CDCl$_3$) d 9.7(d,1H), 7.9(brs,1H), 7.0(s,2H), 6.2(s,1H), 5.6(brs,1H), 3.7(m,1H), 3.66(m,1H), 3.54(m,1H), 2.07(s,3H), 2.068(s,3H), 2.06(s,3H), 1.7(m,1 H), 1.6(m,1H), 0.99(t,3H) ppm.

EXAMPLE 114

2-(4-Chloro-2,6-dimethyl-phenoxy)-4-(S)-(1-hydroxymethyl-propylamino)-6-methyl-nicotinic acid hydrazide 1H NMR(CDCl$_3$) d 9.15(s,1H), 7.04(s,2H), 6.23(s,1H), 3.6–3.8(m,2H), 3.53(m,1H), 2.08(s,6H), 2.05(s,3H), 2.04(s, 3H), 1.5–1.8(m,2H), 1.01(t,3H) ppm.

EXAMPLE 115

2-(4-Chloro-2,6-dimethyl-phenoxy)-N-ethyl-4-(S)-(1-hydroxymethyl-propylamino)-6-methyl-nicotinamide 1H NMR(CDCl$_3$) d 9.74(d,1H), 8.12(s,1H), 7.05(s,2H), 6.23(s,1H), 3.5–3.8(m,3H), 3.43(m,2H), 2.06(s,9H), 1.8(brs, 1H), 1.5–1.7(m,2H), 1.19(t,3H), 1.00(t,3H) ppm.

EXAMPLE 116

2-(4-Chloro-2,6-dimethyl-phenoxy)-4-(S)-(1-hydroxymethyl-propylamino)-6,N-dimethyl-nicotinamide 1H NMR(CDCl$_3$) d 9.80(d,1H), 8.12(s,1H), 7.04(s,2H), 6.22(s,1H), 3.5–3.8(m,3H), 2.93(d,3H), 2.06(s,9H), 1.8(brs, 1H), 1.5–1.7(m,2H), 0.99(t,3H) ppm.

EXAMPLE 117

2-(4-Chloro-2,6-dimethyl-phenoxy)-N-cyclopentyl4-(S)-(1-hydroxymethyl-propylamino)-6-methyl-nicotinamide 1H NMR(CDCl$_3$) d 9.69(d,1H), 8.13(d,1H), 7.04(s,2H), 6.22(s,1H), 4.35(m,1H), 3.4–3.8(m,3H), 2.056(s,9H), 1.4–2.0(m, 10H), 0.99(t,3H) ppm.

EXAMPLE 118

2-(4-Chloro-2,6-dimethyl-phenoxy)-N-cyclopropylmethyl-4-(S)-(1-hydroxymethyl-propylamino)-6-methyl-nicotinamide 1H NMR(CDCl$_3$) d 9.71(d,1H), 8.24(s,1H), 7.05(s,2H), 6.23(s,1H), 3.5–3.8(m,3H), 3.27(t,2H), 2.08(s,6H), 2.07(s, 3H), 1.8(brs,1H), 1.5–1.75(m,2H), 0.99(t,3H), 0.46(m,2H), 0.21(m,2H) ppm.

The title compounds of the following Examples 232 through 236 were prepared by a method analogous to that described for Example 224.

EXAMPLE 119

4-(1-Ethyl-propylamino)-6-methyl-2-(2,4,6-trimethyl-phenylamino)-nicotinamide

A brown solid, mp. 204–206° C.

EXAMPLE 120

4-(1-Ethyl-propoxy)-2-methyl-6-(2,4,6-trimethyl-phenylamino)-pyrimidine-5-carboxylic acid amide Mp. 174–176° C.; Anal. For C$_{20}$H$_{28}$N$_4$O$_2$ calc.: C, 67.39; H, 7.92; N, 15.72; found: C, 67.90; H, 8.19; N, 14.66. 1H NMR(CDCl$_3$) d 7.95(s,1H), 6.89(s,2H), 5.58(s,1H), 5.4(m, 1H), 2.28(s,3H), 2.25(s,3H), 2.15(s,6H), 1.75(m,4H), 0.96 (t,6H) ppm.

EXAMPLE 121

4-(1-Ethyl-propylamino)-6-methyl-2-(2,4,6-trimethyl-phenoxy)-nicotinonitrile

1H NMR(CDCl$_3$) d 6.85(s,2H), 6.06(s,1H), 4.72(d,1H), 3.36(m,1H), 2.28(s,3H), 2.17(s,3H), 2.09(s,6H), 1.5–1.8(m, 4H), 0.96(t,6H) ppm.

EXAMPLE 122

[4-(1-Ethyl-propoxy)-6-methyl-3-nitro-pyridin-2-yl]-(2,4,6-trimethyl-phenyl)-amine The title compound was prepared by heating 2-bromo (or chloro)-4-(1-ethyl-propoxy)-6-methyl-3-nitro-pyridine with 2,4,6-trimethylaniline in DMSO at 130° C. The reaction mixture was quenched with water and extracted with ethyl acetate. The organic layer was separated, dried and concentrated to give crude material. The material was purified through silica gel column chromatography to give the title compound as a yellow solid. 1H NMR(CDCl$_3$) d 8.52(s,1H), 6.92(s,2H), 6.12(s,1H), 4.31(m,1H), 2.32(s,3H), 2.24(s,3H), 2.18(s,6H), 1.77(m,4H0, 1.01(t,6H) ppm.

EXAMPLE 123

4-(1-Ethyl-propoxy)-6-methyl-N2-(2,4,6-trimethyl-phenyl)-pyridine-2,3-diamine

The title compound was prepared by hydrogenation of the corresponding 3-nitro derivative with 10% Pd/C in ethanol at 50 psi. A pale gray solid was obtained in 97% yield, mp. 73–75° C. 1H NMR(CDCl$_3$) d 6.89(s,2H), 6.18(s,1H), 4.22 (m,1H), 3.2(brs,2H), 2.29(s,3H), 2.19(s,6H), 1.7(m,4H), 0.97(t,6H) ppm.

EXAMPLE 124

2-Chloro-N-[4-(1-ethyl-propoxy)-6-methyl-2-(2,4,6-trimethyl-phenylamino)-pyridin-3-yl]-acetamide The title compound was prepared by acylation of 4-(1-ethyl-propoxy)-6-methyl-N2-(2,4,6-trimethyl-phenyl)-pyridine-2,3-diamine with chloroacetyl chloride, NEt$_3$ in THF at room temperature. A tan solid was isolated, mp. 79–82° C. Anal. For C$_{22}$H$_{30}$ClN$_3$O$_2$ calc. C, 65.41; H, 7.49; N, 10.40; found: C, 65.56; H, 7.62; N, 10.98.

EXAMPLE 125

N-Butyl-N-ethyl-6-methyl-3-nitro-N-(2,4,6-trimethyl-phenyl)-pyridine-2,4-diamine A mixture of butyl-(2-chloro-6-methyl-3-nitro-pyridin-4-yl)-ethyl-amine (700 mg, 2.58 mmol) and 2,4,6-trimethylaniline in DMSO was heated in 140° C. oil bath for overnight. An additional 0.75 ml of 2,4,6-trimethylaniline was added and the resulting mixture was heated for an additional 48 hours. The mixture was quenched with water, brine and extracted 3 times with ethyl acetate. The organic layer was separated, dried (MgSO$_4$) and concentrated to dryness. After silica gel column chromatography purification, the title compound was obtained as an oil.

EXAMPLE 126

4-(1-Ethyl-propylamino)-6-methyl-2-(2,4,6-trimethyl-phenylamino)-nicotinic acid

The title compound was prepared by heating 2-chloro-4-(1-ethyl-propylamino)-6-methyl-nicotinic acid and trimethylaniline in the presence of potassium carbonate and copper in DMF. The desired product was isolated by silica gel column chromatography using 5% methanol in chloroform as solvent to give a tan solid, mp. 130–135° C.

EXAMPLE 127

4-(1-Ethyl-propylamino)-6-methyl-2-(2,4,6-trimethyl-phenylamino)-nicotinic acid methyl ester A mixture of 2-chloro-4-(1-ethyl-propylamino)-6-methyl-nicotinic acid methyl ester, trimethylaniline, potassium carbonate, copper in DMF was heated at reflux. The mixture was quenched with ammonium chloride and stirred for 20 min, filtered through celite and washed with ethyl acetate. The filtrate was extracted with ethyl acetate. The organic layer was separated, dried and concentrated to dryness. The residue was purified through silica gel column chromatography using 2% methanol in chloroform as eluent to give the title compound as a solid.

1H NMR(CDCl$_3$) d 8.9(s,1H), 8.0(d,1H), 6.91(s,2H), 5.79s,1H), 3.92(s,3H), 3.37(m,1H), 2.30(s,3H), 2.17(s,3H), 2.10(s,6H), 1.5–1.7(m,4H), 0.96(t,6H) ppm.

EXAMPLE 128

N4-(1-Ethyl-propyl)-3,6-dimethyl-N2-(2,4,6-trimethyl-phenyl)-pyridine-2,4-diamine The title compound was prepared by reduction of 4-(1-ethyl-propylamino)-6-methyl-2-(2,4,6-trimethyl-phenylamino)-nicotinic acid with 1M of lithium aluminium hydride in diethyl ether and aluminium trichloride at reflux. 1H NMR(CDCl$_3$)6.9(s,2H), 6.0(s,1H), 5.4(brs,1H), 3.6(d, 1H), 3.3(m,1H), 2.32(s,3H), 2.2(s,3H), 2.15(s,6H), 1.4–1.7 (m,4H), 1.0(t,6H) ppm.

EXAMPLE 129

2-[4-(1-Ethyl-propylamino)-6-methyl-2-(2,4,6-trimethyl-phenylamino)-pyridin-3-ylmethyl]-malonic acid dimethyl ester Mp. 136–138° C.; Anal. For C$_{26}$H$_{37}$N$_3$O$_4$. ¾ H$_2$O calc.: C, 66.57; H, 8.27; N, 8.96; found: C, 66.67; H, 7.95; N, 8.88.

EXAMPLE 130

[2-(4-Bromo-2,6-dimethyl-phenylamino)-4-(1-ethyl-propylamino)-6-methyl-pyridin-3-yl]-methanol The title compound was prepared by reduction of the corresponding nicotinic acid derivative with BH$_3$.DMS in THF at reflux. Standard work-up procedure gave the title compound as a white foam. 1H NMR(CDCl$_3$) 7.15(s,2H), 6.2(brs,1H), 5.92(s,1H), 4.479m,1H), 4.43(s,2H), 3.25(m, 1H), 2.17(s,3H), 2.10(s,6H), 1.58(m,2H), 1.47(m,2H), 0.90 (t,6H) ppm.

EXAMPLE 131

N2-(2,4-Dichloro-phenyl)-N4-(1-ethyl-propyl)-3,6-dimethyl-pyridine-2,4-diamine

The title compound was prepared by a method analogous to that described for Example 33. 1H NMR(CDCl$_3$) d 7.79(dd,1H), 7.30(d,1H), 7.10(dd,1H), 6.53(brs,1H), 6.13(s, 1H), 3.79(d,1H), 3.2–3.4(m,1H), 2.36(s,3H), 1.92(s,3H), 1.4–1.6(m,4H), 0.93(t,6H) ppm.

EXAMPLE 132

[2-(2,4-Dichloro-phenylamino)-4-(1-ethyl-propylamino)-6-methyl-pyridin-3-yl]-methanol The title compound was prepared by reduction of the corresponding nicotinic acid derivative with BH$_3$.DMS in THF at reflux. 1H NMR(CDCl$_3$) d 7.22(d,1H), 7.07(d,1H), 7.00(d,1H), 6.10(s,1H), 5.7(brs,1H), 4.4(s,2H), 3.3 (m,1H), 2.35(s,3H), 2.02(s,3H), 1.4–1.6(m,4H), 0.92&0.91 (two sets of t,6H) ppm.

EXAMPLE 133

2-[6-Methyl-3-nitro-2-(2,4,6-trimethyl-phenylamino)-pyridin-4-ylamino]-butan-1-ol The title compound was prepared by heating 2-[6-methyl-3-nitro-2-chloro-pyridin-4-ylamino]-butan-1-ol with trimethylaniline in DMSO at 130° C. 1H NMR(CDCl$_3$) d 9.3(brs,1H), 6.93(s,3H), 3.7–3.8(m,3H), 2.30(s,3H), 2.12(s, 6H), 1.8(m,1H), 1.65(m,1H), 1.02(t,3H) ppm

EXAMPLE 134

2-[4-(1-Ethyl-propylamino)-2-methyl-6-(2,4,6-trimethyl-phenoxy)-pyrimidin-5-yl]-propionic acid ethyl ester 1H NMR(CDCl$_3$) d 6.85(s,2H), 5.16(d,1H), 4.49(q,1H), 4.0–4.2(m,3H), 2.289s,3H0, 2.20(s,3H), 2.06(s,6H), 1.4–1.7 (m,4H), 1.44(d,3H), 1.21(t,3H), 0.93(t,3H), 0.87(t,3H) ppm.

EXAMPLE 135

[3-Aminomethyl-6-methyl-2-(2,4,6-trimethyl-phenoxy)-pyridin4-yl]-(1-ethyl-propyl)-amine The title compound was prepared by a method analogous to that described for Example 75. mp. 117–119° C.; Anal. For C$_{21}$H$_{31}$N$_3$O. ⅓ H$_2$O calc.: C, 72.58; H, 9.18; N, 12.09; found: C, 72.93; H, 9.28; N, 12.02.

The following title compounds of Examples 136–138 were prepared by reacting [4-(1-ethyl-propylamino)-6-methyl-2-(4-halo-2,6-dimethyl-phenoxy)-pyridin-3-yl]-methanol with thionyl chloride in benzene, concentrated to dryness, followed by reacting with potassium cyanide in DMSO at room temperature.

EXAMPLE 136

[2-(4-Bromo-2,6-dimethyl-phenoxy)-4-(1-ethyl-propylamino)-6-methyl-pyridin-3-yl]-acetonitrile 1H NMR(CDCl$_3$) d 7.2(s,2H), 6.1(S,1H), 3.82(d,1H), 3.7(s,2H), 3.34(m,1H), 2.1(s,3H), 2.03(s,6H), 1.45–1.7(m, 4H), 0.99(t,6H) ppm.

EXAMPLE 137

[2-(4-Chloro-2,6-dimethyl-phenoxy)-4-(1-ethyl-propylamino)-6-methyl-pyridin-3-yl]-acetonitrile hydrogen chloride 1H NMR(CDCl$_3$) d 7.08(s,2H), 6.2(s,1H), 4.92(d,1H), 3.45(m,1H), 2.71(s,3H), 2.549m,2H), 2.14(s,6H), 1.7(m, 2H), 1.40–1.6(m,4H), 0.95(t,6H) ppm.

EXAMPLE 138

[6-(1-Ethyl-propoxy)-2-methyl-pyrimidin-4-yl]-(2,4,6-trimethyl-phenyl)-amine

MP. 149–151° C., Anal. For C$_{20}$H$_{26}$N$_4$O calc.: C, 72.81; H, 8.68; N, 13.41; found: C, 72.70; H, 8.86; N, 13.14.

EXAMPLE 139

2-[2-(4-Chloro-2,6-dimethyl-phenoxy)-6-methyl-pyridin-4-(S)-ylamino]-butan-1-ol

The title compound was prepared by heating the corresponding nicotinic acid derivative at 160–170° C. oil bath.

1H NMR (CDCl$_3$) d 7.05(s,2H), 6.09(s,1H), 5.35(s,1H), 4.43(s,1H), 3.68(m,1H), 3.64(m,1H), 3.29(m,1H), 2.30(s, 3H), 2.09(s,6H), 1.60(m,1H), 1.47(m,1H), 0.89(t,3H) ppm.

EXAMPLE 140

[3-Aminomethyl-2-(4-chloro-2,6-dimethyl-phenoxy)-6-methyl-pyridin-4-(S)-yl](1-chloromethyl-propyl)-amine The title compound was prepared by reacting [2-[2-(4-chloro-2,6-dimethyl-phenoxy)-3-pyridin-4-(S)-ylamino]-butan-1-ol with thionyl chloride in benzene, concentrated to dryness, followed by reacting with NH$_3$(g) at room temperature. After standard workup procedure and silica gel column chromatography, the title compound was obtained. 1H NMR(CDCl$_3$) d 7.00(s,2H), 6.3(brs,1H), 6.07(s,1H), 4.0–4,2(m,2H), 3.9(brs,2H), 3.5–3.8(m,3H), 2.12(s,3H), 2.03(s,6H), 1.6–1.9(m,2H), 1.00(t,3H) ppm The following title compounds of Examples 254 and 255 were prepared by reacting [2-[2-(4-chloro-2,6-dimethyl-phenoxy)-3-pyridin-4-(S)-ylamino]-butan-1-ol with thionyl chloride in benzene, concentrated to dryness, followed by reacting with an appropriate amine in THF at room temperature. After standard workup procedure and silica gel column chromatography, the title compound was obtained.

EXAMPLE 141

2-[2-(4-Chloro-2,6-dimethyl-phenoxy)-6-methyl-3-methylaminomethyl-pyridin-4-(S)-ylamino]-butan-1-ol 1H NMR(CDCl$_3$) d 7.01(s,2H), 6.14(s,1H), 4.55(brs,1H), 3.6–3.8(m,2H), 3.4(m,1H), 2.6(s,3H), 2.11(s,3H), 2.02(brs, 6H), 1.65(m,2H), 0.97(t,3H)ppm.

EXAMPLE 142

2-[3-Aminomethyl-2-(4-chloro-2,6-dimethyl-phenoxy)-6-methyl-pyridin-4-(S)-ylamino]-butan-1-ol 1H NMR(CDCl$_3$) d 6.999s,2H), 6.10(s,1H), 4.4.00(Abq, 2H), 3.5–3.75(m,2H), 3.4(m,1H), 2.73(brs,4H), 2.08(s,3H), 2.00(s,6H), 1.58(m,4H), 0.94(t,3H) ppm.

The title compounds of the following Examples 143 through 149 were prepared by bromination or chlorination of 2-[2-(substituted-phenoxy)-6-methyl-pyridin-4-alkylamine with NBS or NCS in methylene chloride or chloroform at room temperature.

EXAMPLE 143

[3-Bromo-6-methyl-2-(2,4,6-trimethyl-phenoxy)-pyridin-4-yl]-(1-ethyl-propyl)-amine 1H NMR(CDCl$_3$) d 6.85(s,2H), 6.04(s,1H), 4.62(d,1H), 3.33(m,1H), 2.27(s,3H), 2.13(s,3H), 2.08(s,6H), 1.5–1.7(m, 2H), 0.95(t,3H) ppm.

EXAMPLE 144

2-[3,5-Dibromo-2-(4-chloro-2,6-dimethyl-phenoxy)-6-methyl-pyridin-4-ylamino]-butan-1-ol 1H NMR(CDCl$_3$) d 7.02(s,2H), 4.34(m,1H), 3.6–3.8(m, 2H), 2.30(s,3H), 2.05(s,6H), 1.5–1.8(m,2H), 0.98(t,3H) ppm.

EXAMPLE 145

2-[3-Bromo-6-(4-chloro-2,6-dimethyl-phenoxy)-2-methyl-pyridin-4-(S)-ylamino]-butan-1-ol 1H NMR(CDCl$_3$) d 7.05(s,2H), 5.62(s,1H), 4.86(d,1H), 3.55–3.7(m,2H), 3.3(m,1H), 2.428(s,3H), 2.09(s,6H), 1.4–1.7(m,3H), 0.91(t,3H) ppm.

EXAMPLE 146

2-[3-Bromo-2-(4-chloro-2,6-dimethyl-phenoxy)-6-methyl-pyridin-4-(S)-ylamino]-butan-1-ol 1H NMR(CDCl$_3$) d 7.02(s,2H), 6.14(s,1H), 4.81(d,1H), 3.6–3.8(m,2H), 3.45(m,1H), 2.12(s,3H), 2.08(s,6H), 1.5–1.8 (m,2H), 1.00(t,3H) ppm.

EXAMPLE 147

2-[3-Chloro-2-(4-chloro-2,6-dimethyl-phenoxy)-6-methyl-pyridin-4-(S)-ylamino]-butan-1-ol 1H NMR(CDCl$_3$) d 7.02(s,2H), 6.18(s,1H), 4.76(d,1H), 3.6–3.8(m,2H), 3.45(m,1H), 2.13(s,3H), 2.07(s,6H), 1.5–1.8 (m,2H), 0.99(t,3H) ppm.

EXAMPLE 148

2-[3,5-Dichloro-2-(4-chloro-2,6-dimethyl-phenoxy)-6-methyl-pyridin-4-ylamino]-butan-1-ol 1H NMR(CDCl$_3$) d 7.03(s,2H), 4.34(m,1H), 3.6–3.8(m, 2H), 2.40(s,3H), 2.05(s,6H), 1.5–1.8(m,2H), 0.99(t,3H) ppm.

EXAMPLE 149

2-[3-Chloro-6-(4-chloro-2,6-dimethyl-phenoxy)-2-methyl-pyridin-4-(S)-ylamino]-butan-1-ol 1H NMR(CDCl$_3$) d 7.05(s,2H), 5.66(s,1H), 4.86(brs,1H), 3.5–3.8(m,2H), 3.3(m,1H), 2.38(s,3H), 2.09(s,6H), 1.4–1.7 (m,3H), 0.91(t,3H) ppm.

EXAMPLE 150

2-(4-Chloro-2,6-dimethyl-phenoxy)-4-(S)-(4-ethyl-2-oxo-oxazolidin-3-yl)-6-methyl-nicotinonitrile The title compound was prepared by reacting with 2-(4-chloro-2,6-dimethyl-phenoxy)-4-(1-hydroxymethyl-propylamino)-6-methyl-nicotinic acid with triphosgene/NEt$_3$ in THF. 1H NMR(CDCl$_3$) d 7.18(s,1H), 7.06(s,2H), 5.00(m,1H), 4.64(t,1H), 4.23(dd,1H), 2.339s,3H), 2.08(s, 6H), 1.5–1.8(m,2H), 0.949t,3H) ppm.

EXAMPLE 151

2-(2,4-Dimethoxy-phenylamino)-4-(1-methoxymethyl-propoxy)-6-methyl-nicotinic acid 1H NMR(CDCl$_3$) d 8.3(brs,1H), 6.5(m,3H), 6.26(s,1H), 4.66(m,1H), 3.92(s,3H), 3.85(s,3H), 3.66(m,2H), 3.43(s, 3H), 2.52(s,3H), 1.91(m,2H), 1.07(t,3H) ppm.

EXAMPLE 152

4-(1-Ethyl-propoxy)-2-methyl-6-(2,4,6-trimethyl-phenylamino)-pyrimidine-5-carbonitrile 1H NMR(CDCl$_3$) d 6.92(s,2H), 6.45(s,1H), 5.22(m,1H), 2.29(s,6H), 2.16(s,6H), 1.70(m,4H), 0.93(t,6H) ppm.

EXAMPLE 153

N-(1-Ethyl-propyl)-2,5-dimethyl-N'-(2,4,6-trimethyl-phenyl)-pyrimidine-4,6-diamine 1H NMR(CDCl$_3$) d 8.9(s,1H), 6.85(s,2H), 4.95(d,1H), 4.21(m,1H), 2.5(s,3H), 2.25(s,3H), 2.13(s,6H), 1.4–1.7(m, 4H), 1.3(s,3H), 0.85(t,6H) ppm

EXAMPLE 154

5-Chloro-N4-(1-ethyl-propyl)-2-methyl-N6-(2,4,6-trimethyl-phenyl)-pyrimidine-4,6-diamine 1H NMR(CDCl$_3$) d 6.85(s,2H), 6.0(s,1H), 4.D(m,1H), 4.2(m,1H), 2.3(s,3H), 2.22(,3H), 2.17(s,6H), 1.4–1.70(m, 4H), 0.97(t,6H) ppm.

EXAMPLE 155

5-Bromo-N-(1-ethyl-propyl)-2-methyl-N'-(2,4,6-trimethyl-phenyl)-pyrimidine-4,6-diamine MP. 117–119° C., Anal. For C$_{19}$H$_{21}$BrN$_4$ calc.: C, 58.31; H, 6.95; N, 14.32; found: C, 58.43; H, 7.08; N, 14.23.

EXAMPLE 156

4-(1-Ethyl-propylamino)-2-methyl-6-(2,4,6-trimethyl-phenylamino)-pyrimidine-5-carboxylic acid 1H NMR(CDCl$_3$) d 12.2(brs,1H), 11.1(brs,1H), 6.84(s, 2H), 4.18(m,1H), 2.38(s,3H), 2.18(s,3H), 2.15(s,6H), 1.56 (m,4H), 0.90(t,6H) ppm.

EXAMPLE 157

[4-(Cyclopropylmethyl-propyl-amino)-2-methyl-6-(2,4,6-trichloro-phenylamino)-pyrimidin-5-yl]-methanol 1H NMR(CDCl$_3$) d 7.49s,2H), 4.95(s,2H), 4.92(s,1H), 3.28(brs,4H), 2.359s,3H), 1.54(m,2H), 0.95(m,1H), 0.81(t, 3H), 0.44(m,2H), 0.19(m,2H) ppm.

EXAMPLE 158

6-(1-Ethyl-propoxy)-2,N5,N5-trimethyl-N4-(2,4,6-trimethyl-phenyl)-pyrimidine-4,5-diamine The title compound was prepared by methylation of 6-(1-ethyl-propoxy)-2-methyl-N4-(2,4,6-trimethyl-phenyl)-pyrimidine-4,5-diamine with lithium bis(trimethylsilyl) amide in THF, followed by quenching with methyl iodide. 1H NMR(CDCl$_3$) d 7.35(s,1H), 6.90(s,2H), 5.16(m,1H), 2.73(s,6H), 2.29(s,3H), 2.27(s,3H), 2.18(s,6H), 1.6–1.8(m, 4H), 0.96(t,6H) ppm.

EXAMPLE 159

[5-Bromo-6-(1-ethyl-propoxy)-2-methyl-pyrimidin-4-yl]-(2,4,6-trimethyl-phenyl)-amine The title compound was prepared by reacting [5-bromo-6-(1-ethyl-propoxy)-2-methyl-pyrimidin-4-yl]-(2,4,6-trimethyl-phenyl)-amine with 3-pentanol/NaH in THF at reflux overnight. After standard work-up and purification, the title compound was obtained as a white solid, mp. 94–96° C. 1H NMR(CDCl$_3$) d 6.91(s,2H), 6.41(s,1H), 5.13 (m,1H), 2.29(s,3H), 2.26(,3H), 2.17(s,6H), 1.70(m,4H), 0.95(t,6H) ppm.

EXAMPLE 160

4-(1-Ethyl-propoxy)-2-methyl-6-(2,4,6-trimethyl-phenylamino)-pyrimidine-5-carboxylic acid To a solution of n-BuLi in THF was added a solution of [5-bromo-6-(1-ethyl-propoxy)-2-methyl-pyrimidin-4-yl]-(2,4,6-trimethyl-phenyl)-amine in THF at −78° C. After stirring for 10 minutes, CO$_2$(g) was added at −78° C. and stirred at that temperature for 1 hour, then gradually warmed to room temperature. The resulting mixture was quenched with water and adjusted to pH 2 to 3 and extracted with chloroform. The organic layer was separated, dried and concentrated to dryness. The residue was purified through silica gel column chromatography to give the title compound as a solid, mp. 118–120° C., Anal. For C$_{20}$H$_{27}$N$_3$O$_3$ calc.: C, 67.20; H, 7.61; N, 11.76; found: C, 67.25; H, 7.87; N, 11.48.

EXAMPLE 161

[4-(1-Ethyl-propoxy)-2-methyl-6-(2,4,6-trimethyl-phenylamino)-pyrimidin-5-yl]-methanol To a solution of 4-(1-ethyl-propoxy)-2-methyl-6-(2,4,6-trimethyl-phenylamino)-pyrimidine-5-carboxylic acid in dry THF was added BH$_3$.DMS. The resulting mixture was heated at reflux. The mixture was quenched with dilute HCl and stirred for 30 minutes;, adjusted pH to 7.5–8.5, then extracted with ethyl acetate. The organic layer was separated, dried and concentrated to give a crude material. The crude material was purified through silica gel column chromatography to give the title compound as a solid, mp. 121–123° C., Anal. For C$_{20}$H$_{29}$N$_3$O$_2$ calc. C, 69.94; H, 8.51; N, 12.23; found: C, 69.73; H, 8.47; N, 11.99.

EXAMPLE 162

[6-(1-Ethyl-propoxy)-5-methoxymethyl-2-methyl-pyrimidin-4-yl]-(2,4,6-trimethl-phenyl)-amine The title compound was prepared by reacting [4-(1-ethyl-propoxy)-2-methyl-6-(2,4,6-trimethyl-phenylamino)-pyrimidin-5-yl]-methanol with NaH, followed by quenching with MeI. 1H NMR(CDCl$_3$) d 7.0(s,1H), 6.89(s,2H), 5.12 (m,1H), 4.62(s,2H), 3.33(s,3H), 2.28(s,3H0, 2.27(s,3H), 2.14(s,6H), 1.66(m,4H), 0.91(t,6H) ppm.

EXAMPLE 163

[5-Aminomethyl-6-(1-ethyl-propoxy)-2-methyl-pyrimidin-4-yl]-(2,4,6-trimethyl-phenyl)-amine To a solution of [4-(1-ethyl-propoxy)-2-methyl-6-(2,4,6-trimethyl-phenylamino)-pyrimidin-5-yl]-methanol in anhydrous methylene chloride was added thionyl chloride. After stirring for 1 hour, the reaction mixture was concentrated to dryness. The residue was dissolved in dry THF and NH$_3$(g) was bubbled in. The reaction mixture was quenched with water and extracted with ethyl acetate. The reaction was worked-up and purified by standard procedure to give the title compound.

1H NMR(CDCl$_3$) d 8.50(s,1H), 6.88(s,2H), 5.08(m,1H), 3.97(s,2H), 2.279s,3H), 2.25(s,3H), 2.159s,6H), 1.74(brs, 2H), 1.65(m,4H), 0.91(t,6H) ppm.

EXAMPLE 164

7-(1-Ethyl-propoxy)-5-methyl-3-(2,4,6-trimethyl-phenyl)-3H-imidazo[4,5-b]pyridin-2-ylamine The title compound was prepared by reacting 4-(1-ethyl-propoxy)-6-methyl-N2-(2,4,6-trimethyl-phenyl)-pyridine-2,3-diamine with BrCN in acetonitrile at room temperature overnight. The mixture was quenched with water and adjusted to pH 8.0 with saturated sodium bicarbonate and extracted with ethyl acetate. The organic layer was separated, dried and concentrated to give crude material. The material was purified through silica gel column chromatography to give the title compound as a white solid, mp. 159–161° C. 1H NMR(CDCl$_3$) d 7.05(s,2H), 6.5(s,1H), 4.6(m,1H), 4.3(m,2H), 2.45(s,3H), 2.35(s,3H), 2.0(s,6H), 1.7(m,4H), 1.0(t,6H) ppm.

EXAMPLE 165

7-(1-Ethyl-propoxy)-5-methyl-3-(2,4,6-trimethyl-phenyl)-3H-imidazo[4,5-b]pyridine A mixture of 4-(1-ethyl-propoxy)-6-methyl-N2-(2,4,6-trimethyl-phenyl)-pyridine-2,3-diamine, trimethyl orthoformate, p-toluenesulfonic acid monohydrate in toluene was heated at reflux using Dean-Stark apparatus for 24 hours. The mixture was heated at reflux overnight. The mixture was quenched with water, sat. NaHCO$_3$, extracted with ethyl acetate. The organic layer was separated, dried (MgSO$_4$) and concentrated to dryness. After purification, the title compound was isolated. Anal. For C$_{21}$H$_{29}$N$_3$O.¼H$_2$O calc. C, 73.76; H, 8.10; N, 12.29; found: C, 73.22; H, 7.96; N, 12.42.

EXAMPLE 166

7-(1-Ethyl-propoxy)-5-methyl-3-(2,4,6-trimethyl-phenyl)-1,3-dihydro-imidazo[4,5-b]pyridin-2-one The title compound was prepared by reacting 4-(1-ethyl-propoxy)-6-methyl-N2-(2,4,6-trimethyl-phenyl)-pyridine-2,3-diamine with triphosgene, NEt$_3$ in THF at room temperature. A white solid was isolated, mp. 184–186° C. Anal. For C$_{21}$H$_{27}$N$_3$O$_2$ calc. C, 71.36; H, 7.70; N, 11.89; found: C, 71.09; H, 7.75; N, 11.63.

EXAMPLE 167

7-(1-Ethyl-propoxy)-1,5-dimethyl-3-(2,4,6-trimethyl-phenyl)-1,3-dihydro-imidazo[4,5-b]pyridin-2-one The title compound was prepared by reacting 7-(1-ethyl-propoxy)-5-methyl-3-(2,4,6-trimethyl-phenyl)-1,3-dihydro-imidazo[4,5-b]pyridin-2-one with lithium bis(trimethylsilyl)amide, followed by quenching with methyl iodide. Mp. 151–153° C. Anal. For C$_{22}$H$_{29}$N$_3$O$_2$. ¼H$_2$O calc. C, 71.03; H, 7.99; N, 11.30; found: C, 71.29; H, 8.01; N, 11.03.

EXAMPLE 168

(1-Ethyl-propyl)-[5-methyl-3-(2,4,6-trimethyl-phenyl)-3H-imidazo[4,5-b]pyridin-7-yl]-amine A mixture of N-4-(1-ethyl-propyl)-6-methyl-N-2-(2,4,6-trimethyl-phenyl)-pyridine-2,3,4-triamine (250 mg, 0.77 mmol), trimethyl orthoformate (0.081 g, 0.766 mmol), p-toluenesulfonic acid monohydrate (0.01 g) in benzene was heated at reflux using Dean-Stark apparatus for 24 hours. Benzene was removed and toluene was added and an excess of trimethyl orthoformate (0.084 ml) was added to the reaction mixture. The mixture was heated at reflux overnight. The mixture was quenched with water, sat. NaHCO$_3$, extracted with ethyl acetate. The organic layer was separated, dried (MgSO$_4$) and concentrated to dryness. After purification, the title compound was isolated as white crystals, mp 78–80° C.

EXAMPLE 169

[2,5-Dimethyl-3-(2,4,6-trimethyl-phenyl)-3H-imidazo[4,5-b]pyridin-7-yl]-1-ethyl-propyl)-amine A mixture of N-4-(1-ethyl-propyl)-6-methyl-N-2-(2,4,6-trimethyl-phenyl)-pyridine-2,3,4-triamine (250 mg, 0.77 mmol), trimethyl orthoacetate (0.184 g, 1.532 mmol), p-toluenesulfonic acid monohydrate (0.01 g) in toluene was heated at reflux using Dean-Stark apparatus for 3 hours. The mixture was quenched with water, brine, extracted with ethyl acetate. The organic layer was separated, dried (MgSO$_4$) and concentrated to dryness. After purification, the title compound was obtained as a white crystal, mp 101–103° C. Anal. For C$_{22}$H$_{30}$N$_4$ calc. C, 75.39; H, 8.63; N, 15.98; found, C, 75.44; H, 8.95; N, 15.95.

EXAMPLE 170

N7-(1-Ethyl-propyl)-5-methyl-3-(2,4,6-trimethyl-phenyl)-3H-imidazo[4,5-b]pyridine-2,7-diamine The title compound was prepared by reacting N4-(1-ethyl-propyl)-6-methyl-N2-(2,4,6-trimethyl-phenyl)-pyridine-2,3,4-triamine with BrCN in acetonitrile at room temperature overnight. The mixture was quenched with water and adjusted to pH 8.0 with saturated sodium bicarbonate and extracted with ethyl acetate. The organic layer was separated, dried and concentrated to give crude material. The material was purified through silica gel column chromatography to give the title compound as a brown solid, mp. 158–160° C.; Anal. For C$_{21}$H$_{29}$N$_5$ ¼H$_2$O calc. C, 70.85; H, 8.35; N, 19.67; found: C, 71.07; H, 8.30; N, 19.63.

EXAMPLE 171

6-(1-Ethyl-propylamino)-2,7-dimethyl-9-(2,4,6-trimethyl-phenyl)-7,9-dihydro-purin-8-one The title compound was prepared by methylation of 6-(1-ethyl-propylamino)-2-methyl-9-(2,4,6-trimethyl-phenyl)-7,9-dihydro-purin-8-one with lithium bis(trimethylsilyl)amide in THF, followed by quenching with methyl iodide. 1H NMR(CDCl$_3$) d 6.98(s,2H), 4.45(d,1H), 4.3(m,1H), 3.7(s,3H), 2.4(s,3H), 2.3(s,3H), 2.1(s,6H), 1.5–1.8(m,4H), 1.0(t,6H) ppm.

EXAMPLE 172

6-(1-Ethyl-propoxy)-2,7-dimethyl-9-(2,4,6-trimethyl-phenyl)-7,9-dihydro-purin-8-one The title compound was prepared by methylation of 6-(1-Ethyl-propoxy)-2-methyl-9-(2,4,6-trimethyl-phenyl)-7,9-dihydro-purin-8-one with lithium bis(trimethylsilyl)amide in THF, followed by quenching with methyl iodide. 1H NMR(CDCl$_3$) d7.00(s,2H), 5.31(m,1H), 3.66(s,3H), 2.479s,3H), 2.33(s,3H), 2.06(s,6H), 1.79(m,4H), 1.01(t,6H) ppm.

EXAMPLE 173

[2-(4-Methoxy-2,6-dimethyl-phenoxy)-6-methyl-3-nitro-pyridin-4-yl]-(1-methoxymethyl-propyl)-amine 1H NMR(CDCl$_3$) d 7.71(d,1H), 6.57(s,2H), 6.21(s,1H), 3.76(s,3H), 3.59(m,1H), 3.48(m,1H), 3.45(m,1H), 3.37(s,3H), 2.13(s,3H), 2.08(s,6H), 1.6–1.8(m,4H), 0.86(t,3H) ppm.

EXAMPLE 174

(1-Ethyl-propyl)-[2-(4-methoxy-2,6-dimethyl-phenoxy)-3,6-dimethyl-pyridin4-yl]-amine 1H NMR(CDCl$_3$) d 6.64(s,2H), 6.12(s,1H), 3.82(s,3H), 3.36(m,1H), 2.26(s,3H), 2.13(s,6H), 2.10(s,3H), 1.5–1.8m, 4H), 0.99(t,6H).

EXAMPLE 175

2-[2-(4-Methoxy-2,6-dimethyl-phenoxy)-3,6-dimethyl-pyridin-4-ylamino]-butan-1-ol 1H NMR(CDCl₃) d 6.64(s,2H), 6.13(s,1H), 4.10(m,1H), 3.76(s,3H), 3.7–3.8(m,21H, 3.57(m,1H), 2.21(s,3H), 2.19(s,6H), 2.12(s,3H), 1.6–1.8(m,2H), 1.04(t,3H) ppm.

EXAMPLE 176 sec-Butyl-[3-methoxy-2-(4-methoxy-2,6-dimethyl-phenoxy)-6-methyl-pyridin4-yl]-amine 1H NMR(CDCl₃) d 6.64(s,2H), 6.13(s,1H), 4.51(d,1H), 3.92(s,3H), 3.82(s,3H), 3.469m, 1H), 2.18(s,3H), 2.15(s,6H), 1.60(m,2H), 1.26(d,3H), 1.00(t,3H) ppm.

EXAMPLE 177

2-(4-Chloro-2,6-dimethyl-phenoxy)-4-(4-ethyl-oxazolidin-3-yl)-3,6-dimethyl-pyridine 1H NMR(CDCl₃) d 7.07(s,2H), 6.36(s,1H), 4.98(m,1H), 4.78(m,1H), 4.23(m,1H), 3.83(m,1H), 3.71(m,1H), 2.28(s,3H), 2.20(s,3H), 2.09(s,6H), 1.81(m,1H), 1.58(m,1lH), 0.98(t,3H) ppm.

EXAMPLE 178

4-(4-Ethyl-oxazolidin-3-yl)-2-(4-methoxy-2,6-dimethyl-phenoxy)-3,6-dimethyl-pyridine 1H NMR(CDCl₃) d 6.65(s,2H), 6.36(s,1H), 4.98(m,1H), 4.77(m,1H), 4.23(m,1H), 3.83(s,3H), 3.71(m,1H),), 2.29(s,3H), 2.22(s,3H), 2.119(s,6H), 1.82(m,1H), 1.56(m,1H), 0.99(t,3H) ppm

EXAMPLE 179

2-(4-Methoxy-2,6-dimethyl-phenoxy)-N %4&-(1-methoxymethyl-propyl)-6-methyl-pyridine-3,4-diamine 1H NMR(CDCl₃) d 6.64(s,2H), 6.16(s,1H), 4.3(m,1H), 3.82(s,3H), 3.6–3.8(m,2H), 3.42(s,3H), 3.2(brs,2H), 2.18(s,3H), 2.13(s,6H), 1.6–1.8(m,2H), 1.03(t,3H) ppm.

EXAMPLE 180

3-[2-(4-Chloro-2,6-dimethyl-phenoxy)-3-hydroxymethyl-6-methyl-pyridin4-ylamino]-pentan-2-ol 1H NMR(CDCl₃) d 7.01(s,2H), 6.16(s,1H), 5.19(d,1H), 4.94(m,2H), 3.88(m,1H), 3.27(m,1H), 2.11(s,3H), 2.05(s,6H), 1.73(m,1H), 1.57(m,1H), 1.24(d,3H), 0.97(t,3H)ppm.

EXAMPLE 181

2-(4-Chloro-2,6-dimethyl-phenoxy)-4-(1-ethyl-2-oxo-propylamino)-6-methyl-nicotinic acid methyl ester 1H NMR(CDCl₃) d 8.63(d,1H), 7.01(s,2H), 5.90(s,1H), 3.95(m,1H), 3.90(s,3H), 2.08(s,3H), 2.05(s,3H), 2.03(s,6H), 1.8–2.0(m,2H), 1.00(t,3H) ppm.

EXAMPLE 182

3-[2-(4-Chloro-2,6-dimethyl-phenoxy)-3-methoxymethyl-6-methyl-pyridin-4-ylamino]-pentan-2-ol 1H NMR(CDCl₃) d 7.08(s,2H), 6.21(s,1H), 5.40(brs,1H), 4.83(q,2H), 3.91(m,1H), 3.40(s,3H), 3.33(m,1H), 2.20(s,3H), 2.10(s,6H), 1.78(m,1H), 1.58(m,1H), 1.29(d,3H), 1.01(t,3H) ppm.

EXAMPLE 183

3-[2-(4-Methoxy-2,6-dimethyl-phenoxy)-3,6-dimethyl-pyridin-4-ylamino]-pentan-2-ol 1H NMR(CDCl₃) d 6.66(s,2H), 6.27(s,1H), 4.05(m, 1H), 3.82(s,3H), 3.38(m, 1H), 2.35(s,3H), 2.21(s,3H), 2.14(s,6H), 1.6–1.9(m,2H), 1.30(m,3H), 1.01(t,3H)ppm.

EXAMPLE 184

4-sec-Butylamino-2-(4-methoxy-2,6-dimethyl-phenoxy)-6-methyl-nicotinic acid methyl ester 1H NMR(CDCl₃) d 8.01(d,1H), 6.58(s,2H), 6.06(s,1H), 3.85(s,3H), 3.77(s,3H), 2.10(s,3H), 2.07(s,6H), 1.21(d,3H0, 0.97(t,3H) ppm.

EXAMPLE 185

2-(4-Chloro-2,6-dimethyl-phenoxy)-4-(1-ethyl-2-hydroxy-2-methyl-propylamino)-6-methyl-nicotinic acid methyl ester 1H NMR(CDCl₃) d 8.28(d,1H), 7.06(s,2H), 6.32(s,1H), 3.92(s,3H), 3.41(m,1H), 2.14(s,3H), 2.12(s,6H), 1.91(m,1H), 1.44(m,1H), 1.33(s,3H), 1.30(s,3H0, 0.99(s,3H) ppm.

EXAMPLE 186

4-(1-Hydroxymethyl-propylamino)-2-(4-methoxy-2,6-dimethyl-phenoxy)-6-methyl-nicotinic acid methyl ester 1H NMR(CDCl₃) d 8.13(d,1H), 6.63(s,2H), 6.21(s,1H), 3.91(s,3H0, 3.82(s,3H0, 3.81(m,2H), 3.59(m,1H), 2.16(s,3H), 2.12(s,6H), 1.6–1.859m,2H), 1.05(t,3H) ppm.

EXAMPLE 187

2-(4-Chloro-2,6-dimethyl-phenoxy)-4-(1-hydroxymethyl-3-methylsulfanyl-propylamino)-6-methyl-nicotinic acid methyl ester A mixture of 2-(4-chloro-2,6-dimethyl-phenoxy)-4-chloro-6-methyl-nicotinic acid methyl ester and L-methioninol in N-methyl-2-pyrodone (NMP) was heated in a 134° C. oil bath for 3 hr. Standard work-up procedure and purification provided the title compound. 1H NMR (CDCl₃) d 8.25(d,1H), 7.02(s,2H), 6.30(s,1H), 3.85(s,3H), 3.6–3.9(m,3H), 2.5–2.7(m,2H), 2.14(s,3H), 2.10(s,3H), 2.06(s,6H), 1.8–2.1 (m,2H)ppm.

EXAMPLE 188

2-(4-Chloro-2,6-dimethyl-phenoxy)-6-methyl-4-(S)-(tetrahydro-furan-3-ylamino-nicotinic acid methyl ester To a solution of {3-[2-(4-chloro-2,6-dimethyl-phenoxy)-3-methoxycarbonyl-6-methyl-pyridin-4-ylamino]-4-hydroxy-butyl}-dimethyl-sulfonium iodide in dry THF was added t-BuOK at –10° C. The mixture was stirred at –10° C. until all starting material was consumed. Standard work-up procedure and silica gel purification gave the title compound.

1H NMR(CDCl₃) d 8.25(d,1H), 7.01(s,2H), 6.05(s,1H), 4.11(m,1H), 3.9–4.1(m,2H), 3.8–3.9(m,1H), 3.86(s,3H), 3.73(m,1H), 2.2–2.4(m,1H), 2.11(s,3H), 2.05(s,6H), 1.95 (m,1H) ppm.

EXAMPLE 189

{3-[2-(4-Chloro-2,6-dimethyl-phenoxy)-3-methoxycarbonyl-6-methyl-pyridin-4-ylamino]-4-hydroxy-butyl}-dimethyl-sulfonium iodide A mixture of 2-(4-chloro-2,6-dimethyl-phenoxy)-4-(1-hydroxymethyl-3-methylsulfanyl-propylamino)-6-methylnicotinic acid methyl ester and MeI in EtOAc was heated at reflux in a sealed tube. The mixture was concentrated to dryness and triturated with diethyl ether to give the title compound. 1H NMR(CD$_3$OD) d 7.11(s,2H), 6.61(s,1H), 4.00(m,1H), 3.86(s,3H), 3.6–3.9(m,3H), 2.95(d,6H), 2.5–2.7(m,2H), 2.22(s,3H), 2.07(s,6H), 1.8–2.1(m,2H)ppm.

EXAMPLE 190

4-(1-Hydroxymethyl-3-methylsulfanyl-propylamino)-2-(4-methoxy-2,6-dimethyl-phenoxy)-6-methyl-nicotinic acid methyl ester 1H NMR(CDCl$_3$) d 8.15(d,1H), 6.58(s,2H), 6.28(s,1H), 3.85(s,3H), 3.76(s,3H), 3.6–3.9(m,3H), 2.5–2.7(m,2H), 2.12(s,3H), 2.09(s,3H), 2.07(s,6H), 1.8–2.1(m,2H)ppm.

EXAMPLE 191

4-(1-Hydroxymethyl-propylamino)-2-(4-methoxy-2,6-dimethyl-phenoxy)-6,N-dimethyl-nicotinamide 1H NMR(CDCl$_3$) d 9.84(d,1H), 8.31(m,1H), 6.66(s,2H), 6.29(s,1H), 3.81(s,3H), 3.5–3.9(m,3H), 2.98(d,3H), 2.15(s, 3H), 2.12(s,6H), 1.6–1.8(m,2H), 1.05(t,3H)ppm.

EXAMPLE 192

4-sec-Butylamino-2-(4-methoxy-2,6-dimethyl-phenoxy)-6,N-dimethyl-nicotinamide

1H NMR(CDCl$_3$) d 9.77(brs,1H), 8.22(brs,1H), 6.61(s, 2H), 6.11(s,1H), 3.78(s,3H), 3.45(m,1H), 2.93(d,3H), 2.10 (s,3H), 2.07(s,6H), 1.5–1.7(m,2H), 1.23(m,3H), 0.98(t,3H) ppm.

EXAMPLE 193

2-(4-Methoxy-2,6-dimethyl-phenoxy)-6-methyl-4-(tetrahydro-furan-3-ylamino)-nicotinic acid methyl ester 1H NMR(CDCl$_3$) d 8.28(d,1H), 6.63(s,2H), 6.09(s,1H), 4.15(m,1H), 3.98–4.1(m,2H), 3.8–3.98(m,1H), 3.90(s,3H), 3.81(s,3H), 3.76(m,1H), 2.32–2.36(m,1H), 2.19(s,3H), 2.11(s,6H), 1.95(m,1H) ppm.

EXAMPLE 194

4-sec-Butylamino-2-(4-methoxy-2,6-dimethyl-phenoxy)-6-methyl-nicotinamide

1H NMR(CDCl$_3$) d 9.74(ds,1H), 8.05(brs,1H), 6.65(s, 2H), 6.16(s,1H), 5.55(brs,1H), 3.83(s,3H), 3.51(m,1H), 2.16 (s,3H), 2.12(s,6H), 1.5–1.7(m,2H), 1.26(d,3H), 1.02(t,3H) ppm.

The following Examples 195–256 relate to other compounds of formula I of the invention, wherein R$_4$ is —COOCH$_3$:

The following title compounds of Examples 195–209 were prepared by the method analogous to that described in Example 13 starting with an a 4-chloro-2-(substituted-phenoxy)-6-methyl-nicotinic acid methyl ester and with an appropriate amine:

EXAMPLE 195

2-(4-Ethoxy-2,6-dimethyl-phenoxy)-4-(1-hydroxymethyl-3-methylsulfanyl-propylamino)-6-methyl-nicotinic acid methyl ester 1H NMR (CDCl$_3$) d 8.35(d, 1H), 6.60(s, 2H), 6.41(s, 1H), 4.03(q, 2H), 3.90(m, 1H), 3.86(s, 3H), 3.75(m, 2H), 2.60(, 2H), 2.21(s, 3H), 2.11(s, 3H), 2.09(s, 6H), 2.03(m, 1H), 1.88(m, 1H), 1.40(t, 1.39)ppm

EXAMPLE 196

4-(1-Hydroxymethyl-3-methylsulfanyl-propylamino)-2-[4-(2-methoxy-ethoxy)-2,6-dimethyl-phenoxy]-6-methyl-nicotinic acid methyl ester 1H NMR(CDCl$_3$) d 8.38(d, 1H), 6.64(s, 2H), 6.42(s, 1H), 4.10(m, 2H), 3.92(m, 1H), 3.86(s, 3H), 3.73(m, 5H), 3.45(s, 3H), 2.60(m, 2H), 2.22(s, 3H), 2.13(s, 3H), 2.09(s, 6H), 1.87(m, 2H)ppm

EXAMPLE 197

2-(2,6-Dimethyl-4-trifluoromethoxy-phenoxy)-4-(1-hydroxymethyl-3-methylsulfanyl-propylamino)-6-methyl-nicotinic acid methyl ester 1H NMR(CDCl$_3$) d 8.21 (br d, 1H, J=8 Hz), 6.91 (s, 2H), 6.28 (s, 1H), 3.87 (s, 3H), 3.84 (m, 1H), 3.70–3.76 (m, 2H), 2.53–2.68 (m, 2H), 2.11 (m, 12H), 1.88–2.06 (m, 2H).

EXAMPLE 198

2-(4-Chloro-2,6-dimethyl-phenoxy)-4-(R)-(1-hydroxymethyl-3-methylsulfanyl-propylamino)-6-methyl-nicotinic acid methyl ester C$_{21}$H$_{27}$ClN$_2$O$_{4s}$: MS: M+1 [439.2]

EXAMPLE 199

2-(4-Chloro-2,6-dimethoxy-phenoxy)-4-(1-hydroxymethyl-propylamino)-6-methyl-nicotinic acid methyl ester 1H NMR(CDCl$_3$) d 8.29 (d, 1H, J+8 Hz), 6.63 (s, 2H), 6.23 (s, 1H), 3.86 (s, 3H), 3.74 (s, 6H), 3.69–3.72 (m, 1H), 3.62–3.66 (m, 1H), 3.52–3.58 (m, 1H), 2.83 (s, 1H), 2.13 (s, 3H), 1.70–1.77 (m, 1H), 1.54–1.61 (m, 1H), 0.99 (t, 3H, J=7 Hz)

13C NMR(CDCl$_3$) d.169.75, 158.50, 153.43, 130.15, 106.96, 101.49, 64.67, 56.95, 56.12, 56.05, 52.18, 46.05, 24.92, 10.67

EXAMPLE 200

2-(4-Chloro-2,6-dimethoxy-phenoxy)-4-(1-hydroxymethyl-3-methylsulfanyl-propylamino)-6-methyl-nicotinic acid methyl ester 1H NMR(CDCl$_3$) d 8.39 (br d, 1H, J=7 Hz), 6.64 (s, 2H), 6.30 (s, 1H), 3.87 (s, 3H), 3.75 (s, 6H), 3.36–3.39 (m, 1H), 2.84 (s, 1H), 2.53–2.70 (m, 2H), 2.35–2.39 (m, 1H), 2.14 (d, 3H, J=9 Hz), 1.94–2.07 (m, 2H), 1.79–1.92 (m, 2H) ppm. APCl+m/z=471.2 (M+1), 473.2 (M+3)

EXAMPLE 201

2-(4-Chloro-2,6-dimethyl-phenoxy)-4-[(1-hydroxymethyl-propyl)-methyl-amino]-6-methyl-nicotinic acid methyl ester

EXAMPLE 202

4-(1-Ethyl-propylamino)-2-(4-methoxy-2,6-dimethyl-phenoxy)-6-methyl-nicotinic acid methyl ester APCl M=![387.3], 1H NMR(CDCl$_3$)

EXAMPLE 203

2-(2,6-Dimethyl-4-[1,3,4]oxadiazol-2-yl-phenoxy)-4-(1-ethyl-propylamino)-6-methyl-nicotinic acid methyl ester 1H NMR(CDCl$_3$) d 8.43 (s, 1H), 8.22 (br d, ½H), 7.80 (s, 2H), 6.12 (s, 1H), 3.88 (s, 3H), 3.3–3.4 (m, 1H), 2.15–2.2 (m, 9H), 1.5–1.7 (m, 4H), 0.967 (t, 6H, J=7 Hz)

13C NMR(CDCl$_3$) d.

APCl+m/z=425.3 (M+1)

EXAMPLE 204

2-(4-Chloro-2-methoxy-phenoxy)-4-(1-ethyl-propylamino)-6-methyl-nicotinic acid methyl ester 1H NMR(CDCl$_3$) d 8.14 (d, 1H, J=8 Hz), 6.90–7.26 (m, 3H), 6.14 (s, 1H), 3.82 (s, 3H), 3.77 (s, 3H), 3.32–3.73 (m, 1H), 2.17 (s, 3H), 1.49–1.67 (m, 4H), 0.94 (t, 6H, J=7 Hz) ppm.

EXAMPLE 205

4-(1-Hydroxymethyl-propylamino)-2-(4-methoxy-2,6-dimethyl-phenoxy)-6-methyl-nicotinic acid methyl ester 1HNMR(CDCl$_3$) 8.21(d, 1H), 6.60(s, 2H), 6.30(s, 1H), 3.87(s, 3H), 3.78(s, 3H), 3.65(m, 3H), 2.17(s, 3H0, 2.09(s, 6H), 1.75(m, 1H), 1.61(m, 1H), 1.01(t, 3H)ppm

EXAMPLE 206

2-(4-Chloro-2-fluoro-6-methoxy-phenoxy)-4-(1-ethyl-propylamino)-6-methyl-nicotinic acid methyl ester APCl+m/z=411 (M+1), 413 (M+3)

EXAMPLE 207

2-(4-Chloro-2-methoxy-6-methyl-phenoxy)-4-(1-ethyl-propylamino)-6-methyl-nicotinic acid methyl ester 1H NMR(CDCl$_3$) d 8.16–8.20 (m, 1H), 6.82 (d, 1H, J=1.5 Hz), 6.78 (d, 1H, J=1.5 Hz), 6.09 (s, 1H), 3.85 (s, 3H), 3.72 (s, 3H), 3.3–3.8 (m, 1H), 2.12 (s, 3H), 1.51–1.67 (m, 4H), 0.95 (t, 6H, J=7 Hz)ppm.

APCl+m/z=407.2 (M+1), 409.2 (M+3)

EXAMPLE 208

2-(4-Chloro-2,6-dimethyl-phenoxy)-4-(1-methoxymethyl-propylamino)-6-methyl-nicotinic acid methyl ester 1H NMR(CDCl$_3$) d 8.2(d,1H), 7.02(s,2H), 6.14(s,1H), 3.87(s,3H), 3.6(m,1H), 3.56(m,1H), 3.4(m,1H), 3.39(s,3H), 2.10(s,3H), 2.07(s,6H), 1.78(m,1H), 1.61(m,1H), 1.00(t,3H) ppm.

EXAMPLE 209

2-(4-Bromo-2-methoxy-phenoxy)-4-(1-ethyl-propylamino)-6-methyl-nicotinic acid methyl ester 1H NMR(CDCl$_3$) d 8.14 (br d, 1H), 7.03–7.07 (m, 2H), 6.88 (d, 1H, J=8 Hz), 6.14 (s, 1H), 3.82 (s, 3H), 3.77 (s, 3H), 3.32–3.37 (m, 1H), 2.18 (s, 3H), 1.49–1.68 (m, 4H), 0.94 (t, 6H, J=7 Hz)

APCl+m/z=437.1 (M+1), 439.1 (M+3)

EXAMPLE 210

2-(4-Chloro-2-hydroxy-phenoxy)-4-(1-ethyl-propylamino)-6-methyl-nicotinic acid methyl ester The title compound was prepared by reacting 2-(4-chloro-2-methoxy-phenoxy)-4-(1-ethyl-propylamino)-6-methyl-nicotinic acid methyl ester with BBr$_3$ in methylene chloride at rt until all starting material was consumed. Standard work-up procedure gave the title compound.

APCl+m/z=379.2 (M+1), 381.2 (M+3)

EXAMPLE 211

2-(4-Chloro-2-ethoxy-phenoxy)-4-(1-ethyl-propylamino)-6-methyl-nicotinic acid methyl ester 1H NMR(CDCl$_3$) d 8.10 (br d, 1H), 6.98 (d, 1H, J=8 Hz), 6.86–6.91 (m, 2H), 6.14 (s, 1H), 3.97 (q, 2H, J=7 Hz), 3.83 (s, 3H), 3.32–3.37 (m, 1H), 2.16 (s, 3H), 1.50–1.68 (m, 4H), 1.19 (t, 3H, J=7 Hz), 0.94 (t, 6H, J=7 Hz) ppm. APCl+m/z=407.1 (M+1), 409.1 (M+3)

EXAMPLE 212

4-(2-Hydroxy-1-hydroxymethyl-ethylamino)-2-(4-methoxy-2,6-dimethyl-phenoxy)-6-methyl-nicotinic acid methyl ester 1HNMR(CDCl$_3$) 8.42(d, 1H), 7.02(s, 2H), 6.17(s, 1H), 3.89(m, 2H), 3.86(s, 3H), 3.85(m, 2H), 3.67(m, 1H), 2.10(s, 3H), 2.05(s, 6H)ppm

EXAMPLE 213

4-(1-Carboxy-propylamino)-2-(4-chloro-2,6-dimethyl-phenoxy)-6-methyl-nicotinic acid methyl ester A mixture of 2-(4-chloro-2,6-dimethyl-phenoxy)-4-(1-formyl-propylamino)-6-methyl-nicotinic acid methyl ester, 2-methyl-2-butene, excess NaClO$_2$, and NaH$_2$PO$_4$ was stirred at rt for 15 min. The mixture was quenched with sat. sodium bicarbonate and extracted with hexane. The aqueous layer was acidified to pH 4 and extracted twice with diethyl ether. The organic layer was separated, dried and concentrated to give the title compound. The crude material was purified by silica gel column chromatography to give the desired product as a white crystal after recrystallization. Anal. For C$_{20}$H$_{23}$N$_2$O$_5$Cl calc., C, 59.04; H, 5.70; N, 6.89; found C, 59.29; H, 5.73; N, 6.83.

EXAMPLE 214

4-(1-Carboxy-propylamino)-2-(4-chloro-2,6-dimethyl-phenoxy)-5-chloro-6-methyl-nicotinic acid methyl ester The title compound was prepared by the method analogous to that in Example 213, except with stirring overnight in the absence of 2-methyl-2-butene instead of a 15 minute reaction time.

EXAMPLE 215

4-(1-Carbamoyl-propylamino)-5-chloro-2-(4-chloro-2,6-dimethyl-phenoxy)-6-methyl-nicotinic acid methyl ester A mixture of 4-(1-carboxy-propylamino)-2-(4-chloro-2,6-dimethyl-phenoxy)-5-chloro-6-methyl-nicotinic acid methyl ester with excess of thionyl chloride in methylene chloride and stirred for 15 min. The mixture was concentrated to dryness. The residue was diluted with methylene chloride and ammonium was bubbled into the reaction mixture. After stirring for 30 min, the mixture was quenched with water, extracted with methylene chloride. The organic layer was concentrated to dryness. The residue was purified by silica gel Biotage to give the title compound. 1HNMR (CDCl$_3$) 7.02(s, 2H), 6.34(s, 1H), 5.92(d, 1H), 5.81(s, 1H), 4.05(m, 1H), 3.92(s, 3H), 2.27(s, 3H), 2.05(s, 6H), 1.80(m, 2H), 1.00(t, 3H)ppm The following compounds (Examples 216–223)were prepared by a method similar to that described above starting with a carboxylic acid and excess of thionyl chloride in methylene, concentration, quenching with ammonium, alkylamine, dialkylamine or alkanol (eg., methanol, ethanol, etc.):

EXAMPLE 216

2-(4-Chloro-2,6-dimethyl-phenoxy)-4-(1-methoxycarbonyl-propylamino)-6-methyl-nicotinic acid methyl ester 1HNMR(CDCl$_3$) 8.52(d, 1H), 7.02(s, 2H), 5.97(s, 1H), 4.09(m, 1H),3.89(s, 3H), 3.78(s, 3H), 2.09(s, 3H), 2.06(s, 6H), 1.98(m, 2H), 1.04(t, 3H)ppm

EXAMPLE 217

4-(1-Carbamoyl-propylamino)-2-(4-chloro-2,6-dimethyl-phenoxy)-6-methyl-nicotinic acid methyl ester 1H NMR(CDCl$_3$)d 8.56(d, 1H), 7.04(s, 2H), 6.38(s, 1H), 6.12(s, 1H), 5.44(s, 1H), 3.91(s, 3H), 3.88(m, 1H), 2.15(s, 1H), 2.07(s, 1H), 1.95(m, 2H), 1.24(t, 3H) ppm

EXAMPLE 218

2-(4-Chloro-2,6-dimethyl-phenoxy)-6-methyl-4-(1-methylcarbamoyl-propylamino)-nicotinic acid methyl ester 1HNMR(CDCl$_3$) 8.49(d, 1H), 7.05(s, 2H), 6.48(s, 1H), 6.08(s, 1H), 3.91(s, 3H), 3.90(m, 1H), 2.83(m, 3H), 2.15(s, 3H), 2.08(m, 6H), 1.08(t, 3H)ppm

EXAMPLE 219

5-Chloro-2-(4-chloro-2,6-dimethyl-phenoxy)-6-methyl-4-(1-methylcarbamoyl-propylamino)-nicotinic acid methyl ester 1HNMR(CDCl$_3$) 7.02(s, 2H), 6.42(m, 1H), 5.80(m, 1H), 3.96(m, 1H), 3.89(s, 3H), 2.86(d, 3H), 2.28(s, 3H), 2.04(m, 6H), 1.78(m, 2H), 0.98(t, 3H)ppm

EXAMPLE 220

2-(4-Chloro-2,6-dimethyl-phenoxy)-4-(1-dimethylcarbamoyl-propylamino)-6-methyl-nicotinic acid methyl ester 1HNMR(CDCl$_3$) 8.67(d, 1H), 7.02(s, 2H), 5.97(s, 1H), 4.39(m, 1H), 3.89(s, 3H), 3.13(s, 3H), 3.02(s, 3H), 2.13(s, 3H), 2.06(m, 6H), 1.92(m, 2H), 1.00(t, 3H) ppm

EXAMPLE 221

5-Chloro-2-(4-chloro-2,6-dimethyl-phenoxy)-4-(1-dimethylcarbamoyl-propylamino)-6-methyl-nicotinic acid methyl ester 1HNMR(CDCl$_3$) 7.02(s, 2H), 6.42(d, 1H), 4.66(m, 1H), 3.93(s, 3H), 3.06(s, 3H), 3.01 (s, 3H), 2.27(s, 3H), 1.82(m, 2H), 0.90(t, 3H) ppm

EXAMPLE 222

2-(4-Chloro-2,6-dimethyl-phenoxy)-6-methyl-4-[1-(pyrrolidine-1-carbonyl)-propylamino]-nicotinic acid methyl ester 1HNMR(CDCl$_3$) 8.61(d, 1H), 7.02(s, 2H), 5.97(s, 1H), 4.20(m, 1H), 3.89(s, 3H), 3.59(m, 4H), 2.13(s, 3H), 2.01(m, 12H), 1.02(t, 3H)ppm

EXAMPLE 223

5-Chloro-2-(4-chloro-2,6-dimethyl-phenoxy)-6-methyl-4-[1-pyrrolidine-1-carbonyl)-propylamino]-nicotinic acid methyl ester 1HNMR(CDCl$_3$) 7.02(s, 2H), 6.41(d, 1H), 4.44(m, 1H), 3.93(s, 3H), 3.56(m, 2H), 3.47(m, 2H), 2.26(s, 3H),2.06(s, 6H), 2.00(m, 6H), 0.91(t, 3H)ppm

EXAMPLE 224

2-(4-Chloro-2,6-dimethyl-phenoxy)-6-methyl-4-(1-methylaminomethyl-propylamino)-nicotinic acid methyl ester A mixture of 2-(4-chloro-2,6-dimethyl-phenoxy)-4-(1-formyl-propylamino)-6-methyl-nicotinic acid methyl ester (67 mg, 0.17 mmol) in dichloroethane (2 ml) was treated with methylamine, 1 drop of acetic acid, anhydrous Na$_2$SO$_4$ and sodium cyanoborohdride and stirred at rt. overnight. The mixture was quenched with water, extracted with methylene chloride. The organic layer was separated, dried, concentrated, and purified by silica gel Biotage using methylene chloride to 5% methanol in methylene chloride as eluent to give the title compound as an off-white solid. 1HNMR(CDCl$_3$) 8.07(d, 1H), 7.02(s, 2H), 6.29(s, 1H), 3.87(s, 3H), 3.80(m, 1H), 2.88(m, 2H), 2.56(s, 3H), 2.11(s, 3H), 2.06(s, 6H), 1.63(m, 2H), 0.99(t, 3H)ppm The following compounds (Examples 225–227) were prepared in a similar reductive amination method as described in Example 224.

EXAMPLE 225

2-(4-Chloro-2,6-dimethyl-phenoxy)-6-methyl-4-(1-pyrrolidin-1-ylmethyl-propylamino)-nicotinic acid methyl ester 1HNMR(CDCl$_3$) 8.11(d, 1H), 6.99(s, 2H), 6.12(s, 1H), 3.84(s, 3H), 3.54(m, 1H), 3.43(m, 2H), 2.56(m, 4H), 2.07(s, 3H), 2.06(s, 6H), 1.84(m, 6H), .96(t, 3H)ppm

EXAMPLE 226

2-(4-Chloro-2,6-dimethyl-phenoxy)-4-(1-cyclopropylaminomethyl-propylamino)-6-methyl-nicotinic acid methyl ester 1H NMR(CDCl$_3$) d 8.07(d, 1H), 7.02(s, 2H), 6.31(s, 1H), 3.87(s, 3H), 3.79(m, 1H), 2.96(m, 1H), 2.36(m, 1H), 2.11(s, 3H), 2.07(s, 6H), 1.83(m, 1H), 1.61(m, 1H), 0.99(t, 3H), 0.98(m, 4H)ppm

EXAMPLE 227

2-(4-Chloro-2,6-dimethyl-phenoxy)-4-{1-[(cyclopropylmethyl-amino)-methyl]-propylamino}-6-methyl-nicotinic acid methyl ester 1H NMR(CDCl$_3$) d 8.07(d, 1H), 7.02(s, 2H), 6.55(s, 1H), 4.12(m,1H), 3.88(s, 3H), 3.06(d, 2H), 2.87(m, 2H), 2.16(s, 3H),2.05(s, 6H), 2.03(m,1H), 1.69(m, 1H)1.25(m, 1H)1.03 (t, 3H), 0.66(m, 2H), 0.38(m, 2H)ppm

EXAMPLE 228

2-(4-Chloro-2,6-dimethyl-phenoxy)-4-(1-ethylaminomethyl-propylamino)-6-methyl-nicotinic acid methyl ester A solution of 2-(4-chloro-2,6-dimethyl-phenoxy)-4-(1-methanesulfonyloxymethyl-propylamino)-6-methyl-nicotinic acid methyl ester in acetonitrile was treated with sodium iodide, ethylamine and triethylamine. The resulting mixture was heated to 70° C. overnight, then 85° C. for 6 hrs, then 100° C. overnight until tlc showed no starting material. The resulting mixture was quenched with water and extracted with ethyl acetate. The organic layer was separated, dried, concentrated, and purified to give the title compound as an oil. 1H NMR(CDCl$_3$) d 8.06(d, 1H), 7.02(s, 2H), 6.31(s, 1H), 3.88(s, 3H), 3.86(m,1H), 2.85(m, 4H), 2.12(s,3H), 2.07(s, 6H), 1.64(m, 1H), 1.60(m, 1H), 1.27(m, 3H), .99(t, 3H)

EXAMPLE 229

2-(4-Chloro-2,6-dimethyl-phenoxy)-4-{1-[(ethyl-methyl-amino)-methyl]-propylamino}-6-methyl-nicotinic acid methyl ester 1H NMR(CDCl$_3$) d 8.18 (d, 1H), 7.02(s, 2H), 6.19(m, 1H), 3.86(s, 3H), 3.56(m, 3H), 3.37(m, 2H), 2.11 (s, 3H), 2.07(s, 6H), 1.80(m, 1H), 1.60(m,2H),1.25(m,4H), 0.97(t, 3H) ppm

EXAMPLE 230

4-(1-Butylaminomethyl-propylamino)-2-(4-chloro-2,6-dimethyl-phenoxy)-6-methyl-nicotinic acid methyl ester 1H NMR(CDCl$_3$) d 8.07(d, 1H) 7.02(s, 1H), 6.25(s, 1H), 3.87(s, 3H), 3.79(m, 1H), 2.79 (m, 2H), 2.69(m ,2H), 2.10(s, 3H), 2.07(s, 6H), 1.75(m, 2H), 1.57(m, 4H), 1.00(t, 3H), 0.92(t, 6H)ppm

EXAMPLE 231

2-(4-Chloro-2,6-dimethyl-phenoxy)-4-{1-[(cyclopropylmethyl-propyl-amino)-methyl]-propylamino}-6-methyl-nicotinic acid methyl ester 1H NMR(CDCl$_3$) d 8.01(d, 1H), 7.02(s, 2H), 6.13(s, 1H), 3.85(s, 3H), 3.48(m, 1H), 2.58(m, 2H), 2.37(m, 1H), 2.09(s, 3H), 2.07(s, 6H), 1.82(m, 1H) 1.42(m, 2H), 1.25(m 4H), 0.97(t, t, 3H), 0.86(m, 6H) ppm

EXAMPLE 232

2-(4-Chloro-2,6-dimethyl-phenoxy)-6-methyl-4-(1-propylaminomethyl-propylamino)-nicotinic acid methyl ester 1H NMR(CDCl$_3$) d 8.09(d, 1H), 7.02(s, 2H), 6.19(s, 1H), 3.86(s, 3H), 3.60(m, 1H), 2.76(m, 2H), 2.61(t, 2H), 2.10(s, 3H), 2.07(s, 6H), 1.61(m, 6H), 0.97(t,3H), 0.91(t, 3H)ppm

EXAMPLE 233

2-(4-Chloro-2,6-dimethyl-phenoxy)-4-(1-{[(furan-2-ylmethyl)-amino]-methyl}-propylamino)-6-methyl-nicotinic acid methyl ester 1H NMR(CDCl$_3$) d 8.09(d, 1H), 7.37(s, 1H), 7.02(s,2H), 6.31(dd, 2H), 6.17(s, 1H), 3.87(s, 3H), 3.84(s, 2H), 3.58(m, 1H), 2.75(m, 2H), 2.09(s,3H), 2.07(s, 6H), 1.70(m, 1H), 1.58(m, 1H), 0.95(t, 3H)ppm

EXAMPLE 234

2-(4-Chloro-2,6-dimethyl-phenoxy)-4-{1-[(2-methoxy-ethylamino)-methyl]-propylamino}-6-methyl-nicotinic acid methyl ester 1H NMR(CDCl$_3$) d 8.10(d, 1H), 7.02(s, 2H), 6.19(s, 1H), 3.87(s, 3H), 3.61(m, 1H), 3.51(m, 2H), 3.34(s, 3H), 2.84(m, 2H), 2.79(m, 2H), 2.10(s, 3H), 2.07(s, 6H), 1.71(m, 1H), 1.57(m, 1H), 0.98(t, 3H)ppm

EXAMPLE 235

2-(4-Chloro-2,6-dimethyl-phenoxy)-4-(1-dimethylaminomethyl-propylamino)-6-methyl-nicotinic acid methyl ester 1HNMR(CDCl$_3$) 8.14(d, 1H), 7.02(s, 2H), 6.10(s, 1H), 3.86(s, 3H), 3.53(m, 1H), 2.44(m, 2H), 2.29(s, 6H), 2.10(s, 3H), 2.07(s, 6H), 1.78(m, 1H), 1.56(m, 1H), 0.97(t, 3H)ppm

EXAMPLE 236

4-[(2-Butylamino-ethyl)-ethyl-amino]-2-(4-chloro-2,6-dimethyl-phenoxy)-6-methyl-nicotinic acid methyl ester 1HNMR(CDCl$_3$) 7.00(s, 2H), 6.31 (s, 1H), 3.88(s, 3H), 3.41(t, 2H), 3.26(m, 2H), 2.82(t, 2H), 2.65(t, 2H), 2.15(s, 3H), 2.05(s, 6H), 1.51(m, 2H), 1.34(m, 2H), 1.12(t, 3H), 0.89(t, 3H)ppm

EXAMPLE 237

2-(4-Chloro-2,6-dimethyl-phenoxy)-4-(S,S)-(1-ethyl-2-methylamino-propylamino)-6-methyl-nicotinic acid methyl ester The title compound was prepared by a reductive amination as shown above starting with 2-(4-Chloro-2,6-dimethyl-phenoxy)-4-(1-ethyl-2-oxo-propylamino)-6-methyl-nicotinic acid methyl ester and methyl amine. APCl M+1 [420.2], 1H NMR(CDCl$_3$)

EXAMPLE 238

2-(4-Chloro-2,6-dimethyl-phenoxy)-4-(S,R)-(1-ethyl-2-methylamino-propylamino)-6-methyl-nicotinic acid methyl ester The title compound was prepared by a reductive amination as shown above starting with 2-(4-Chloro-2,6-dimethyl-phenoxy)-4-(1-ethyl-2-oxo-propylamino)-6-methyl-nicotinic acid methyl ester and methyl amine. APCl M+1 [420.2], 1H NMR(CDCl$_3$)

EXAMPLE 239

2-(4-Methoxy-2,6-dimethyl-phenoxy)-6-methyl-4-(1-methylsulfanylmethyl-propylamino)-nicotinic acid methyl ester A mixture of 2-(4-methoxy-2,6-dimethyl-phenoxy)-4-(1-methanesulfonyloxymethyl-propylamino)-6-methyl-nicotinic acid methyl ester and sodium iodide in acetonitrile was stirred at rt for 2 hr, then NaSMe was added. The mixture was heated at 60° C. overnight. DMSO and additional NaSMe were added and heated for additional hours until all starting material was consumed. The mixture was quenched with water, extracted with ethyl acetate. The organic layer was separated, dried, concentrated, and purified to give the title compound.

1HNMR(CDCl$_3$) 8.23(d, 1H), 6.59(s, 2H), 6.10(s, 1H), 3.87(s, 3H), 3.78(s, 3H), 3.60(m, 1H), 2.75(m, 1H), 2.65(m, 1H), 2.14(s, 3H), 2.08(m, 9H), 1.85(m, 1H), 1.66(m, 1H), 1.00(t, 3H)ppm The following compounds (Examples 240–243) were prepared by the method similar to that described in Example 239 starting with an appropriate 2-(substituted-phenoxy)-4-(1-methanesulfonyloxymethyl-propylamino)-3,6-substituted-pyridine with an appropriate nucleophile:

EXAMPLE 240

2-(4-Methoxy-2,6-dimethyl-phenoxy)-6-methyl-4-(1-[1,2,4]triazol-1-ylmethyl-propylamino)-nicotinic acid methyl ester 1H(CDCl$_3$) 8.23(d, 1H), 8.02(s, 1H), 7.95(s, 2H), 5.92(s, 1H), 6.59(s, 2H), 5.93(s, 1H), 4.31(m, 1H), 4.22(m, 1H), 3.93(m, 1H), 3.87(s, 3H), 3.77(s, 3H), 2.10(s, 3H), 2.07(s, 6H), 1.70(m, 1H), 1.59(m, 1H), 1.04(t, 3H)ppm

EXAMPLE 241

2-(4-Chloro-2,6-dimethyl-phenoxy)-6-methyl-4-(1-methylsulfanylmethyl-propylamino)-nicotinic acid methyl ester 1HNMR(CDCl$_3$) 8.27(d, 1H), 7.02(s, 2H), 6.12(s, 1H), 3.87(s, 3H), 3.61(m, 1H), 2.70(m, 2H), 2.17(s, 3H), 2.14(s, 3H), 2.08(s, 6H), 1.85(m, 2H), 1.00(t, 3H)ppm

EXAMPLE 242

2-(4-Chloro-2,6-dimethyl-phenoxy)-4-(2-ethyl-aziridin-1-yl)-6-methyl-nicotinic acid methyl ester 7.02(s,2H), 6.38(s,1H), 3.95(s,3H), 2.27(m,1H), 2.18(s,3H), 2.15(m,2H), 2.06(s,6H), 1.75(m,1H), 1.63(m,1H), 1.06(t,3H)ppm.

EXAMPLE 243

2-(4-Chloro-2,6-dimethyl-phenoxy)-6-methyl-4-[1-(3H-[1,2,3]triazol-4-ylsulfanylmethyl)-propylamino]-nicotinic acid methyl ester 1HNMR(CDCl$_3$) 8.32(d, 1H), 7.54(s, 1H), 6.95(s, 2H), 6.13(s, 1H), 3.87(s, 3H), 3.67(m, 1H), 3.20(m, 1H), 3.05(m, 1H), 2.05(m, 9H), 1.99(m, 1H), 1.67(m, 1H), 1.01(t, 3H)ppm

EXAMPLE 244

2-(4-Chloro-2,6-dimethyl-phenoxy)-4-(1-hydroxymethyl-3-methanesulfonyl-propylamino)-6-methyl-nicotinic acid methyl ester The title compound was prepared by oxidation of 2-(4-Chloro-2,6-dimethyl-phenoxy)-4-(1-hydroxymethyl-3-methylsulfanyl-propylamino)-6-methyl-nicotinic acid methyl ester with m-chloroperbenzoic acid in methylene chloride at rt. for 2 hrs. 1H NMR(CDCl$_3$) d 8.32(d,1H), 7.04(s,2H), 6.23(s,1H), 3.88(s,3H), 3.7–3.9(m,3H), 3.1–3.3 (m,2H), 2.95(s,3H), 2.0–2.4(m,2H). 2.13(s,3H), 2.07(s,6H) ppm.

The following compounds (Examples 245–248) were prepared by the method analogous to that described in Example 188:

EXAMPLE 245

2-(4-Ethoxy-2,6-dimethyl-phenoxy)-6-methyl-4-(tetrahydro-furan-3-ylamino)-nicotinic acid methyl ester 1H NMR(CDCl$_3$) d 8.35(d, 1H), 6.59(s, 2H), 6.08(s, 1H), 4.03(m, 1H), 4.01(m, 4H), 3.99(m, 1H), 3.92(s, 3H), 3.89(m, 1H), 2.34(m, 1H), 2.25(m, 3H), 2.08(s, 6H), 1.39(t, 3H)ppm

EXAMPLE 246

2-[4-(2-Methoxy-ethoxy)-2,6-dimethyl-phenoxy]-6-methyl-4-(tetrahydro-furan-3-ylamino)-nicotinic acid methyl ester 1H NMR(CDCl$_3$) d 8.30(d, 1H), 6.62(s, 2H), 6.07(s, 1H), 4.10(m, 3H), 4.02(m, 2H), 3.98(m, 1H), 3.85(s, 2H), 3.75(m, 3H), 3.45(s, 3H), 2.32(m, 1H), 2.19(s, 3H), 2.07(s, 6H)ppm

EXAMPLE 247

2-(2,6-Dimethyl-4-trifluoromethoxy-phenoxy)-6-methyl-4-(tetrahydro-furan-3-ylamino)-nicotinic acid methyl ester 1H NMR(CDCl$_3$) d 8.29 (d, 1H, J=6 Hz), 6.91 (s, 2H), 6.06 (s, 1H), 4.11–4.33 (m, 1H), 3.97–4.05 (m, 2H), 3.89–3.93 (m, 1H), 3.87 (s, 3H), 3.72–3.76 (m, 1H), 2.31–2.35 (m, 1H), 2.14 (s, 3H), 2.10 (s, 6H), 1.94–1.96 (m, 1H)ppm.

APCl+m/z=441.2 (M+1)

EXAMPLE 248

2-(4-Chloro-2,6-dimethyl-phenoxy)-6-methyl-4-(R)-(tetrahydro-furan-3-ylamino)-nicotinic acid methyl ester APCl+m/z=391.3 (M+1)

EXAMPLE 249

2-(4-Chloro-2,6-dimethyl-phenoxy)-4-(1-hydroxymethyl-3-iodo-propylamino)-6-methyl-nicotinic acid methyl ester APCl [M+1]518.9, 520.9

EXAMPLE 250

2-(4-Chloro-2,6-dimethyl-phenoxy)-4-(1-hydroxymethyl-3-methanesulfinyl-propylamino)-6-methyl-nicotinic acid methyl ester 1H NMR(CDCl$_3$) d 8.31(d,1H), 7.03(s,2H), 6.24(s,0.5H), 6.28(s,0.5H), 3.87(s,3H), 3.65–3.9(m,3H), 2.7–3.0(m,2H), 2.60(s,3H), 2.0–2.4(m,2H), 2.14(s,3H), 2.07(s,6H) ppm.

EXAMPLE 251

2-(4-Cyclopropyloxy-2,6-dimethyl-phenoxy)-6-methyl-4-(tetrahydro-furan-3-ylamino)-nicotinic acid methyl ester 1H NMR (CDCl$_3$) d 8.32(d, 1H), 6.73(s, 2H), 6.07(s, 1H), 4.13(m,1H), 4.01(m, 4H), 3.98(m, 1H), 3.85(s, 3H), 3.72(m, 2H), 2.22(s, 3H), 2.09(s, 6H0, 0.87(m,2H), 0.75(m, 4H)ppm

EXAMPLE 252

2-(4-Chloro-2,6-dimethoxy-phenoxy)-6-methyl-4-(tetrahydro-furan-3-ylamino)-nicotinic acid methyl ester

EXAMPLE 253

4-sec-Butylamino-6-methyl-2-(2,4,6-trimethyl-pyridin-3-yloxy)-nicotinic acid methyl ester 1H NMR(CDCl$_3$) 8.08(d, 1H), 686(s, 1H), 6.09(s, 1H), 3.86(s, 3H), 3.48(m, 1H), 2.49(s, 3H), 2.31 (s, 3H), 2.08(s, 6H), 1.63(m, 2H), 1.21 (d, 3H), 0.98(t, 3H)ppm

EXAMPLE 254

2-(4-Chloro-2,6-dimethyl-phenoxy)-4-{ethyl-[2-(ethyl-methyl-amino)-ethyl]-amino}-6-methyl-nicotinic acid methyl ester

EXAMPLE 255

2-(4-Chloro-2,6-dimethyl-phenoxy)-4-[ethyl(2-propylamino-ethyl)-amino]-6-methyl-nicotinic acid methyl ester

EXAMPLE 256

4-(1-Ethyl-propylamino)-6-methyl-2-(2,4,6-trimethyl-pyridin-3-yloxy)-nicotinic acid methyl ester 1H NMR(CDCl$_3$) 8.09(d, 1H), 6.86(s, 1H), 6.08(s, 1H), 3.86(s, 3H), 3.33(m, 1H), 2.49(s, 3H), 2.31(s, 3H), 2.07(s, 6H), 1.63(m, 4H), 0.94(t, 6H)ppm 1H NMR(CDCl$_3$) d 8.39 d, 1H, J=6 Hz), 6.63 (s, 2H), 6.06 (s, 1H), 4.08–4.15 (m, 1H), 3.95–4.05 (m, 2H), 3.88–3.92 (m, 1H), 3.86 (s, 3H), 3.73 (s, 6H), 3.67–3.73 (m, 1H), 2.26–2.35 (m, 1H), 2.14 (s, 3H), 1.89–1.96 (m, 1H) ppm.

The following Examples 257–287 relate to other compounds of formula I of the invention, wherein R$_4$ is —C(O)NR$_{24}$R$_{25}$:

The following compounds (Examples 257–280) were prepared by a method analogous to that in Example 113 starting with the corresponding nicotinic acid or pyrimidine-5-carboxylic derivative and quenching with an appropriate nucleophile; these compounds can also be prepared by coupling of 2-(substituted-phenoxy)-6-methyl-4-chloro-nicotinamide and/or -N-substituted-nicotinamide with an appropriate amine in NMP at 130–160° C.:

EXAMPLE 257

2-(4-Chloro-2,6-dimethyl-phenoxy)-6-methyl-4-(tetrahydro-furan-3-ylamino)-nicotinamide 1H NMR(CDCl$_3$) d 9.99(d,1H), 7.85(brs, 1H), 7.07(s, 2H), 6.13(s,1H), 5.62(brs,1H), 3.7–4.2(m,5H), 2.95(d,3H), 2.31 (m,1H), 2.20(s,3H), 2.09(s,6H), 2.01 (m,1H) ppm.

EXAMPLE 258

2-(4-Chloro-2,6-dimethyl-phenoxy)-4-(1-hydroxymethyl-3-methylsulfanyl-propylamino)-6-methyl-nicotinamide 1H NMR(CDCl$_3$) d 9.78(d,1H), 7.97(brs, 1H), 7.06(s, 2H), 6.32(s,1H), 5.77(brs,1H), 3.6–3.9(m,3H), 2.5–2.7(m, 2H), 2.0–2.2(m, 12H), 1.8–2.0(m,2H)ppm.

EXAMPLE 259

2-(4-Chloro-2,6-dimethyl-phenoxy)-6,N-dimethyl-4-(S)-(tetrahydro-furan-3-ylamino)-nicotinamide 1H NMR(CDCl$_3$) d 10.00(d,1H), 8.05(brs, 1H), 7.06(s, 2H), 6.10(s,1H), 4.09(m,1H), 3.96–4.05(m,3H), 3.73(m, 1H), 2.95(d,3H), 2.31(m,1H), 2.12(s,3H), 2.06(s,6H), 1.96 (m,1H) ppm.

EXAMPLE 260

2-(4-Chloro-2,6-dimethyl-phenoxy)-4-(1-ethyl-propylamino)-6,N-dimethyl-nicotinamide 1H NMR(CDCl$_3$) d 9.78(d,1H), 8.10(brs, 1H), 7.06(s, 2H), 6.13(s,1H), 3.32(m,1H), 2.96(d,3H), 2.09(s,3H), 2.08 (s,6H), 1.65(m,4H), 0.96(t,6H)ppm.

EXAMPLE 261

4-sec-Butylamino-2-(4-chloro-2,6-dimethyl-phenoxy)-6,N-dimethyl-nicotinamide

1H NMR(CDCl$_3$) d 9.78(d,1H), 8.04(brs, 1H), 7.07(s, 2H), 6.14(s,1H), 3.46(m,1H), 2.95(d,3H), 2.15(s,3H), 2.09 (s,6H), 1.1.58(m,2H), 1.23(d,3H), 0.99(t,6H)ppm.

EXAMPLE 262

4-(1-Ethyl-propylamino)-2-(4-methoxy-2,6-dimethyl-phenoxy)-6-methyl-nicotinamide Mp=184° C. Found: C, 67.68; H, 8.12; N, 10.81; Calc: C, 67.90; H, 7.87; N, 11.31 1H(CDCl$_3$) 9.67(d, 1H), 8.06(m, 1H) 6.61 (s, 2H), 6.11 (s, 1H), 5.48(s, 1H), 3.79(s, 3H), 3.32(m, 1H), 2.09(s, 9H), 1.61 (s, 4H), 0.95(t, 6H)ppm

EXAMPLE 263

4-(1-Ethyl-propylamino)-2-(4-methoxy-2,6-dimethyl-phenoxy)-6,N-dimethyl-nicotinamide 1H(CDCl$_3$) 9.78(d, 1H), 8.22(m, 1H), 6.60(s, 2H), 6.10(s, 1H), 3.78(s, 3H), 3.25(m, 1H), 2.93(d, 3H), 2.07(s, 9H), 1.61(m, 4H), 0.95(t. 6H)ppm

EXAMPLE 264

2-(4-Methoxy-2,6-dimethyl-phenoxy)-4-(1-methoxymethyl-propylamino)-6-methyl-nicotinamide 1HNMR(CDCl$_3$) 9.80(d, 1H), 8.04(s, 1H), 6.61(s, 2H), 6.18(s, 1H), 5.62(s, 1H), 3.78(s, 3H), 3.51(m, 2H), 3.39(s, 3H), 2.09(s, 3H), 2.08(s, 6H), 1.79(m, 1H), 1.59(m, 1H), 0.99(t, 3H)ppm

EXAMPLE 265

2-(4-Methoxy-2,6-dimethyl-phenoxy)-4-(1-methoxymethyl-propylamino)-6,N-dimethyl-nicotinamide 1HNMR(CDCl$_3$) 9.92(d, 1H), 8.22(s, 1H), 6.62(s, 2H), 6.19(s, 1H), 3.79(s, 3H), 3.5(m, 2H), 3.38(s, 3H), 2.94(d, 3H), 2.12(s, 3H), 2.08(s, 6H), 1.80(m, 1H), 1.61(m, 1H), 1.00(t, 3H)ppm

EXAMPLE 266

4-(1-Hydroxymethyl-propylamino)-2-(4-methoxy-2,6-dimethyl-phenoxy)-6,N-dimethyl-nicotinamide 1HNMR(CDCl$_3$) 9.79(d, 1H), 8.28(d, 1H), 6.62(s, 2H), 6.24(s, 1H), 3.79(s, 3H), 3.70(m, 2H), 3.54(m, 1H), 2.94(d, 3H), 2.08(s, 6H), 1.62(m, 2H), 1.01 (t, 3H)ppm

EXAMPLE 267

4-sec-Butylamino-2-(4-methoxy-2,6-dimethyl-phenoxy)-6,N-dimethyl-nicotinamide

1HNMR(CDCl$_3$) 9.76(d, 1H), 8.26(d, 1H), 6.61(s, 2H), 6.12(s, 1H), 3.79(s, 3H), 3.46(m, 1H), 2.94(d, 3H), 2.09(s, 3H), 2.07(s, 6H), 1.64(m, 2H), 1.24(m, 3H), 0.98(t, 3H)ppm

EXAMPLE 268

2-(4-Chloro-2,6-dimethyl-phenoxy)-4-(S)-(1-methoxymethyl-propylamino)-6,N-dimethyl-nicotinamide Anal. For C$_{21}$H$_{28}$ClN$_3$O$_3$ calc. C, 62.14%; H, 6.95%; N, 10.35%; found C, 62.12%; H, 6.95%; N, 10.42%.

EXAMPLE 269

2-(4-Chloro-2,6-dimethyl-phenoxy)-4-(S)-(1-methoxymethyl-propylamino)-6-methyl-nicotinamide Anal. For $C_{20}H_{26}ClN_3O_3$ calc. C, 61.30%; H, 6.69%; N, 10.725%; found C, 60.97%; H, 6.53%; N, 10.47%.

EXAMPLE 270

2-(4-Chloro-2,6-dimethyl-phenoxy)-6,N-dimethyl-4-(1-methylsulfanylmethyl-propylamino)-nicotinamide 1HNMR(CDCl$_3$) 9.97(d, 1H), 8.1(brs, 1H), 7.06(s, 2H), 6.16(s, 1H), 3.56(m, 1H), 2.96(s, 3H), 2.6–2.8(m,2H), 2.17 (s, 3H), 2.11(s,3H), 2.08(s, 6H), 1.6–1.9(m, 2H), 1.24(m, 3H), 1.00(t, 3H)ppm

EXAMPLE 271

2-(4-Chloro-2,6-dimethyl-phenoxy)-6-methyl-4-(1-methylsulfanylmethyl-propylamino)-nicotinamide 1HNMR(CDCl$_3$) 9.89(d, 1H), 7.9(brs, 1H), 7.06(s, 2H), 6.16(s, 1H), 3.56(m,1H), 2.6–2.8(m,2H), 2.17(s, 3H), 2.11 (s,3H), 2.07(s, 6H), 1.6–1.9(m, 2H), 1.24(m, 3H), 0.99(t, 3H)ppm

EXAMPLE 272

2-(4-Chloro-2-methoxy-phenoxy)-4-(1-ethyl-propylamino)-6,N-dimethyl-nicotinamide 1H NMR(CDCl$_3$) d 9.40 (d, 1H, J+8 Hz), 8.10 (br s, 1H), 7.17 (d, 1H, J=9 Hz), 6.94–6.96 (m, 2H), 6.14 (s, 1H), 3.79 (s, 3H), 3.27–3.31 (m, 1H), 2.93 (d, J=5 Hz) 2.14 (s, 3H), 1.51–1.66 (m, 4H), 0.95 (t, 6H, J=7 Hz) ppm. Cl+m/z=392.2 (M+1), 394.2 (M+3)

EXAMPLE 273

2-(4-Chloro-2-methoxy-phenoxy)-4-(1-ethyl-propylamino)-6-methyl-nicotinamide

1H NMR(CDCl$_3$) d 9.40 (d, 1H), 7.92 (brs, 1H), 7.17 (d, 1H, J=9 Hz), 6.94–6.96 (m, 2H), 6.15 (s, 1H), 5.48 (br s, 1H), 3.77 (s, 3H), 3.28–3.36 (m, 1H), 2.16 (s, 3H), 1.52–1.66 (m, 4H), 0.94 (t, 6H, J=7 Hz) ppm.
APCl+m/z=378.1 (M+1), 380.1 (M+3)

EXAMPLE 274

2-(4-Chloro-2,6-dimethyl-phenoxy)-4-(1-cyclopropylmethoxymethyl-propylamino)6-methyl-nicotinamide 1H NMR(CDCl$_3$) d 9.70 (d, 1H), 7.90 (brs, 1H), 7.05 (s, 1H), 6.22 (s, 1H), 5.6 (br s, 1H), 3.57 (m, 2H), 3.43(m,1H), 3.33(d,3H), 2.09(s,6H), 2.07 (s, 3H), 1.5–1.9 (m, 2H), 0.9–1.0(m,4H), 0.53(m,2H), 0.50(m,2H) ppm.

EXAMPLE 275

2-(4-Chloro-2,6-dimethyl-phenoxy)-4-(1-ethoxymethyl-propylamino)-6-methyl-nicotinamide 1H NMR(CDCl$_3$) d 9.75 (d, 1H), 7.90 (brs, 1H), 7.05 (s, 1H), 6.21 (s, 1H), 5.6 (br s, 1H), 3.3–3.6(m,4H), 2.08(s,6H), 2.07 (s, 3H), 1.5–1.9 (m, 2H), 1.20(t,3H), 1.00(t,3H) ppm.

EXAMPLE 276

2-(4-Chloro-2,6-dimethyl-phenoxy)-4-(1-ethoxymethyl-propylamino)-N-ethyl-6-methyl-nicotinamide 1H NMR(CDCl$_3$) d 9.78 (d, 1H), 8.09 (t, 1H), 7.06 (s, 1H), 6.22 (s, 1H), 5.6 (br s, 1H), 3.3–3.6(m,6H), 2.09(s,3H), 2.08 (s, 6H), 1.5–1.9 (m, 2H), 1.20–1.4(m,6H), 1.00(t,3H) ppm.

EXAMPLE 277

2-(4-Chloro-2,6-dimethyl-phenoxy)-4-(1-ethoxymethyl-propylamino)-6,N-dimethyl-nicotinamide 1H NMR(CDCl$_3$) d 9.8(d, 1H), 8.1 (brs, 1H), 7.06 (s, 1H), 6.22 (s, 1H), 3.54(m,3H), 3.38(m,1H), 2.94(d,3H), 2.08(s, 6H), 2.07 (s, 3H), 1.83(m,1H), 1.60(m,1H), 1.20(t,3H), 1.00(t,3H) ppm.

EXAMPLE 278

2-(4-Bromo-2-methoxy-phenoxy)-4-(1-ethyl-propylamino)-6,N-dimethyl-nicotinamide

1H NMR(CDCl$_3$) d 9.41 (br d, 1H), 8.08 (br s, 1H), 7.09–7.12 (m, 3H), 6.15 (s, 1H), 3.79 (s, 1H), 3.28–3.33 (m, 1H), 2.93 (d, 3H, J=5 Hz), 2.15 (s, 3H), 1.501–1.65 (m, 4H), 0.95 (t, 6H, J=8 Hz)
APCl+m/z=436.1 (M+1), 438.1 (M+3)

EXAMPLE 279

2-(4-Bromo-2-methoxy-phenoxy)-4-(1-ethyl-propylamino)-6-methyl-nicotinamide

1H NMR(CDCl$_3$) d 9.39 (br d, 1H), 7.91 (br s, 1H), 7.09–7.11 (m, 3H), 6.15 (s, 1H), 5.49 (br s, 1H), 3.77 (s, 3H), 3.29–3.34 (m, 1H), 2.15 (s, 3H), 1.51–1.67 (m, 4H), 0.94 (t, 6H, J=7 Hz) ppm.
APCl+m/z=422.1 (M+1), 424.1 (M+3)

EXAMPLE 280

2-(4-Chloro-2,6-dimethyl-phenoxy)-4-(1-chloromethyl-propylamino)-6-methyl-nicotinamide 1H NMR(CDCl$_3$) d 9.93(d,1H), 7.9(brs,1H), 7.06(s,2H), 6.16(s,1H), 5.6(brs,1H), 3.4–3.7(m,3H), 2.1(s,3H), 2.08(s, 6H), 1.9(m,1H), 1.65(m,1H), 1.03(t,3H) ppm.

EXAMPLE 281

2-(4-Chloro-2,6-dimethyl-phenoxy)-4-(1-formyl-propylamino)-6-methyl-nicotinamide A mixture of 2-(4-chloro-2,6-dimethyl-phenoxy)-4-(1-hydroxymethyl-propylamino)-6-methyl-nicotinamide and Dess-Martin reagent in methylene chloride/DMSO was stirred at rt for 4 hr. The title compound was isolated after standard work-up and silica gel Biotage purification. 1H NMR(CDCl$_3$) d 9.52(s,1H), 8.00(brs,1H), 7.06(s,22H), 5.99 (s,1H), 5.8(brs,1H), 3.85(m,1H), 2.09(s,3H), 2.08(s,6H), 1.8–2.2(m,2H), 1.08(t,3H) ppm.

EXAMPLE 282

4-(1-Formyl-propylamino)-2-(4-methoxy-2,6-dimethyl-phenoxy)-6,N-dimethyl-nicotinamide The title compound was prepared by a method analogous to that described in Example 281.

1HNMR(CDCl$_3$) 9.51(s, 1H), 8.32(m, 1H), 6.62(s, 2H), 5.97(s, 1H), 3.81(m, 1H), 3.79(s, 3H), 2.96(m, 3H), 2.08(m, 9H), 1.89(m, 2H), 1.09(t, 3H)ppm

EXAMPLE 283

2-(4-Chloro-2,6-dimethyl-phenoxy)-4-(1-ethyl-2-hydroxy-propylamino)-6-methyl-nicotinamide To a solution of MeMgBr in dry THF was added a solution of 2-(4-chloro-2,6-dimethyl-phenoxy)-4-(1-formylpropylamino)-6-methyl-nicotinamide in dry THF at −78° C. The mixture was stirred at −78° C. for 2 hr, then quenched with dilute acid. After standard extraction and purification, the title compound was obtained. 1H NMR(CDCl$_3$) d 9.8 (d,1H), 7.9(nbrs,1H), 7.05(s,2H), 6.27(s,0.5H), 6.24(s, 0.5H), 5.6(brs,1H), 3.91(m,0.5H), 3.89(m,0.5H), 3.51(m, 0.5H), 3.3(m,0.5H), 2.09(s,9H), 1.5–1.8(m,2H), 1.26(d,3H), 0.98(t,3H) ppm.

EXAMPLE 284

4-(1-Ethyl-2-methoxy-propylamino)-2-(4-methoxy-2,6-dimethyl-phenoxy)-6,N-dimethyl-nicotinamide 1HNMR(CDCl$_3$) 9.87(d, 1H), 8.26(d, 1H), 6.61(s, 2H), 6.16(s, 1H), 3.79(s, 3H), 3.46(m, 1H), 3.40(s, 3H), 2.94(d, 3H), 2.08(s, 9H), 1.76(m, 1H), 1.65(m, 1H), 1.25(m, 1H), 1.17(d, 3H), 0.98(t, 3H)ppm mp=122.6° C.

EXAMPLE 285

2-(4-Bromo-2,6-dimethyl-phenoxy)-4-(1-ethyl-propylamino)-6-methyl-nicotinamide

To a mixture of 2-chloro-4-(1-ethyl-propylamino)-6-methyl-nicotinamide and 2,6-dimethyl-4-bromo-phenol in NMP was added t-BuOK. The resulting mixture was heated in a 160° C. oil bath overnight. The mixture was quenched with water and extracted with ethyl acetate. The organic layer was separated, dried and concentrated, then purified through silica gel Biotage to give the title compound. 1H NMR(CDCl$_3$) d 9.69(d,1H), 7.89(brs,1H), 7.20(s,2H), 6.13 (s,1H), 5.5(brs,1H), 3.3(m,1H), 2.10(s,3H), 2.09(s,6H), 1.6 (m,4H), 0.95(t,6H) ppm.

EXAMPLE 286

4-(1-Ethyl-propylamino)-6,N-dimethyl-2-(2,4,6-trimethyl-pyridin-3-yloxy)-nicotinamide 1H(CDCl$_3$) 9.74(d, 1H), 8.08(s, 1H), 6.90(s, 1H), 6.12(s, 1H), 3.31(m,1H), 2.96(d, 3H), 2.51 (s, 3H), 2.30(s, 3H), 2.08(s, 3H), 2.05(s, 3H), 1.60(m, 4H), 0.95(t, 3H)ppm

EXAMPLE 287

4-(1-Ethyl-propylamino)-6-methyl-2-(2,4,6-trimethyl-pyridin-3-yloxy)-nicotinamide MP=164.3° C. 1H NMR (CDCl$_3$) 9.65(d, 1H), 7.8(s, 1H), 6.91(s, 1H), 6.14(s, 1H), 5.50(s, 1H), 3.32(m, 1H), 2.53(s, 3H), 2.34(s, 3H), 2.17(s, 3H), 2.10(s, 3H), 1.60(m, 4H), 0.95(t, 6H)ppm The following Examples 288–294 relate to other compounds of formula I of the invention, wherein R$_4$ is —C(O)R$_{24}$, for example —C(O)CH$_3$:

EXAMPLE 288

1-[4-(1-Ethyl-propylamino)-2-(4-methoxy-2,6-dimethyl-phenoxy)-6-methyl-pyridin-3-yl]-ethanone 1HNMR(CDCl$_3$) 9.74(d, 1H), 6.61(s, 2H), 6.10(s, 1H), 3.79(s, 3H), 3.39(m, 1H), 2.73(s, 3H), 2.10(s, 9H), 1.62(m, 4H), 0.94(t, 6H)ppm

EXAMPLE 289

N-[3,6-Dimethyl-2-(2,4,6-trimethyl-phenoxy)-pyridin-4-yl]-N-(2-pyrrolidin-1-yl-ethyl)-acetamide 1H NMR(CDCl$_3$) d 6.89 (s, 2H), 6.60 (s, 1H), 4.00–4.07 (m, 1H), 3.53–3.59 (m, 1H), 2.59–2.72 (m, 2H), 2.52 (br s, 4H), 2.30 (s, 3H), 2.24 (s, 3H), 2.22 (s, 3H), 2.04 (s, 6H), 1.84 (s, 3H), 1.74 (br s, 4H) ppm.

EXAMPLE 290

N-[3,6-Dimethyl-2-(2,4,6-trimethyl-phenoxy)-pyridin-4-yl]-N-(2-pyrrolidin-1-yl-ethyl-isobutyramide 1H NMR(CDCl$_3$) d 6.89 (s, 2H), 6.56 (s, 1H), 4.09–4.17 (m, 1H), 3.38–3.48 (m, 1H), 2.65–2.77 (m, 2H), 2.61 (br s, 4H), 2.33–2.40 (m, 1H), 2.30 (s, 3H), 2.24 (s, 3H), 2.20 (s, 3H), 2.05 (s, 6H), 1.77 (br s, 4H), 1.04 (t, 6H, J=7 Hz) ppm.

EXAMPLE 291

N-[3,6-Dimethyl-2-(2,4,6-trimethyl-phenoxy)-pyridin-4-yl]-N-(2-pyrrolidin-1-yl-ethyl)-malonamic acid ethyl ester 1H NMR(CDCl$_3$) d 6.89 (s, 2H), 6.63 (s, 1H), 4.11–4.17 (m, 3H), 3.44–3.56 (m, 1H), 3.15 (s, 2H), 2.72 (br s, 2H), 2.57 (br s, 4H), 2.30 (s, 3H), 2.24 (s, 3H), 2.23 (s, 3H), 2.04 (s, 6H), 1.77 (br s, 4H), 1.24 (t, 3H, J=7 Hz)

EXAMPLE 292

2-(4-Chloro-2,6-dimethyl-phenoxy)-4-cyclopentylamino-6-methyl-pyridine-3-carbaldehyde 1H NMR(CDCl$_3$) d 9.42(d,1H), 7.05(s,2H), 6.09(s,1H), 4.18(brs,1H), 4.06(m,2H), 3.95(m,1H), 3.77(m,1H), 2.35 (m,1H), 2.17(s,3H), 2.09(s,6H), 1.98(m,1H) ppm.

EXAMPLE 293

4-(1-Ethyl-propylamino)-2-(4-methoxy-2,6-dimethyl-phenoxy)-6-methyl-pyridine-3-carbaldehyde 1HNMR(CDCl$_3$) 9.26(d, 1H), 6.60(s, 2H), 6.10(s, 1H), 3.78(s, 3H), 3.40(m, 1H), 2.14(s, 3H), 2.11 (s, 6H), 1.66(m, 4H), 0.96(t, 6H)ppm

EXAMPLE 294

1-[2-(4-Chloro-2-methoxy-phenoxy)-4-(1-ethyl-propylamino)-6-methyl-pyridin-3-yl]-ethanone 1H NMR(CDCl$_3$) d 9.59 (br d, 1H), 6.93–7.02 (m, 3H), 6.14 (s, 1H), 3.78 (s, 3H), 3.33–3.38 (m, 1H), 2.69 (s, 3H), 2.14 (s, 3H), 1.49–1.67 (m, 4H), 0.94 (t, 6H, J=7 Hz) ppm.

The following Examples 295–329 relate to other compounds of formula I of the invention, wherein R$_4$ is methyl:

EXAMPLE 295 sec-Butyl-[2-(2,6-dimethyl-4-trifluoromethoxy-phenoxy)-3,6-dimethyl-pyridin-4-yl]-amine 1H NMR(CDCl$_3$) d 6.90 (s, 2H), 6.09 (s, 1H), 3.78 (d, 1H, J=8Hz), 3.45–3.52 (m, 1H), 2.15 (s, 3H), 2.10 (s, 9H), 1.51–1.67 (m, 2H), 1.23 (d, 3H, J=8Hz), 0.98 (t, 3H, J=7 Hz) ppm.

EXAMPLE 296

[2-(2,6-Dimethyl-4-trifluoromethoxy-phenoxy)-3,6-dimethyl-pyridin-4-yl]-(1-ethyl-propyl)-amine 1H NMR(CDCl$_3$) d 6.91 (s, 2H), 6.08 (s, 1H), 3.74 (d, 1H, J=8Hz), 3.31–3.34 (m, 1H), 2.15 (s, 3H), 2.11 (s, 6H), 2.08 (s, 3H), 1.49–1.68 (m, 4H), 0.96 (t, 6H, J=8 Hz) ppm.

EXAMPLE 297

[3,6-Dimethyl-2-(2,4,6-trimethyl-phenoxy)-pyridin-4-yl]-(2-pyrrolidin-1-yl-ethyl)-(2,2,2-trifluoro-ethyl)-amine 1H NMR(CDCl$_3$) d 6.87 (s, 2H), 6.55 (s, 1H), 3.78 (q, 2H, J=9 Hz), 3.60–3.72 (m, 2H), 2.82–2.98 (m, 6H), 2.29 (s, 3H), 2.26 (s, 3H), 2.20 (s, 3H), 2.03 (s, 6H), 1.96 (br s, 4H) ppm.

The following compounds (Examples 298 and 299) were prepared starting with an appropriate 2-(substituted-phenoxy)-4-(1-methanesulfonyloxymethyl-propylamino)-3,6-substituted-pyridine with an appropriate amine:

EXAMPLE 298

N2-[2-(4-Chloro-2,6-dimethyl-phenoxy)-3,6-dimethyl-pyridin-4-yl]-N1-cyclopropylmethyl-butane-1,2-diamine 1H NMR(CDCl$_3$) d 7.01(s, 2H), 6.17(s, 1H), 4.40(d, 1H), 3.82(m, 1H), 3.05(m, 2H), 2.69(m, 2H), 2.20(s, 3H), 2.12(s, 3H), 2.04(s, 6H),1.70(m, 2H), 0.98(t, 3H), 0.96(m, 4H) ppm

EXAMPLE 299

N-[3,6-Dimethyl-2-(2,4,6-trimethyl-phenoxy)-pyridin-4-yl]-N-ethyl-N',N'-dimethyl-ethane-1,2-diamine 1H NMR(CDCl$_3$) d 6.86(s, 2H), 6.43 (s, 1H), 3.26 (AB quartet, 2H), 3.12 (q, 2H, J=7 Hz), 2.51 (AB quartet, 2H), 2.34 (s, 6H), 2.29 (s, 3H), 2.23 (s, 3H), 2.18 (s, 3H), 2.05 (s, 6H), 1.09 (t, 3H, J=7 Hz) ppm.

EXAMPLE 300

N-2-[3,6-Dimethyl-2-(2,4,6-trimethyl-phenoxy)-pyridin-4-yl]-N-1-methyl-butane-1,2-diamine 1HNMR(CDCl$_3$) 6.85(s, 2H), 6.12(s, 1H), 4012(d, 1H), 3.56(m, 1H), 2.79(m, 2H), 2.47(s, 3H), 2.28(s, 3H), 2.14(d, 6H), 2.06(s, 6H), 1.62(m, 2H), 0.97(t, 3H)ppm

EXAMPLE 301

N-2-[3,6-Dimethyl-2-(2,4,6-trimethyl-phenoxy)-pyridin-4-yl]-N-1-ethyl-butane-1,2-diamine 1H NMR(CDCl$_3$) d 7.80(s, 1H), 6.85 (s, 2H), 6.12(s, 1H), 4.22(d, 1H), 3.57(m, 1H), 2.82(m, 2H), 2.72(q, 2H), 2.28(s, 3H), 2.13(s, 6H), 2.06(s, 6H), 1.63(m, 2H), 1.16(t, 3H), 0.97(t, 3H)ppm

EXAMPLE 302

N2-[3,6-Dimethyl-2-(2,4,6-trimethyl-phenoxy)-pyridin-4-yl]-N1-ethyl-N1-methyl-butane-1,2-diamine 1H NMR (CDCl$_3$) d 6.85(s ,2H), 6.06(s, 1H), 4.58(m, 1H), 3.39(m, 1H), 2.49(m, 4H), 2.28(s, 6H), 2.14(s, 6H), 2.06(s, 6H), 1.66(m, 2H), 1.08(m, 3H), 0.96(t, 3H)ppm

EXAMPLE 303

N-1-Butyl-N-2-[3,6-dimethyl-2-(2,4,6-trimethyl-phenoxy)-pyridin-4-yl]-butane-1,2-diamine 1H NMR(CDCl$_3$) d 6.85(s, 2H), 6.11(s, 1H), 4.21(d, 1H), 3.51(q, 1H), 2.79(m, 2H),2.65(t, 2H), 2.28(s, 3H), 2.14(s, 6H), 2.06(s, 6H),1.62(m, 2H), 1.49(m, 2H), 1.35(m, 2H), 0.97(t, 3H), 0.91 (t, 3H)ppm

EXAMPLE 304

N-1-Cyclopropylmethyl-N-2-[3,6-dimethyl-2-(2,4,6-trimethyl-phenoxy)-pyridin-4-yl]-N1-propyl-butane-1,2-diamine 1H NMR (CDCl$_3$) d 6.85(s, 2H), 6.06(s, 1H), 4.65(m, 1H), 3.32(m 1H), 2.61(m, 4H), 2.28(s, 3H), 2.14(s,3H), 2.12(s, 2H), 2.06(s, 6H), 1.71(m, 2H), 1.46(m, 2H), 0.96(t, 3H), 0.87(t, 3H)ppm

EXAMPLE 305

N-2-[3,6-Dimethyl-2-(2,4,6-trimethyl-phenoxy)-pyridin-4-yl]-N-1-propyl-butane-1,2-diamine 1H NMR(CDCl$_3$) d 6.85(s, 2H), 6.11(s, 1H), 4.21(d, 1H), 3051(q, 1H), 2.79(m, 2H), 2.62(m, 2H), 2.28(s, 3H), 2.13(s, 6H), 2.06(s, 6H), 1.62(m, 2H), 1.54(m,2H), 0.97(t, 3H), 0.91(t, 3H)ppm

EXAMPLE 306

N-2-[3,6-Dimethyl-2-(2,4,6-trimethyl-phenoxy)-pyridin-4-yl]-N-1-(2-methoxy-ethyl)-butane-1,2-diamine 1H NMR (CDCl$_3$) d 6.85(s, 2H), 6.11(s, 1H), 4.18(d, 1H), 3.51(m, 3H),. 3.35(s, 2H), 2.82(m, 4H), 2.28(s, 3H), 2.14(s, 6H), 2.06(s, 6H), 1.62(m, 2H), 0.97(t, 3H)ppm

EXAMPLE 307

N-2-[3,6-Dimethyl-2-(2,4,6-trimethyl-phenoxy)-pyridin-4-yl]-N-1-furan-2-ylmethyl-butane-1,2-diamine 1HNMR(CDCl$_3$) 7.36(s, 1H), 6.85(s, 2H), 6.32(d, 1H), 6.24(d, 1H), 6.09(s, 1H), 4.15(d, 1H), 3.84(d, 2H), 3.58(m 1H), 2.79(m, 2H), 2.28(s, 3H), 2.13(d, 6H), 2.05(s, 6H), 1.62(m, 2H), 0.95(t, 3H)ppm

EXAMPLE 308

N-1-Cyclopropylmethyl-N-2-[3,6-dimethyl-2-(2,4,6-trimethyl-phenoxy)-pyridin-4-yl]-butane-1,2-diamine 1HNMR(CDCl$_3$) 6.85(s, 2H), 6.14(s, 1H), 4.39(m, 1H), 3.70(m, 1H), 3.01(m, 2H), 2.67(d, 2H), 2.28(s, 3H), 2.20(s, 3H), 2.14(s, 3H), 2.05(s, 6H), 1.71(m, 2H), 0.98(t. 3H), 0.55(d, 2H), 0.21(d, 2H)ppm.

EXAMPLE 309

[3,6-Dimethyl-2-(2,4,6-trimethyl-phenoxy)-pyridin-4-yl]-(1-thiazolidin-3-ylmethyl-propyl)-amine 1HNMR(CDCl$_3$) 6.85(s, 2H), 6.07(s, 1H), 4.21(d, 1H), 4.06(d, 2H), 3.41(m, 1H), 3.07(m, 2H), 2.89(m, 2H), 2.52 (m, 2H), 2.28(s, 3H), 2.15(d, 6H), 2.06(s, 6H), 1.75(m, 1H), 1.66(m, 1H0, 0.98(t, 3H)ppm

EXAMPLE 310

N-2-[3,6-Dimethyl-2-(2,4,6-trimethyl-phenoxy)-pyridin-4-yl]-butane-1,2-diamine

To a solution of (1-hydroxymethyl-propyl)-[3,6-dimethyl-2-(2,4,6-trimethyl-phenoxy)-pyridin-4-yl]-amine in toluene was added diphenylphosphoryl azide and 1,8-diazbicyclo[3,4,0]undec-7-ene at 0° C. The resulting mixture was stirred at rt for 30 min, then heated 75° C. overnight. The reaction mixture was quenched with water and extracted with methylene chloride. The organic layer was separated, dried, concentrated and purified by silica gel Biotage using 1:1 methylene chloride/hexane to methylene chloride as eluent to give (1-azidomethyl-propyl)-[3,6-dimethyl-2-(2,4,6-trimethyl-phenoxy)-pyrid in-4-yl]-amine as a light yellow oil. The oil was reduced with triphenylphospine to give the title compound. 1H NMR (CDCl$_3$) d 6.86(s, 2H), 6.11(s, 1H), 4.02(d, 1H), 3.40(q, 1H), 2.84(m, 2H), 2.28(s, 3H), 2.13(s, 6H), 2.06(s, 6H), 1.61 (m, 2H), 0.98(t, 3H)ppm

EXAMPLE 311

1-{2-[3,6-Dimethyl-2-(2,4,6-trimethyl-phenoxy)-pyrid in-4-ylamino]-butyl}-3-ethyl-urea A mixture of N-2-[3,6-dimethyl-2-(2,4,6-trimethyl-phenoxy)-pyridin-4-yl]-butane-1,2-diamine and ethyl isocyanate in dichloroethane was stirred at rt overnight. Standard work-up, and purification yielded the title compound. APCl [M+1]=399.3, 1H NMR(CDCl$_3$).

EXAMPLE 312

N-{2-[3,6-Dimethyl-2-(2,4,6-trimethyl-phenoxy)-pyridin-4-ylamino]-butyl}-methanesulfonamide A mixture of N-2-[3,6-Dimethyl-2-(2,4,6-trimethyl-phenoxy)-pyridin-4-yl]-butane-1,2-diamine and methanesulfonyl chloride in dichloroethane was stirred at rt overnight. Standard work-up and purification yielded the title compound. APCl [M+1]=406.2, 1H NMR(CDCl$_3$)

EXAMPLE 313

N-{2-[3,6-Dimethyl-2-(2,4,6-trimethyl-phenoxy)-pyridin-4-ylamino]-butyl}-acetamide A mixture of N-2-[3,6-dimethyl-2-(2,4,6-trimethyl-phenoxy)-pyridin-4-yl]-butane-1,2-diamine and acetyl chloride in dichloroethane was stirred at rt overnight. Standard work-up and purification yielded the title compound. APCl [M+1]=370.3, 1H NMR(CDCl$_3$)

EXAMPLE 314

Cyclopropylmethyl-[3,6-dimethyl-2-(2,4,6-trimethyl-phenoxy)-pyridin-4-yl]-propyl-amine 1H NMR(CDCl$_3$) d 6.85 (s, 2H), 6.44 (s, 1H), 3.13 (AB q, 2H), 2.90 (d, 2H, J=8 Hz), 2.28 (s, 3H), 2.24 (s, 3H), 2.16 (s, 3H), 2.05 (s, 6H), 1.47–1.65 (m, 2H), 0.86–0.92 (m, 4H), 0.42–0.46 (m, 2H), 0.04–0.08 (m, 2H)

APCl+m/z=353.3 (M+1)

EXAMPLE 315

Cyclopropylmethyl-[3,6-dimethyl-2-(2,4,6-trimethyl-phenoxy)-pyridin-4-yl]-propyl-amine 1H NMR(CDCl$_3$) d 6.85 (s, 2H), 6.44 (s, 1H), 3.13 (AB q, 2H), 2.90 (d, 2H, J=8 Hz), 2.28 (s, 3H), 2.24 (s, 3H), 2.16 (s, 3H), 2.05 (s, 6H), 1.47–1.65 (m, 2H), 0.86–0.92 (m, 4H), 0.42–0.46 (m, 2H), 0.04–0.08 (m, 2H)

APCl+m/z=353.3 (M+1)

EXAMPLE 316

3,6-Dimethyl-4-(2-methyl-aziridin-1-yl)-2-(2,4,6-trimethyl-phenoxy)-pyridine

1H NMR(CDCl$_3$) d 6.86 (s, 2H), 6.29 (s, 1H), 2.31 (sa, 3H), 2.29 (s, 3H), 2.19 (m, 1H), 2.15 (s, 3H), 2.10 (m, 2H), 2.04 (s, 6H), 1.44 (d, 3H, J=5 Hz)

EXAMPLE 317

4-(2-Methoxymethyl-pyrrolidin-1-yl)-3,6-dimethyl-2-(2,4,6-trimethyl-phenoxy)-pyridine 1H NMR(CDCl$_3$) d 6.86 (s, 2H), 6.34 (s, 1H), 3.99 (q, 1H, J=4 Hz), 3.67 (m, 1H), 3.49 (dd, 1H, J=9 Hz, 4 Hz), 3.32 (s, 3H), 3.15 (m, 2H)2.29 (s, 3H), 2.24 (s, 3H), 2.16 (s, 3H), 2.06 (s, 6H), 1.78–1.97 (m, 4H) ppm.

EXAMPLE 318

[2-(4-Chloro-2,6-dimethyl-phenoxy)-3,6-dimethyl-pyridin-4-yl]-(tetrahydro-furan-3-yl)-amine 1H NMR(CDCl$_3$) d 7.04(s,2H), 6.11(s,1H), 4.27(brs,1H), 3.7–4.1(m,4H), 2.2–2.4(m,1H0, 2.08(s,6H), 2.07(s,6H),1.94 (m,1H) ppm.

EXAMPLE 319

[1-(tert-Butyl-dimethyl-silanyloxymethyl)-propyl]-[3,6-dimethyl-2-(2,4,6-trimethyl-phenoxy)-pyridin-4-yl]-amine 1H NMR(CDCl$_3$) d 6.85(s, 2H), 6.07(s, 1H), 3.71(m, 2H), 3.39(m, 1H), 2.28(s, 3H), 2.16(s, 3H), 2.09(s, 3H), 2.06(s, 6H), 1.70(m, 2H), 0.91(s 9H)ppm

EXAMPLE 320

[3,6-Dimethyl-2-(2,4,6-trimethyl-phenoxy)-pyridin-4-yl]-ethyl-(2-pyrrolidin-1-yl-ethyl)-amine 1H NMR(CDCl$_3$) d 6.86 (s, 2H), 6.44 (s, 1H), 3.25–3.30 (m, 2H), 3.12 (q, 2H, J=7 Hz), 2.56–2.66 (m, 6H), 2.29 (s, 3H), 2.23 (s, 3H), 2.17 (s, 3H), 2.05 (s, 6H), 1.80 (br s, 4H), 1.09 (t, 3H, J=7 Hz)

13C NMR(CDCl$_3$) d.

APCl+m/z=382(M+1)

EXAMPLE 321

4-[4-(1-Ethyl-propoxy)-3,6-dimethyl-pyridin-2-yloxy]-3,5-dimethyl-benzoic acid

To a −78° C. solution of intermediate in dry THF was added n-BuLi. After stirring at that temperature for 10 min, CO$_2$(g) was bubbled into the reaction mixture. The resulting mixture was stirred at −78° C. for 2 hr, gradually warmed to rt. The mixture was quenched with dilute HCl and extracted with methylene chloride. The organic layer was separated, dried, concentrated, and purified to give the title compound as a white solid, mp. 168.4° C. 1H NMR(CDCl$_3$) 7.58(s,2H), 6.36(s,1H), 4.24(m,1H), 2.35(s,3H), 2.22(s,3H), 2.14(s,6H), 1.75(m,4H), 0.99(t,6H) ppm.

The following Examples 322–326 were prepared according to the following general procedure: To a solution of 4-[4-(1-ethyl-propoxy)-3,6-dimethyl-pyridin-2-yloxy]-3,5-dimethyl-benzoic acid in anhydrous methylene chloride was added SOCl$_2$ and stirred at rt. for 1 hr. the mixture was concentrated to dryness to provide the corresponding acyl chloride. The acyl chloride was quenched with an appropriate nucleophile (e.g., NH$_3$, MeNH$_2$, Me$_2$NH, EtNH$_2$, or methanol) and stirred at rt to provide the title compounds:

EXAMPLE 322

4-[4-(1-Ethyl-propoxy)-3,6-dimethyl-pyridin-2-yloxy]-3,5-dimethyl-benzamide

1H NMR(CDCl$_3$) d 7.51(s,2H), 6.32(s,1H), 6.2(brs,1H), 5.7(brs,1H), 4.20(m,1H), 2.22(s,3H), 2.19(s,3H), 2.12(s, 6H), 1.72(m,4H), 0.97(t,6H) ppm.

EXAMPLE 323

4-[4-(1-Ethyl-propoxy)-3,6-dimethyl-pyridin-2-yloxy]-3,5,N-trimethyl-benzamide

1H NMR(CDCl$_3$) d 7.43(s,2H), 6.30(s,1H), 6.19(brs,1H), 4.19(m,1H), 2.95(d,3H), 2.19(s,3H), 2.18(s,3H), 2.10(s,6H), 1.71(m,4H), 0.97(t,6H) ppm.

EXAMPLE 324

4-[4-(1-Ethyl-propoxy)-3,6-dimethyl-pyridin-2-yloxy]-3,5,N,N-tetramethyl-benzamide 1H NMR(CDCl$_3$) d 7.12(s,2H), 6.30(s,1H), 4.18(m,1H), 3.09(s,3H), 3.05(s,3H), 2.18(s,6H), 2.10(s,6H), 1.71(m,4H), 0.97(t,6H) ppm.

EXAMPLE 325

N-Ethyl-4-[4-(1-ethyl-propoxy)-3,6-dimethyl-pyridin-2-yloxy]-3,5-dimethyl-benzamide 1H NMR(CDCl$_3$) d 7.46(s,2H), 6.30(s,1H), 6.1(brs,1H), 4.19(m,1H), 3.48(m,2H), 2.18(s,6H), 2.12(s,6H), 1.72(m, 4H), 1.25(t,3H), 0.97(t,6H) ppm.

EXAMPLE 326

4-[4-(1-Ethyl-propoxy)-3,6-dimethyl-pyridin-2-yloxy]-3,5-dimethyl-benzoic acid methyl ester 1H NMR(CDCl$_3$) d 7.76(s,2H), 6.30(s,1H), 4.17(m,1H), 3.89(s,3H), 2.19(s,3H), 2.169(s,3H), 2.12(s,6H), 1.712(m, 4H), 0.97(t,6H) ppm.

The following Examples 327–329 were prepared by the following general procedure: To a solution of 4-[4-(1-Ethyl-propylamino)-3,6-dimethyl-pyridin-2-yloxy]-3,5-dimethyl-benzoic acid in anhydrous methylene chloride was added SOCl$_2$ and stirred at rt for 1 hr. the mixture was concentrated to dryness to provide the corresponding acyl chloride. The acyl chloride was quenched with an appropriate nucleophile (e.g., NH$_3$, MeNH$_2$, or methanol) and stirred at rt to provide the title compounds:

EXAMPLE 327

4-[4-(1-Ethyl-propylamino)-3,6-dimethyl-pyridin-2-yloxy]-3,5-dimethyl-benzamide

1H NMR(CDCl$_3$) d 7.51(s,2H), 6.2(brs,1H), 6.1(s,1H), 5.5(brs,1H), 3.9(d,1H), 3.3(m,1H), 2.19(s,3H), 2.14(s,6H), 2.12(s,3H), 1,7(m,2H), 1.5(m,2H), 0.96(t,6H) ppm.

EXAMPLE 328

4-[4-(1-Ethyl-propylamino)-3,6-dimethyl-pyridin-2-yloxy]-3,5,N-trimethyl-benzamide 1H NMR(CDCl$_3$) d 7.431(s,2H), 6.3(ds,1H), 6.091(s,1H), 3.8(d,1H), 3.35(m,1H), 2.96(d,3H), 2.16 (s,3H), 2.12(s,9H), 1.65(m,2H), 1.53(m,2H), 0.95(t,6H) ppm.

EXAMPLE 329

4-[4-(1-Ethyl-propylamino)-3,6-dimethyl-pyridin-2-yloxy]-3,5-dimethyl-benzoic acid methyl ester 1H NMR(CDCl$_3$) d 7.751(s,2H), 6.08(s,1H), 3.89(s,3H), 3.80(d,1H), 3.34(m,1H), 2.13(s,6H), 2.11(s,6H), 1.66(m, 2H), 1.54(m,2H), 0.95(t,6H) ppm.

The following Examples 330–340 relate to other compounds of formula I of the invention, wherein R$_4$ is —CN:

EXAMPLE 330

2-(4-Chloro-2,6-dimethyl-phenoxy)-6-methyl-4-(tetrahydro-furan-3-ylamino)-nicotinonitrile APCl [M+1]358.3

EXAMPLE 331

4-(1-Ethyl-propylamino)-2-(4-methoxy-2,6-dimethyl-phenoxy)-6-methyl-nicotinonitrile Cala: C, 71.36; H, 7.70; N, 11.89; found: C, 71.16; H, 8.09; N, 11.47. HNMR(CDCl:$_3$) 6.59(s, 2H), 6.08(s, 1H), 4.74(d, 1H), 3.78(s, 3H), 3.38(m, 1H), 2.18(s, 3H), 2.10(s, 6H), 1.64(m, 2H), 1.55(m, 2H), 0.96(t, 6H)ppm.

EXAMPLE 332

4-(1-Ethyl-propylamino)-6-methyl-2-(2,4,6-trimethyl-pyridin-3-yloxy)-nicotinonitrile The title compound was prepared by heating 2-chloro-4-(1-ethyl-propylamino)-6-methyl-nicotinonitrile with 2,4,6-trimethyl-3-hydroxy-pyridine in NMP.

1HNMR(CDCl$_3$) 7.02(m,1H), 6.13(s, 1H), 4.81(d, 1H), 3.40(m, 1H0, 2.67(s, 3H0, 2.48(s, 3H0, 2.25(s, 3H), 2.16(s, 3H), 1.68(m, 4H), 0.97(t, 6H)ppm

EXAMPLE 333

2-(4-Methoxy-2,6-dimethyl-phenoxy)-4-(1-methoxymethyl-propylamino)-6-methyl-nicotinonitrile 1HNMR(CDCl$_3$) 6.59(s, 2H), 6.11(s, 1H), 5.08(d, 1H), 3.78(s, 3H), 3.56(m, 1H), 3.47(m, 1H), 3.38(s, 3H), 2.19(s, 3H), 2.10(s, 6H), 1.61(m, 2H), 0.99(t, 3H) ppm

EXAMPLE 334

2-(4-Bromo-2,6-dimethyl-phenoxy)-4-(1-ethyl-propylamino)-6-methyl-nicotinonitrile 1H NMR(CDCl$_3$) d 7.19(s,2H), 6.09(s,1H), 4.77(d,1H), 3.39(m,1H), 2.18(s,3H), 2.10(s,6H), 1.65(m,2H), 1.55(m, 2H), 0.96(t,3H) ppm.

EXAMPLE 335

4-[3-Cyano-4-(1-ethyl-propylamino)-6-methyl-pyridin-2-yloxy]-3-methoxy-benzoic acid methyl ester APCl [M+1]384.2, 1H NMR(CDCl$_3$)

EXAMPLE 336

4-[3-Cyano-4-(1-ethyl-propylamino)-6-methyl-pyridin-2-yloxy]-3-methoxy-benzamide 1H NMR(CDCl$_3$) d 7.52(s,1H), 7.32(d,1H), 7.16(d,1H), 6.25(brs,1H), 6.12(s,1H), 5.8(brs,1H), 4.78(d,1H), 3.80(s, 3H), 3.39(m,1H), 2.20(s,3H), 1.67(m,2H), 1.55(m,2H), 0.95 (t,3H) ppm.

EXAMPLE 337

2-(4-Chloro-2,6-dimethyl-phenoxy)-4-(1-methoxymethyl-propylamino)-6-methyl-nicotinonitrile 1H NMR(CDCl$_3$) d 7.03(s,2H), 6.12(s,1H), 5.08(d,1H), 3.47(m,1H), 3.43(m,2H), 3.38(s,3H), 2.18(s,3H), 2.09(s, 6H), 1.76(m,2H), 1.61 (m,2H), 0.99(t,6H) ppm.

EXAMPLE 338

2-(4-Chloro-2,6-dimethyl-phenoxy)-4-[(1-methoxymethyl-propyl)-methyl-amino]-6-methyl-nicotinonitrile 1H NMR(CDCl$_3$) d 7.03(s,2H), 6.27(s,1H), 4.33(m,1H), 3.59(m,1H), 3.52(m,1H), 3.35(s,3H), 3.06(s,3H), 2.16(s, 3H), 2.11 (s,6H), 1.69(m,4H), 0.97(t,6H) ppm.

EXAMPLE 339

2-(4-Chloro-2-methoxy-phenoxy)-4-(1-ethyl-propylamino)-6-methyl-nicotinonitrile

1H NMR(CDCl$_3$) d 7.04 (d, 1H, J=9 Hz), 6.91–6.94 (m, 2H), 6.10 (s, 1H), 4.73 (d, 1H, J=9 Hz), 3.75 (s, 3H), 3.35–3.38 (m, 1H), 2.19 (s, 3H), 1.47–1.70 (m, 4H), 0.95 (t, 6H, J=8 Hz) APCl+m/z=360.1 (M+1), 362.1 (M+3)

EXAMPLE 340

2-(4-Bromo-2-methoxy-phenoxy)-4-(1-ethyl-propylamino)-6-methyl-nicotinonitrile

1H NMR(CDCl$_3$) d 7.06–7.09 (m, 2H), 6.98–7.00 (m, 1H), 6.10 (s, 1H), 4.73 (br d, 1H), 3.75 (s, 3H), 3.35–3.42 (m, 1H), 2.21 (s, 3H), 1.43–1.72 (m, 4H), 0.95(t, 6H, J=7 Hz) ppm.

Other examples of compounds of the invention are as follows:

EXAMPLE 341

[2-(4-Chloro-2,6-dimethyl-phenoxy)-6-methyl-pyridin-4-yl]-(1-methoxymethyl-propyl)-amine 1H NMR(CDCl$_3$) d 7.05 (s, 2H), 6.04 (s, 1H), 5.33 (s, 1H), 4.26 (br d, 1H), 3.34–3.39 (m, 1H), 3.31 (s, 6H), 2.31 (s, 3H), 2.12 (s, 6H), 1.47–1.61 (m, 4H), 0.89 (t, 6H, J=8 Hz) ppm.

EXAMPLE 342

[2-(4-Chloro-2,6-dimethyl-phenoxy)-6-methyl-3-methylaminomethyl-pyridin-4-yl]-(tetrahydro-furan-3-yl)-amine 1H NMR(CDCl$_3$) d 7.03(s,2H), 6.08(s,1H), 4.18(s,2H), 3.8–4.2(m,5H), 2.57(s,3H), 2.2–2.4(m,2H), 2.15(s,3H), 2.04 (s,6H) ppm.

EXAMPLE 343

[2-(4-Chloro-2,6-dimethyl-phenoxy)-6-methyl-4-(tetrahydro-furan-3-ylamino)-pyridin-3-yl]-methanol 1H NMR(CDCl$_3$) d 7.02(s,2H), 6.10(s,1H), 5.49(brs,1H), 4.89(t,2H), 4.12(brs,1H), 4.01(m,2H), 3.99(m,1H), 3.75(m, 1H), 2.30(m,1H), 2.16(s,3H), 2.05(s,6H), 1.95(m,1H) ppm.

EXAMPLE 344

2-[2-(4-Chloro-2,6-dimethyl-phenoxy)-6-methyl-pyridin-4-ylamino]-4-methylsulfanyl-butan-1-ol 1H NMR(CDCl$_3$) d 7.06(s,2H), 6.29(s,1H), 5.47(s,1H), 3.6–3.8(m,2H), 3.5(m,1H), 2.38(s,3H), 2.11(s,6H), 2.03(s, 3H), 1.87(m,1H), 1.69(m,1H) ppm.

Preparation A (6-Chloro-2-methyl-5-nitro-pyrimidin-4-yl)-(2,4,6-trimethyl-pyridin-3-yl)-amine A solution of 2-methyl-5-nitro-4,6-dichloro-pyrimidine (208 mg, 1.00 mmol) in 2.5 ml of acetonitrile was treated with 2,4,6-trimethyl-3-amino-pyridine (273 mg, 2 mmol) stirred at room temperature 2 hours. The mixture was quenched with water and extracted with ethyl acetate. The organic layer was washed with brine, dried and concentrated to give red residue. The residue was purified through silica gel column chromatography using chloroform to 6% methanol in chloroform as eluent to give the title compound (110 mg, 36%) as an orange oil. $^1$H NMR (CDCl$_3$) δ 8.78 (brs, 1H), 6.97 (s, 1H), 2.54 (s, 3H), 2.43 (s, 3H), 2.40 (s, 3H), 2.17 (s, 3H) ppm.

Preparation B

2-Chloro-4-(1-ethyl-propylamino)-6-methyl-nicotinic acid

The title compound was prepared by reaction of 2-chloro-4-(1-ethyl-propylamino)-6-methyl-nicotinic acid methyl ester with LiOH.H$_2$O in a mixture of water and dioxane at room temperature. The desired product was acidified to pH 3 and extracted with ethyl acetate. The organic layer was dried and concentrated to dryness. The title compound was obtained as white crystals after titration with ethyl acetate. mp. 164–165° C.; anal. For C$_{12}$H$_{17}$Cl$_2$O$_2$ cacl. C, 56.14; H, 6.67; N, 10.91; found: C, 56.40; H, 6.53; H, 10.93.

Preparation C

4-Chloro-6-ethyl-3-methyl-2-(2,4,6-trimethyl-phenoxy)-pyridine 1-oxide

To a solution of 2,4,6-trimethylphenol in dry THF was added NaH and stirred at room temperature for 20 minutes. A solution of 2,4-dichloro-6-ethyl-3-methyl-pyridine 1-oxide was added and the resulting mixture was heated at reflux for 1.5 hour. The mixture was cooled to room temperature, quenched with water, extracted with ethyl acetate. The organic layer was separated, dried and concentrated to give the title compound which was used directly for the next step reaction.

Preparation D

4-Chloro-6-ethyl-3-methyl-2-(2,4,6-trimethyl-phenoxy)-pyridine

To a solution of 4-Chloro-6-ethyl-3-methyl-2-(2,4,6-trimethyl-phenoxy)-pyridine 1-oxide in methylene chloride was added PCl$_3$ and the resulting mixture was heated at reflux for 20 min, cooled to rt. The mixture was concentrated to dryness. The residue was worked-up using standard procedure to give the title compound. After silica gel purification, the titel compound was prepared as a white solid, mp. 42–44° C. Anal. For C$_{17}$H$_{20}$ClNO calc. C, 70.46; H, 6.96; N, 4.83; found, C, 70.35; H, 7.13; N, 4.58.

Preparation E

2-[4-Chloro-6-methyl-2-(2,4,6-trimethyl-phenoxy)-pyridin-3-ylmethyl]-malonic acid dimethyl ester The title compound was prepared by reacting 4-chloro-3-chloromethyl-6-methyl-2-(2,4,6-trimethyl-phenoxy)-pyridine with dimethyl malonate/NaH in methanol. The title compound was isolated as a colorless oil.

Preparation F

4-Chloro-3,6-dimethyl-2-(2,4,6-trimethyl-3-pyridyl)-pyridine

Preparation G

2-Chloro-4-(1-methoxymethyl-propoxy)-6-methyl-nicotinic acid ethyl ester

1H NMR(CDCl$_3$) d 6.72(s,1H), 4.5(m,1H), 4.4(q,2H), 3.49(d,2H), 3.31(s,3H), 2.46(s,3H), 1.68(m,2H), 1.34(t,3H), 0.93(t,3H) ppm.

Preparation H

2-Chloro-4-(1-methoxymethyl-propoxy)-6-methyl-nicotinic acid

1H NMR(CDCl$_3$) d 6.81(s,2H), 4.51(m,1H), 3.60(m,2H), 3.40(s,3H), 2.55(s,3H), 1.77(m,2H), 1.02(t,3H)ppm.

Preparation I (2-Chloro-6-methyl-3-nitro-pyridin-4-yl)-(1-methoxymethyl-propyl)-amine mp. 63–65° C., Anal. For C$_{11}$H16N3O3Cl calc. C, 48.27; H, 5.89, N, 15.35; found C, 48.65; H, 6.03, N, 15.11.

Preparation J (5-Bromo-6-chloro-2-methyl-pyrimidin-4-yl)-(2,4-dichloro-phenyl)-amine Mp. 165–167° C.; Anal. For C11H7BrCl3 calc.: C, 35.95; H, 1.92; N, 11.43; found: C, 36.41; H, 1.91; N, 11.05.

Preparation K (6-Chloro-2-methyl-pyrimidin-4-yl)-(2,4-dichloro-phenyl)-amine Mp. 134–136° C.; Anal. For C$_{11}$H$_8$Cl$_3$N$_3$ calc.: C, 45.79; H, 2.79; N, 14.56; found: C, 45.91; H, 2.69; N, 14.50.

Preparation L

[4-Chloro-6-(1-ethyl-propylamino)-2-methyl-pyrimidin-5-yl]-acetic acid ethyl ester Mp. 78–80° C., anal. For C$_{14}$H$_{22}$ClN$_3$O$_2$ calc.: C, 56.09; H, 7.40; N, 14.02; found: C, 56.31; H, 7.60; N,13.94.

Preparation M

2-[4-Bromo-2-methyl-6-(2,4,6-trimethyl-phenoxy)-pyrimidin-5-yl]-propionic acid ethyl ester 1H NMR(CDCl$_3$) d 6.86(s,2H), 4.2–4.359m,2H), 4.0–4.15(m,1H), 2.4(s,3H), 2.28(s,3H), 1.99(s,3H), 1.97(s,3H), 1.58(d,3H), 1.22(t,3H) ppm.

Preparation N 2-(4,6-Dibromo-2-methyl-pyrimidin-5-yl)-propionic acid ethyl ester 1H NMR(CDCL$_3$) 4.36(m,1H), 4.19(m,2H), 2.68(s,3H), 1.549d,3H), 1.22(t,3H) ppm.

Preparation O

4-Bromo-3-methoxy-6-methyl-2-(2,4,6-trimethyl-phenoxy)-pyridine

1H NMR(CDCl$_3$) d 6.92(s,1H), 6.87(s,2H), 4.00(s,3H), 2.299s,3H), 2.18(s,3H), 2.059s,6H) ppm.

Preparation P

4-Bromo-2-(4-chloro-2,6-dimethyl-phenoxy)-3,6-dimethyl-pyridine

1H NMR(CDCl$_3$) d 7.04(s,2H), 6.97(s,1H), 2.42(s,3H), 2.17(s,3H), 2.03(s,6H) ppm.

Preparation Q

4-Bromo-2-(2,4-dichloro-6-methyl-phenoxy)-3-methoxy-6-methyl-pyridine

1H NMR(CDCl$_3$) d 7.3(d,1H), 7.18(d,1H), 4.0(s,3H), 2.2(s,3H), 2.15(s,3H) ppm.

Preparation R

4-Bromo-2-(4-chloro-2,6-dimethyl-phenoxy)-3-methoxy-6-methyl-pyridine

Anal. For C$_{15}$H$_{15}$BrClNO$_2$calc.: C, 50.52; H, 4.24; N, 3.93; found: C, 50.52; H, 4.37; N, 3.91.

Preparation S

4-Bromo-2-(4-chloro-2-methoxy-phenoxy)-3-methoxy-6-methyl-pyridine

1H NMR(CDCl$_3$) d 6.9–7.1(m,4H), 3.94(s,3H), 3.71(s,3H), 2.21s,3H) ppm.

Preparation T

4-Bromo-2-(3-chloro-2,6-dimethoxy-phenoxy)-3-methoxy-6-methyl-pyridine

1H NMR(CDCl$_3$) d 7.17(d,1H), 6.96(s,1H), 6.66(d,1H), 3.97(s,3H), 3.79(s,3H), 3.70(s,3H), 2.18(s,3H) ppm.

Preparation U

4-Bromo-3-methoxy-6-methyl-2-(2,4,6-trimethoxy-phenoxy)-pyridine

1H NMR(CDCl$_3$) d 6.90(s,1H), 6.19(s,2H), 3.968(s,3H), 3.80(s,3H), 3.71(s,6H), 2.18(s,3H) ppm.

Preparation V

4-Bromo-3-methoxy-2-(4-methoxy-2,6-dimethyl-phenoxy)-6-methyl-pyridine

1H NMR(CDCl$_3$) d 6.92(s,1H), 6.60(s,2H), 3.98(s,3H), 3.78(s,3H), 2.18(s,3H), 2.07(s,6H) ppm.

Preparation W

4-Bromo-2-(4-chloro-2,6-dimethyl-phenoxy)-3-ethoxy-6-methyl-pyridine

1H NMR(CDCl$_3$) d 7.099s,2H), 7.00(s,1H), 4.28(q,2H), 2.22(s,3H), 2.10(s,6H), 1.51(t,3H) ppm.

Preparation X

4-Bromo-3,6-dimethyl-2-(2,4,6-trimethoxy-phenoxy)-pyridine

1H NMR(CDCl$_3$) d 6.99(s,1H), 6.25(s,2H), 3.86(s,3H), 3.77(s,6H), 2.47(s,3H), 2.25(s,3H) ppm.

Preparation Y

4-Chloro-2-(4-chloro-2,6-dimethyl-phenoxy)-6-methyl-1-oxy-nicotinic acid methyl ester

Preparation RR

4-Chloro-2-(4-chloro-2,6-dimethyl-phenoxy)-6-methyl-nicotinic acid methyl ester

1H NMR(CDCl$_3$) d 7.03(s,2H), 6.869s,1H), 3.969s,3H), 2.259s,3H), 2.05(s,6H) ppm.

Preparation Z

4-Chloro-6-methyl-2-(2,4,6-trimethyl-phenoxy)-pyridine-3-carbaldehyde

The title compound was prepared by oxidation of 4-chloro-6-methyl-2-(2,4,6-trimethyl-phenoxy)-pyridin-3- yl-methanol with pyridinium chlorochromate in methylene chloride at room temperature. The desired product was isolated after column chromatography to give a green solid (80% yield). 1H NMR(CDCl₃) d 10.66(s,1H), 6.91(s,3H), 2.31(s,3H), 2.07(s,3H) ppm.

Preparation M 2-(4-Bromo-2,6-dimethyl-phenoxy)-4-chloro-6-methyl-nicotinic acid methyl ester mp. 108–110° C.; Anal. For $C_{16}H_{15}BrClNO_3$ calc., 49.96; H, 3.93; N, 3.64; found: C, 50.07; H, 4.10; N, 3.57.

Preparation BB

4-Chloro-2-(4-chloro-2-methoxy-phenoxy)-6-methyl-1-oxy-nicotinic acid methyl ester mp. 117–120° C., Anal. For $C_{15}H_{13}NO_5Cl_2$ calc.: C, 50.30; H, 3.66; N, 3.91; Found: C, 50.41; H, 3.55; N, 4.00.

Preparation CC

4-Chloro-2-(4-chloro-2-methoxy-phenoxy)-6-methyl-nicotinic acid methyl ester mp. 92–93° C., Anal. For $C_{15}H_{13}NO_4Cl_2$ calc.: C, 52.65; H, 3.83; N, 4.09; found: C, 52.34; H, 3.85; N, 4.13.

Preparation DD

[1-(tert-Butyl-dimethyl-silanyloxymethyl)-propyl]-[2-(4-chloro-2,6-dimethy-phenoxy)-3,6-dimethyl-pyridin-4-yl]-amine 1H NMR(CDCl₃) d 7.06(s,2H), 6.12(s,1H), 4.3(d,1H), 3.6–3.8(m,2H), 3.4(m,1H), 2.16(s,3H), 2.14(s,3H), 2.10(s,6H), 1.5–1.8(m,2H), 1.03(t,3H), 0.95(s,9H), 0.09(m,6H) ppm.

The following compounds were prepared by a method analogous to that described in Example 160, using an appropriate 4-bromo-2-(substituted phenoxy)-6-alkyl or alkoxy-pyridine with 1-(tert-Butyl-dimethyl-silanyloxymethyl)-propylamine.

Preparation EE

[1-(tert-Butyl-dimethyl-silanyloxymethyl)-propyl]-[3-methoxy-6-methyl-2-(2,4,6-trimethyl-phenoxy)-pyridin-4-(S)-yl]-amine 1H NMR (CDCl₃) d 6.84(s,2H), 6.08(s,1H), 4. 8(d,1H), 3.88(s,3H), 3.5–3.7(m,2H), 3.3(m,1H), 2.27(s,3H), 2.099s, 3H), 2.07(s,6H), 1.75(m,1H), 1.55(m,1H), 0.97(t,3h), 0.89 (s,9H), 0.04(s,6H) ppm.

Preparation FF

[1-(tert-Butyl-dimethyl-silanyloxymethyl)-propyl]-[2-(4-chloro-2,6-dimethyl-phenoxy)-3-methoxy-6-methyl-pyridin-4-yl]-amine 1H NMR(CDCl₃) d 7.02(s,2H), 6.10(s,1H), 4.80(d,1H), 3.87(s,3H), 3.6–3.7(m,2H), 3.30(m,1H), 2.09(s,3H), 2.08(s, 6H), 1.75(m,1H), 1.55(m,1H), 0.97(t,3H), 0.89(s,9H), 0.03 (s,6H) ppm.

Preparation GG

4-[1-(tert-Butyl-dimethyl-silanyloxymethyl)-propylamino]-2-(4-chloro-2,6-dimethyl-phenoxy)-6-methyl-pyridin-3-ol 1H NMR(CDCl₃) d 7.01 (s,2H), 6.15(s,1H), 4.46(d,1H), 3.7(m,1H), 3.6(m,1H), 3.4(m,1H), 2.09(s,3H), 2.08(s,6H), 1.5–1.8(m,2H), 1.06(s,9H), 0.98(t,3H), 0.24(s,6H) ppm.

Preparation HH

[1-(tert-Butyl-dimethyl-silanyloxymethyl)-propyl]-[3-methoxy-6-methyl-2-(2,4,6-trimethoxy-phenoxy)-pyridin-4-yl]-amine 1H NMR(CDCl₃) d 6.19(s,2H), 6.09(s,1H), 3.86(s,3H), 3.80(s,3H), 3.73(s,6H), 3.3(m,1H), 2.16(s,3H), 1.75(m,1H), 1.5(m,1H), 0.95(t,3H), 0.89(s,9H), 0.04(s,6H) ppm.

Preparation II

4-{4-[1-(tert-Butyl-dimethyl-silanyloxymethyl)-propylamino]-3-methoxy-6-methyl-pyridin-2-yloxy}-3,5-dimethyl-benzonitrile 1H NMR(CDCl₃) d 7.40(s,2H), 6.19(s,1H), 4.90(brs,1H), 3.87(s,3H), 3.70(m,2H), 3.3(m,1H), 2.19(m,9H), 1.5–1.8(m, 2H), 1.02(t,3H), 093(s,9H), 0.09(s,6H) ppm.

What is claimed is:

1. A compound of the formula

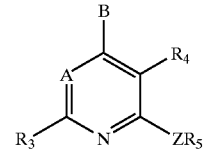

I or a pharmaceutically acceptable salt thereof, wherein

A is —$CR_7$;

B is —$NR_1R_2$, —$CR_1R_2R_{11}$, —$C(=CR_2R_{12})R_1$, —$NHCHR_1R_2$, —$OCHR_1R_2$, —$SCHR_1R_2$, —$CHR_2OR_1$, —$CHR_1OR_2$, —$CHR_2SR_1$, —$CHR_2NR_1R_2$, —$CHR_1NHR_2$, —$CHR_1N(CH_3)R_2$, or —$NR_{12}NR_1R_2$;

Z is NH, O, S, —$N(C_1-C_2$ alkyl), —$NC(O)CF_3$, or —$C(R_{13}R_{14})$, wherein $R_{13}$ and $R_{14}$ are each, independently, hydrogen, trifluoromethyl or methyl, or one of $R_{13}$ and $R_{14}$ is cyano and the other is hydrogen or methyl, or —$C(R_{13}R_{14})$ is a cyclopropyl group, or Z is nitrogen or CH and forms a five or six membered heterocyclic ring fused with $R_5$, which ring optionally includes two or three further hetero members selected independently from oxygen, nitrogen, $NR_{12}$, and $S(O)_m$, and optionally includes from one to three double bonds, and is optionally substituted with halo, $C_1-C_4$ alkyl, —$O(C_1-C_4$ alkyl), $NH_2$, $NHCH_3$, $N(CH_3)_2$, $CF_3$, or $OCF_3$, with the proviso that said ring does not include any —S—S—, —S—O—, —N—S—, or —O—O— bonds, and does not include more than two oxygen or $S(O)_m$ heterologous members;

$R_1$ is C(O)H, C(O)($C_1-C_6$ alkyl), C(O)($C_1-C_6$ alkylene) ($C_3-C_8$ cycloalkyl), C(O)($C_3-C_8$ cycloalkylene) ($C_3-C_8$ cycloalkyl), C(O)($C_1-C_6$ alkylene)($C_4-C_8$ heterocycloalkyl), —C(O)($C_3-C_8$ cycloalkylene) ($C_4-C_8$ heterocycloalkyl), $C_3-C_8$ cycloalkyl, $C_4-C_8$ heterocycloalkyl, —($C_1-C_6$ alkylene)($C_3-C_8$ cycloalkyl), —($C_3-C_8$ cycloalkylene)($C_3-C_8$ cycloalkyl), —($C_1-C_6$ alkylene)($C_4-C_8$ heterocycloalkyl), —($C_3-C_8$ cycloalkylene)($C_4-C_8$ heterocycloalkyl), or —O—aryl, or —O—($C_1-C_6$ alkylene)-aryl; wherein said aryl, $C_4-C_8$ heterocycloalkyl, $C_1-C_6$ alkyl, $C_3-C_8$ cycloalkyl, $C_3-C_8$ cycloalkylene, and $C_1-C_6$ alkylene groups may each independently be optionally substituted with from one to six fluoro and may each independently be optionally substituted with one or two substituents $R_8$ independently selected from the group consisting of $C_1$–$C_4$ alkyl, —$C_3$–$C_8$ cycloalkyl, hydroxy, chloro, bromo, iodo, $CF_3$, —O—($C_1$–$C_6$alkyl), —O—($C_3$–$C_5$ cycloalkyl), —O—CO—($C_1$–$C_4$ alkyl), —O—CO—NH($C_1$–$C_4$ alkyl), —O—CO—N($R_{24}$)($R_{25}$), —N($R_{24}$)($R_{25}$), —S($C_1$–$C_4$ alkyl), —S($C_3$–$C_5$ cycloalkyl), —N($C_1$–$C_4$alkyl)CO($C_1$–$C_4$ alkyl), —NHCO($C_1$–$C_4$ alkyl), —COO($C_1$–$C_4$ alkyl), —CONH($C_1$–$C_4$ alkyl), —CON($C_1$–$C_4$ alkyl)($C_1$–$C_2$ alkyl), CN, $NO_2$, —$OSO_2$($C_1$–$C_4$ alkyl), $S^+$($C_1$–$C_6$ alkyl)($C_1$–$C_2$ alkyl) $I^-$, —SO($C_1$–$C_4$ alkyl) and —$SO_2$($C_1$–$C_4$ alkyl); and wherein the $C_1$–$C_6$ alkyl, $C_1$–$C_6$ alkylene, $C_5$–$C_8$ cycloalkyl, $C_5$–$C_8$ cycloalkylene, and $C_5$–$C_8$ heterocycloalkyl moieties of $R_1$ may optionally independently include from one to three double or triple bonds; and wherein the $C_1$–$C_4$ alkyl moieties and $C_1$–$C_6$ alkyl moieties of $R_8$ can optionally independently be substituted with hydroxy, amino, $C_1$–$C_4$ alkyl, aryl, —$CH_2$-aryl, $C_3$–$C_5$ cycloalkyl, or —O—($C_1$–$C_4$ alkyl), and can optionally independently be substituted with from one to six fluoro, and can optionally include one or two double or triple bonds; and wherein each heterocycloalkyl group of $R_1$ includes from one to three heteromoieties selected from oxygen, $S(O)_m$, nitrogen, and $NR_{12}$;

$R_2$ is hydrogen, $C_1$–$C_{12}$ alkyl, $C_3$–$C_8$ cycloalkyl, $C_4$–$C_8$ heterocycloalkyl, —($C_1$–$C_6$ alkylene)($C_3$–$C_8$ cycloalkyl), —($C_3$–$C_8$ cycloalkylene)($C_3$–$C_8$ cycloalkyl), —($C_1$–$C_6$ alkylene)($C_4$–$C_8$ heterocycloalkyl), —($C_3$–$C_8$ cycloalkylene)($C_4$–$C_8$ heterocycloalkyl), aryl, —($C_1$–$C_6$ alkylene)aryl, or —($C_3$–$C_8$ cycloalkylene)(aryl); wherein each of the foregoing $R_2$ groups may optionally be substituted with from one to three substituents independently selected from chloro, fluoro, and $C_1$–$C_6$ alkyl, wherein one of said one to three substituents can further be selected from bromo, iodo, $C_1$–$C_6$ alkoxy, —OH, —O—CO—($C_1$–$C_6$ alkyl), —O—CO—N($C_1$–$C_4$ alkyl)($C_1$–$C_2$ alkyl), —S($C_1$–$C_6$ alkyl), —S(O)($C_1$–*$C_6$ alkyl), —$S(O)_2$($C_1$–$C_6$ alkyl), $S^+$($C_1$–$C_6$ alkyl)($C_1$–$C_2$ alkyl) $I^-$, CN, and $NO_2$; and wherein the $C_1$–$C_{12}$ alkyl, —($C_1$–$C_6$ alkylene), —($C_5$–$C_8$ cycloalkyl), —($C_5$–$C_8$ cycloalkylene), and —($C_5$–$C_8$ heterocycloalkyl) moieties of $R_2$ may optionally independently include from one to three double or triple bonds; and wherein each heterocycloalkyl group of $R_2$ includes from one to three heteromoieties selected from oxygen, $S(O)_m$, nitrogen, and $NR_{12}$;

or when $R_1$ and $R_2$ are as in —$NHCHR_1R_2$, —$OCHR_1R_2$, —$SCHR_1R_2$, —$CHR_1R_2$ or —$NR_1R_2$, $R_1$ and $R_2$ of B may form a saturated 5-to 8-membered ring which may optionally include one or two double bonds and in which one or two of the ring carbons may optionally be replaced by an oxygen, $S(O)_m$, nitrogen or $NR_{12}$; and which carbocyclic ring can optionally be substituted with from 1 to 3 substituents selected from the group consisting of hydroxy, $C_1$–$C_4$ alkyl, fluoro, chloro, bromo, iodo, $CF_3$, —O—($C_1$–$C_4$ alkyl), —O—CO—($C_1$–$C_4$ alkyl), —O—CO—NH($C_1$–$C_4$ alkyl), —O—CO—N($C_1$–$C_4$ alkyl)($C_1$–$C_2$ alkyl), —NH($C_1$–$C_4$ alkyl), —N($C_1$–$C_2$ alkyl)($C_1$–$C_4$ alkyl), —S($C_1$–$C_4$ alkyl), —N($C_1$–$C_4$ alkyl)CO($C_1$–$C_4$ alkyl), —NHCO($C_1$–$C_4$ alkyl), —COO($C_1$–$C_4$ alkyl), —CONH($C_1$–$C_4$ alkyl), —CON($C_1$–$C_4$ alkyl)($C_1$–$C_2$ alkyl), CN, $NO_2$, —$OSO_2$($C_1$–$C_4$ alkyl), —SO($C_1$–$C_4$ alkyl), and —$SO_2$($C_1$–$C_4$ alkyl), wherein one of said one to three substituents can further be selected from phenyl;

$R_3$ is methyl, ethyl, fluoro, chloro, bromo, iodo, cyano, methoxy, $OCF_3$, $NH_2$, NH($C_1$–$C_2$ alkyl), N($CH_3$)$_2$, —$NHCOCF_3$, —$NHCH_2CF_3$, $S(O)_m$($C_1$–$C_4$ alkyl), $CONH_2$, —$CONHCH_3$, $CON(CH_3)_2$, —$CF_3$, or $CH_2OCH_3$;

$R_4$ is hydrogen, $C_1$–$C_4$ alkyl, $C_3$–$C_5$ cycloalkyl, —($C_1$–$C_4$ alkylene)($C_3$–$C_5$ cycloalkyl), —($C_3$–$C_5$ cycloalkylene)($C_3$–$C_5$ cycloalkyl), cyano, fluoro, chloro, bromo, iodo, —$OR_{24}$, $C_1$–$C_6$ alkoxy, —O—($C_3$–$C_5$ cycloalkyl), —O—($C_1$–$C_4$ alkylene)($C_3$–$C_5$ cycloalkyl), —O—($C_3$–$C_5$ cycloalkylene)($C_3$–$C_5$ cycloalkyl), —$CH_2SC(S)O$($C_1$–$C_4$ alkyl), —$CH_2OCF_3$, $CF_3$, amino, nitro, —$NR_{24}R_{25}$, —($C_1$–$C_4$ alkylene)—$OR_{24}$, —($C_1$–$C_4$ alkylene)Cl, —($C_1$–$C_4$ alkylene)$NR_{24}R_{25}$, —$NHCOR_{24}$, —$NHCONR_{24}R_{25}$, —C=$NOR_{24}$, —$NHNR_{24}R_{25}$, —$S(O)_mR_{24}$, —$C(O)R_{24}$, —OC(O)$R_{24}$, —C(O)CN, —C(O)$NR_{24}R_{25}$, —C(O)$NHNR_{24}R_{25}$, and —$COOR_{24}$, wherein the alkyl and alkylene groups of $R_4$ may optionally independently include one or two double or triple bonds and may optionally independently be substituted with one or two substituents $R_{10}$ independently selected from hydroxy, amino, —$NHCOCH_3$, —$NHCOCH_2Cl$, —NH($C_1$–$C_2$ alkyl), —N($C_1$–$C_2$ alkyl)($C_1$–$C_2$ alkyl), —COO($C_1$–$C_4$ alkyl), —COOH, —CO($C_1$–$C_4$ alkyl), $C_1$–$C_6$ alkoxy, $C_1$–$C_3$ thioalkyl, cyano and nitro, and with one to four substituents independently selected from fluoro and chloro;

$R_5$ is aryl or heteroaryl and is substituted with from one to four substituents $R_{27}$ independently selected from halo, $C_1$–$C_{10}$ alkyl, —($C_1$–$C_4$ alkylene)($C_3$–$C_8$ cycloalkyl), —($C_1C_4$ alkylene)($C_4$–$C_8$ heterocycloalkyl), —($C_3$–$C_8$ cycloalkyl), —($C_4$–$C_8$ heterocycloalkyl), —($C_3$–$C_8$ cycloalkylene)($C_3$–$C_8$ cycloalkyl), —($C_3$–$C_8$ cycloalkylene)($C_4$–$C_8$ heterocycloalkyl), $C_1$–$C_4$ haloalkyl, $C_1$–$C_4$ haloalkoxy, nitro, cyano, —$NR_{24}R_{25}$, —$NR_{24}COR_{25}$, —$NR_{24}CO_2R_{26}$, —$COR_{24}$, —$OR_{25}$, —$CONR_{24}R_{25}$, —CO($NOR_{22}$)$R_{23}$, —$CO_2R_{26}$, —C=N($OR_{22}$)$R_{23}$, and —$S(O)_mR_{23}$; wherein said $C_1$–$C_{10}$ alkyl, $C_3$–$C_8$ cycloalkyl, ($C_1$–$C_4$ alkylene), ($C_3$–$C_8$ cycloalkyl), ($C_3$–$C_8$ cycloalkylene), and ($C_4$–$C_8$ heterocycloalkyl) groups can be optionally substituted with from one to three substituents independently selected form $C_1$–$C_4$ alkyl, $C_3$–$C_8$ cycloalkyl, ($C_1$–$C_4$ alkylene)($C_3$–$C_8$ cycloalkyl), —($C_3$–$C_8$ cycloalkylene)($C_3$–$C_8$ cycloalkyl), $C_1$–$C_4$ haloalkyl, hydroxy, $C_1$–$C_6$ alkoxy, nitro halo, cyano, —$NR_{24}R_{25}$, —$NR_{24}COR_{25}$, $NR_{24}CO_2R_{26}$, —$COR_{24}$, —$OR_{25}$, —$CONR_{24}R_{25}$, $CO_2R_{26}$, —CO($NOR_{22}$)$R_{25}$, and —$S(O)_mR_{23}$; and wherein two adjacent substituents of the $R_5$ group can optionally form a 5–7 membered ring, saturated or unsaturated, fused to $R^5$, which ring optionally can include one, two, or three heterologous members independently selected from O, $S(O)_m$, and N, but not any —S—S—, —O—O—, —S—O—, or —N—S— bonds, and which ring is optionally substituted with $C_1$–$C_4$ alkyl, $C_3$–$C_8$ cycloalkyl, —($C_1$–$C_4$ alkylene)($C_3$–$C_8$ cycloalkyl), —($C_3$–$C_8$ cyloalkylene)($C_3$–$C_8$ cycloalkyl), $C_1$–$C_4$ haloalkyl, nitro, halo, cyano —$NR_{24}R_{25}$, $NR_{24}COR_{25}$, $NR_{24}CO_2R_{26}$, —$COR_{24}$, —$OR_{25}$, —$CONR_{24}R_{25}$, $CO_2R_{26}$, —CO($NOR_{26}$)$R_{25}$, or —$S(O)_mR_{23}$; wherein one of said one to four optional substituents $R_{27}$ can further be selected from —$SO_2NH$($C_1$–$C_4$ alkyl), —$SO_2NH$($C_1$–$C_4$ alkylene)($C_3$–$C_8$ cycloalkyl), —$SO_2NH$($C_3$–$C_8$ cycloalkyl), —$SO_2NH$($C_3$–$C_8$ cycloalkylene)($C_3$–$C_8$ cycloalkyl), —$SO_2N(C_1$–$C_4$ alkyl)($C_1$–$C_2$ alkyl), —$SO_2NH_2$, —$NHSO_2(C_1$–$C_4$ alkyl), —$NHSO_2(C_3$–$C_8$ cycloalkyl), —$NHSO_2(C_1$–$C_4$ alkylene)($C_3$–$C_8$ cycloalkyl), and —$NHSO_2(C_3$–$C_8$ cycloalkylene)($C_3$–$C_8$ cycloalkyl); and wherein the alkyl, and alkylene groups of $R_5$ may independently optionally include one double or triple bond;

$R_7$ is hydrogen, methyl, fluoro, chloro, bromo, iodo, cyano, hydroxy, —$O(C_1$–$C_2$ alkyl), —$O$(cyclopropyl), —$COO(C_1$–$C_2$ alkyl), —$COO(C_3$–$C_8$ cycloalkyl), —$OCF_3$, $CF_3$, —$CH_2OH$, or $CH_2OCH_3$;

$R_{11}$ is hydrogen, hydroxy, fluoro, ethoxy, or methoxy;

$R_{12}$ is hydrogen or $C_1$–$C_4$ alkyl;

$R_{22}$ is independently at each occurrence selected from hydrogen, $C_1$–$C_4$ alkyl, $C_1$–$C_4$ haloalkyl, $C_3$–$C_6$ alkenyl, $C_3$–$C_6$ alkynyl, $C_3$–$C_8$ cycloalkyl;

$R_{23}$ is independently at each occurrence selected from $C_1$–$C_4$ alkyl, $C_1$–$C_4$ haloalkyl, $C_2$–$C_8$ alkoxyalkyl, $C_3$–$C_8$ cycloalkyl, aryl, —$(C_1$–$C_4$ alkylene)aryl, piperidine, pyrrolidine, piperazine, N-methylpiperazine, morpholine, and thiomorpholine;

$R_{24}$ and $R_{25}$ are independently at each occurrence selected from hydrogen, —$C_1$–$C_4$ alkyl, $C_1$–$C_4$ haloalkyl, —$(C_1$–$C_4$ alkylene)OH, —$(C_1$–$C_4$ alkylene)—O—$(C_1$–$C_4$ alkyl), —$(C_1$–$C_4$ alkylene)—O—$(C_3$–$C_5$ cycloalkyl), $C_3$–$C_8$ cycloalkyl, —$(C_1$–$C_4$ alkylene)($C_3$–$C_8$ cycloalkyl), —$(C_3$–$C_8$ cycloalkylene)($C_3$–$C_8$ cycloalkyl), —$C_4$–$C_8$ heterocycloalkyl, —$(C_1$–$C_4$ alkylene)($C_4$–$C_8$ heterocycloalkyl), —$(C_3$–$C_8$ cycloalkylene)($C_4$–$C_8$ heterocycloalkyl), aryl, and —$(C_1$–$C_4$ alkylene)(aryl), wherein the —$C_4$–$C_8$ heterocycloalkyl groups can each independently optionally be substituted with aryl, $CH_2$-aryl, or $C_1$–$C_4$ alkyl, and can optionally include one or two double or triple bonds; or, when $R_{24}$ and $R_{25}$ are as $NR_{24}R_{25}$, —$C(O)NR_{24}R_{25}$, —$(C_1C_4$ alkylene)$NR_{24}R_{25}$, or —$NHCONR_{24}R_{25}$, then $NR_{24}R_{25}$ may further optionally form a 4 to 8 membered heterocyclic ring optionally including one or two further hetero members independently selected from $S(O)_m$, oxygen, nitrogen, and $NR_{12}$, and optionally including from one to three double bonds;

$R_{26}$ is independently at each occurrence selected from $C_1$–$C_4$ alkyl, $C_1$–$C_4$ haloalkyl, $C_3$–$C_8$ cycloalkyl, —$(C_1$–$C_4$ alkylene)($C_3$–$C_8$ cycloalkyl), —$(C_3$–$C_8$ cycloalkylene)($C_3$–$C_8$ cycloalkyl), aryl, and —$(C_1$–$C_4$ alkylene)(aryl); and wherein each m is independently zero, one, or two, with the proviso that heterocycloalkyl groups of the compound of formula I do not include any —S—S—, —S—O—, —N—S—, or —O—O— bonds, and do not include more than two oxygen or $S(O)_m$ heterologous members.

2. A compound according to claim 1, wherein $R_4$ is —$NHCH_2CF_3$, —$CONHNH_2$, —$CONHNHCH_3$, —$OCF_3$, fluoro, —$OCHF_2$, —$OCH_2(C_3$–$C_5$ cycloalkyl), —$O$—$(C_3$–$C_5$ cycloalkyl), —$SCH_2(C_3$–$C_5$ cycloalkyl), —$S(C_3$–$C_5$ cycloalkyl), —$OCH_3$, —$CH_3$, —$CH_2CH_3$, chloro, bromo, —$CF_3$, —$CH_2OH$, —$CH_2OCH_3$, —$CH_2OCF_3$, —$SCH_3$, —$S(O)CH_3$, —$S(O)_2CH_3$, —$C(O)CH_3$, —$NR_{24}R_{25}$, —$NO_2$, —$CH(OH)CH_3$, or —$CN$.

3. A compound according to claim 1, wherein $R_4$ is —$C(O)NR_{24}R_{25}$ or —$C(O)NHNR_{24}R_{25}$.

4. A compound according to claim 1, wherein $R_4$ is —$(C_1$–$C_4$ alkylene)$NR_{24}R_{25}$.

5. A compound according to claim 1, wherein $R_4$ is —$COOCH_3$ or —$COOCH_2CH_3$.

6. A compound of formula I according to claim 1, wherein Z is O; B is —$NHCHR_1R_2$, wherein $R_1$ is —$C(O)H$ or —$C(O)(C_1$–$C_6$ alkyl), wherein said $C_1$–$C_6$ alkyl is optionally substituted with from one to six fluoro atoms or one or two $R_8$ independently selected from —$C_1$–$C_4$ alkyl, hydroxy and —$O$—$(C_1$–$C_6$ alkyl), and wherein $R_2$ is —$C_1$–$C_{12}$ alkyl optionally including from one to three double or triple bonds and optionally substituted with from one three substituents selected from fluoro and $C_1$–C6 alkyl; $R_5$ is phenyl, pyridyl or pyrimidyl, substituted with two or three $R_{27}$ groups selected from halo, —$(C_1$–$C_4$ haloalkyl), —$C(O)R_{24}$, —$OR_{25}$, —$C(O)NR_{24}R_{25}$, and $C_1$–$C_{10}$ alkyl which is optionally substituted with one to three substituents selected from hydroxy, $C_1$–$C_6$ alkoxy, and —$NR_{24}R_{25}$; and $R_4$ is —$C(O)NR_{24}R_{25}$.

7. A compound of formula I according to claim 1, wherein Z is C; B is —$NHCHR_1R_2$, wherein $R_1$ of —$NHCHR_1R_2$ is —$C(O)H$ or —$C(O)(C_1$–$C_6$ alkyl), wherein said $C_1$–$C_6$ alkyl is optionally substituted with from one to six fluoro atoms or one or two $R_8$ independently selected from —$C_1$–$C_4$ alkyl, hydroxy and —$O$—$(C_1$–$C_6$ alkyl), and wherein $R_2$ of —$NHCHR_1R_2$ is —$C_1$–$C_{12}$ alkyl optionally including from one to three double or triple bonds and optionally substituted with from one three substituents selected from fluoro and $C_1$–$C_6$ alkyl; $R_5$ is phenyl, pyridyl or pyrimidyl, substituted with two or three $R_{27}$ groups selected from halo, —$(C_1$–$C_4$ haloalkyl), —$C(O)R_{24}$, —$OR_{25}$, —$C(O)NR_{24}R_{25}$, and $C_1$–$C_{10}$ alkyl which is optionally substituted with one to three substituent selected from hydroxy, $C_1$–$C_6$ alkoxy, and —$NR_{24}R_{25}$; and $R_4$ is —$NR_1R_2$, wherein $R_1$ of —$NR_1R_2$ is $C_1$–$C_6$ alkyl, $C_3$–$C_8$ cycloalkyl, or —$(C_1$–$C_6$ alkylene)($C_3$–$C_8$ cycloalkyl), and $R_2$ of —$NR_1R_2$ is $C_1$–$C_{12}$ alkyl optionally including from one to three double or triple bonds and optionally substituted with from one three fluoro atoms.

8. A compound selected from:

2-(4-chloro-2,6-dimethyl-phenoxy)-4-(1-hydroxymethyl-propylamino)-6,N-dimethyl-nicotinamide;

2-(4-chloro-2,6-dimethyl-phenoxy)-4-(1-methoxymethyl-propylamino)-6,N-dimethyl-nicotinamide;

2-(4-chloro-2,6-dimethyl-phenoxy)-4-(1-methoxymethyl-propylamino)-6-methyl-nicotinamide;

2-(4-bromo-2-methoxy-phenoxy)-4-(1-ethyl-propylamino)-6-methyl-nicotinamide;

2-(4-chloro-2,6-dimethyl-phenoxy)-4-(1-ethyl-2-methoxy-propylamino)-6-methyl-nicotinamide;

2-(4-chloro-2,6-dimethyl-phenoxy)-4-(1-ethyl-2-methoxy-propylamino)-6,N-dimethyl-nicotinamide;

2-(4-chloro-2-trifluoromethoxy-phenoxy)-4-(1-ethyl-propylamino)-6-methyl-nicotinamide;

2-(4-chloro-2-trifluoromethoxy-phenoxy)-4-(1-ethyl-propylamino)-6-N-dimethyl-nicotinamide;

2-(4-chloro-2,6-dimethyl-phenoxy)-4-(1S,2R-1-ethyl-2-methoxy-propylamino)-6,N-dimethyl-nicotinamide;

2-(4-chloro-2,6-dimethyl-phenoxy)-4-(1S,2S-1-ethyl-2-methoxy-propylamino)-6,N-dimethyl-nicotinamide;

2-(4-bromo-2-methoxy-phenoxy)-4-(1-ethyl-propylamino)-6-methyl-nicotinonitrile;

4-[4-(1-ethyl-propoxy)-3,6-dimethyl-pyridin-2-yloxy]-3,5-dimethyl-benzamide;

2-(4-chloro-2,6-dimethyl-phenoxy)-6-methyl-4-(1-methylsulfanylmethyl-propylamino)nicotinic acid methyl ester;

2-(4-chloro-2,6-dimethyl-phenoxy)-4-(1-hydroxymethyl-propylamino)-6-methyl-nicotinic acid methyl ester;

2-(4-bromo-2,6-dimethyl-phenoxy)-4-(1-ethyl-propylamino)-6-methyl-nicotinonitrile;

2-(4-chloro-2-trifluoromethoxy-phenoxy)-4-(1-ethyl-propylamino)-6-methyl-nicotinic acid methyl ester; and 2-(4-chloro-2,6-dimethyl-phenoxy)-6-methyl-4-(tetrahydro-furan-3-ylamino)-nicotinic acid methyl ester;

and pharmaceutically acceptable salts thereof.

9. A pharmaceutical composition for the treatment of (a) a disorder or condition the treatment of which can be effected or facilitated by antagonizing CRF, or (b) a disorder or condition selected from generalized anxiety disorder; panic; phobias, obsessive-compulsive disorder; post-traumatic stress disorder; sleep disorders induced by stress; pain perception mood disorders dysthemia; bipolar disorders; cyclothymia; chronic fatigue syndrome; stress-induced headache; irritable bowel syndrome; spastic colon; post operative ileus; diarrhea; stress-induced fever; gastrointestinal diseases; hemorrhagic stress; chemical dependencies or addictions, drug or alcohol withdrawal symptoms; stress-induced psychotic episodes; euthyroid sick syndrome; syndrome of inappropriate antidiuretic hormone; porcine stress syndrome hypertension; tachycardia; and congestive heart failure; comprising an amount of a compound according to claim 1 that is effective in the treatment of such disorder or condition, and a pharmaceutically acceptable carrier.

10. A method for the treatment of (a) a disorder or condition the treatment of which can be effected or facilitated by antagonizing CRF, or (b) a disorder or condition selected from generalized anxiety disorder; panic; phobias, obsessive-compulsive disorder; post-traumatic stress disorder; sleep disorders induced by stress; pain perception; mood disorders dysthemia; bipolar disorders; cyclothymia; chronic fatigue syndrome; stress-induced headache; irritable bowel syndrome, spastic colon; post operative ileus; diarrhea; stress-induced fever; gastrointestinal diseases; hemorrhagic stress; chemical dependencies or addictions, drug or alcohol withdrawal symptoms; stress-induced psychotic episodes; euthyroid sick syndrome; syndrome of inappropriate antidiuretic hormone; porcine stress syndrome hypertension; tachycardia; and congestive heart failure; comprising administering to a subject in need of said treatment an amount of a compound according to claim 1, that is effective in treating such disorder or condition.

11. A method of treating a condition comprising administering a compound of claim 1 in an amount effective to treat said condition, wherein said condition is selected from the group consisting of:
 a) abnormal circadian rhythm;
 b) depression, further wherein a second compound for treating depression is administered, said second compound for treating depression having an onset of action that is delayed with respect to that of said CRF antagonist; and
 c) emesis.

12. The method of claim 11 wherein the condition is abnormal circadian rhythm, and the compound is combined with a second compound useful for treating a sleep disorder.

13. The method of claim 12, wherein said second compound is selected from the group consisting of tachykinin antagonists, agonists for GABA brain receptors, metalonergic compounds, GABA brain receptor agonists, 5HT2 receptor antagonists, and D4 receptor binding.

14. The method of claim 11 wherein said condition is depression, and wherein said second compound having delayed action for treating depression is selected from the group consisting of selective serotonin reuptake inhibitors, tricyclic antidepressants, norepinephrine uptake inhibitors, lithium, bupropion, trazodone, and a tricyclic antidepressant and pharmaceutically acceptable salts and esters of the above-recited compounds.

15. The method claim 11 wherein said condition is emesis, further comprising administering a second compound for treating emesis.

16. The method of claim 15 wherein said second compound for treating emesis is selected from the group consisting of tachykinin antagonists, 5HT3 antagonists, GABA agonists, and substance P inhibitors.

17. A pharmaceutical composition for treating a condition comprising a compound of claim 1 in an amount effective to treat said condition and a pharmaceutically acceptable carrier, wherein said condition is selected from the group consisting of:
 a) abnormal circadian rhythm;
 b) depression, further wherein a second compound for treating depression is administered, said second compound for treating depression having an onset of action that is delayed with respect to that of said compound of claim 1; and
 c) emesis.

18. A pharmaceutical composition according to claim 17, wherein the condition is abnormal circadian rhythm, and the compound is combined with a second compound useful for treating a sleep disorder.

19. A pharmaceutical composition according to claim 18, wherein said second compound is selected from the group consisting of tachykinin antagonists, agonists for GABA brain receptors, metalonergic compounds, GABA brain receptor agonists, $5HT_2$ receptor antagonists, and D4 receptor binding.

20. A pharmaceutical composition according to claim 17 wherein said condition is depression, and wherein said second compound having delayed action for treating depression is selected from the group consisting of selective serotonin reuptake inhibitors, tricyclic antidepressants, norepinephrine uptake inhibitors, lithium, bupropion, trazodone, and a tricyclic antidepressant, and pharmaceutically acceptable salts and esters of the above-recited compounds.

21. A pharmaceutical composition according to claim 17 wherein said condition is emesis, further comprising administering a second compound for treating emesis.

22. A pharmaceutical composition according to claim 21 wherein said second compound for treating emesis is selected from the group consisting of tachykinin antagonists, 5HT3 antagonists, GABA agonists, and substance P inhibitors.

23. The pharmaceutical composition of claim 9, wherein the disorder or condition is a phobia selected from the group consisting of including social phobia, agoraphobia, and specific phobias.

24. The pharmaceutical composition of claim 9, wherein the disorder or condition is a pain perception, wherein the pain perception is fibromyalgia.

25. The pharmaceutical composition of claim 9, wherein the disorder or condition is depression.

26. The pharmaceutical composition of claim 25, wherein the depression is selected from the group consisting of major depression, single episode depression, recurrent depression, child abuse induced depression, mood disorders associated with premenstrual syndrome, and postpartum depression.

27. The pharmaceutical composition of claim 9, wherein the chemical dependency or addictions is selected from the group consisting of dependencies or addictions to alcohol, cocaine, heroin, and benzodiazapines.

28. The method of claim 10, wherein the disorder or condition is a phobia selected from the group consisting of including social phobia, agoraphobia, and specific phobias.

29. The method of claim 10, wherein the disorder or condition is a pain perception, wherein the pain perception is fibromyalgia.

30. The method of claim 10, wherein the disorder or condition is depression.

31. The method of claim 10, wherein the depression is selected from the group consisting of major depression, single episode depression, recurrent depression, child abuse induced depression, mood disorders associated with premenstrual syndrome, and postpartum depression.

32. The method of claim 10, wherein the chemical dependency or addictions is selected from the group consisting of dependencies or addictions to alcohol, cocaine, heroin, and benzodiazapines.

33. The method of claim 14, wherein the selective serotonin reuptake inhibitor is sertraline or fluoxetine or pharmaceutically acceptable salts and esters thereof and the tricyclic antidepressant is selected from the group consisting of imipramine, amitriptyline, trimipramine, doxepin, desipramine, nortriptyline, protriptyline, amoxapine, clomipramine, maprotiline, and carbamazepine and pharmaceutically acceptable salts and esters thereof.

34. The pharmaceutical composition of claim 20, wherein the selective serotonin reuptake inhibitor is sertraline or fluoxetine or pharmaceutically acceptable salts and esters thereof and the tricyclic antidepressant is selected from the group consisting of imipramine, amitriptyline, trimipramine, doxepin, desipramine, nortriptyline, protriptyline, amoxapine, clomipramine, maprotiline, and carbamazepine and pharmaceutically acceptable salts and esters thereof.

* * * * *